United States Patent
Rajendran et al.

(10) Patent No.: US 10,988,744 B2
(45) Date of Patent: Apr. 27, 2021

(54) METHOD OF PRODUCING ALKALINE PHOSPHATASE

(71) Applicant: Alexion Pharmaceuticals, Inc., Boston, MA (US)

(72) Inventors: Saravanamoorthy Rajendran, Middletown, CT (US); Rachael Alford, Guilford, CT (US); Sean Gallagher, Naas (IE); Anne Kantardjieff, Milford, CT (US); Jared Davis, Hamden, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 92 days.

(21) Appl. No.: 16/099,310

(22) PCT Filed: Jun. 6, 2017

(86) PCT No.: PCT/US2017/036133
§ 371 (c)(1),
(2) Date: Nov. 6, 2018

(87) PCT Pub. No.: WO2017/214130
PCT Pub. Date: Dec. 14, 2017

(65) Prior Publication Data
US 2020/0224182 A1 Jul. 16, 2020

Related U.S. Application Data

(60) Provisional application No. 62/464,209, filed on Feb. 27, 2017, provisional application No. 62/346,209, filed on Jun. 6, 2016.

(51) Int. Cl.
*C12N 9/16* (2006.01)
*C12Q 1/44* (2006.01)

(52) U.S. Cl.
CPC ................ *C12N 9/16* (2013.01); *C12Q 1/44* (2013.01); *C12Y 301/03001* (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Achord et al., "Human beta-glucuronidase: in vivo clearance and in vitro uptake by a glycoprotein recognition system on reticuloendothelial cells," Cell 15(1):269-278 (1978).

Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).

Advisory Action for U.S. Appl. No. 11/484,870, dated Dec. 20, 2007 (4 pages).

Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).

(Continued)

*Primary Examiner* — Hope A Robinson
(74) *Attorney, Agent, or Firm* — Clark & Elbing LLP

(57) ABSTRACT

The disclosure provides a method of producing recombinant alkaline phosphatase comprising: (i) culturing an alkaline phosphatase in a recombinant cell culture; (ii) obtaining a preparation of recombinant alkaline phosphatase from the cell culture; and (iii) minimizing in the preparation a concentration of at least one metal ion selected from the group consisting of: Nickel (Ni), Cobalt (Co), Copper (Cu), Manganese (Mn), Chromium (Cr), and Molybdenum (Mo).

17 Claims, 26 Drawing Sheets
Specification includes a Sequence Listing.

(56) References Cited

U.S. PATENT DOCUMENTS

| | | | |
|---|---|---|---|
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,908,932 B2 * | 3/2018 | Malanson ................. A61P 7/00 |
| 9,988,620 B2 | 6/2018 | Crine et al. |
| 10,000,532 B2 | 6/2018 | Crine et al. |
| 10,052,366 B2 * | 8/2018 | Crine ....................... C07K 7/08 |
| 10,449,236 B2 * | 10/2019 | Marozsan ............. A61K 38/465 |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 1985697 A1 | 10/2008 |
| EP | 1759001 B1 | 4/2011 |
| EP | 2158319 B1 | 12/2011 |
| JP | H08-70875 A | 3/1996 |

(56) References Cited

FOREIGN PATENT DOCUMENTS

| | | |
|---|---|---|
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/015011 A1 | 1/2009 |
| WO | WO-2009/023270 A2 | 2/2009 |
| WO | WO-2009/006732 A9 | 3/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Ahn et al., "Idiopathic calcium pyrophosphate dihydrate (CPPD) crystal deposition disease in a young male patient: a case report," J Korean Med Sci. 18(6):917-20 (2003).

Alexion Pharma International, "Product Monograph, Including Patient Medication Information. Strensiq™ (asfotase alfa), Solution for Injection 40 mg/mL & 100 mg/mL," <alexionpharma.ca/documents/Strensiq-PM-asfotase-alfa-14Aug2015.aspx>, prepared Aug. 14, 2015 (32 pages).

Alexion Third Quarter 2017 Earnings Call, "files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).

Alexion, "Highlights of Prescribing Information" for Strensiq®, 2018 (8 pages).

Ali et al., "Isolation and characterization of calcifying matrix vesicles from epiphyseal cartilage," Proc Natl Acad Sci USA. 67(3):1513-20 (1970).

Altarescu et al., "The efficacy of enzyme replacement therapy in patients with chronic neuronopathic Gaucher's disease," J Pediatr. 138(4):539-547 (2001).

Anderson et al., "Impaired calcification around matrix vesicles of growth plate and bone in alkaline phosphatase-deficient mice," Am J Pathol. 164(3):841-7 (2004).

Anderson et al., "Matrix vesicles in osteomalacic hypophosphatasia bone contain apatite-like mineral crystals," Am J Pathol. 151(6):1555-61 (1997).

(56) References Cited

OTHER PUBLICATIONS

Anderson, "Mechanism of Mineral Formation in Bone," *Pathology Reviews*. Emanuel Rubin and Ivan Damjanov (eds.), 13-23 (1990).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-37 (2005).
Appeal Brief as Filed in U.S. Appl. No. 12/638,527, dated Oct. 9, 2015 (101 pages).
Attwood, "The Babel of Bioinformatics," Science. 290(5491):471-3 (2000).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barranger et al., "Lessons learned from the development of enzyme therapy for Gaucher disease," J Inherit Metab Dis. 24(Suppl. 2):89-96 (2001).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Beertsen et al., "Root development in mice lacking functional tissue non-specific alkaline phosphatase gene: Inhibition of acellular cementum formation," J Dent Res. 78(6):1221-1229 (1999) (10 pages).
Belachew et al., "Infantile hypophosphatasia secondary to a novel compound heterozygous mutation presenting with pyridoxine-responsive seizures," JIMD Rep. 11:17-24 (2013).
Belkhouribchia et al., "Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. 135:218-225 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research. www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobyr et al., "High-resolution analysis of Zn(2+) coordination in the alkaline phosphatase superfamily by EXAFS and x-ray crystallography," J Mol Biol. 415(1):102-17 (2012).
Bobé et al., "Fas-mediated liver damage in MRL hemopoietic chimeras undergoing lpr-mediated graft-versus-host disease," J Immunol. 159:4197-4204 (1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).
Boskey et al., "Matrix vesicles promote mineralization in a gelatin gel," Calcif Tissue Int. 60(3):309-15 (1997).
Boskey, "Amorphous calcium phosphate: The contention of bone," J Dent Res. 76:1433-1436 (1997).
Boulet et al., "A population-based study of craniosynostosis in metropolitan Atlanta, 1989-2003," Am J Med Genet A. 146A(8):984-91 (2008).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2016).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts," J. Clin Endocrinol Metab. 92(8): 2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).
Carden et al., "Tracheomalacia and tracheobronchomalacia in children and adults: an in-depth review," Chest. 127(3):984-1005 (2005).
Center for Drug Evaluation and Research, "Application No. 125513Orig1s000," <www.accessdata.fda.gov/drugsatfda_docs/nda/2015/125513Orig1s000MedR.pdf>, review completed Oct. 20, 2015; retrieved on Jun. 1, 2016 (254 pages).
Chan et al., "Endoscope-assisted versus open repair of craniosynostosis: a comparison of perioperative cost and risk," J Craniofac Surg. 24(1):170-4 (2013).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).

(56) References Cited

OTHER PUBLICATIONS

Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz J Med Biol Res. 39(5):603-10 (2006).
Clarke, "Normal bone anatomy and physiology," Clin J Am Soc Nephrol. 3(Suppl 3):S131-9 (2008).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Communication from Examining Division for European Application No. 08757088.3, dated Apr. 20, 2011 (4 pages).
Communication from Examining Division for European Application No. 05739065.0, dated Jun. 18, 2009 (6 pages).
Communication from Examining Division for European Application No. 05739065.0, dated Jun. 11, 2010 (5 pages).
Communication pursuant to Rule 164(2)(b) and Article 94(3) EPC for European Application No. 16707571.2, dated Feb. 26, 2019 (12 pages).
Crawley et al., "Enzyme replacement therapy in a feline model of Maroteaux-Lamy syndrome," J Clin Invest. 97(8):1864-73 (1996).
Czerwinski et al., "Major morbidity and mortality rates in craniofacial surgery: an analysis of 8101 major procedures," Plast Reconstr Surg. 126(1):181-6 (2010).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
De Roo et al., "Infantile hypophosphatasia without bone deformities presenting with severe pyridoxine-resistant seizures," Mol Genet Metab. 111(3):404-7 (2014).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Declaration of Dr. Philippe Crine for European Patent Application No. 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
Di Mauro et al., "Kinetic characterization of hypophosphatasia mutations with physiological substrates," J Bone Miner Res. 17(8):1383-91 (2002).

Di Rocco et al., "Craniosynostosis and hypophosphatasia," Arch Pediatr. 24(5S2):5S89-5S92 (2017).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
Eade et al., "Pyrophosphate arthropathy in hypophosphatasia," Ann Rheum Dis. 40(2):164-70 (1981).
EBI Blast for Accession No. ATD17216. Entered Oct. 16, 2008 (1 page).
Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360:169-172 (1995).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
European Collection of Authenticated Cell Cultures (ECACC), General Cell Collection: NS0, Catalogue No. 85110503. Retrieved May 2, 2018 (3 pages).
Extended European Search Report for European Patent Application No. 12842640.0, dated Mar. 13, 2015 (7 pages).
Extended European Search Report for European Application No. 15907550.6, dated Jun. 4, 2019 (7 pages).
Examiner's Answer to Appeal Brief for U.S. Appl. No. 12/638,527, dated Feb. 23, 2016 (9 pages).
Extended European Search Report for European Application No. 08757088.3, dated Jun. 21, 2010 (6 pages).
Extended European Search Report for European Application No. 11774253.6, dated Oct. 14, 2013 (8 pages).
Extended European Search Report for European Application No. 11000196.3, dated Jun. 22, 2011 (6 pages).
Extended European Search Report for European Application No. 11004496.3, dated Aug. 26, 2011 (7 pages).
Extended European Search Report for European Application No. 18173111.8, dated Aug. 21, 2018 (9 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26): 1003-1007 (2017) (Article in Hungarian) (English Abstract included).
Fong et al., "Hypocalcemia: Updates in diagnosis and management for primary care," Can Fam Physician. 58(2):158-62 (2012).
Fraser, "Hypophosphatasia," Am J Med. 22(5):730-46 (1957).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).

(56) References Cited

OTHER PUBLICATIONS

Furbish et al., "Uptake and distribution of placental glucocerebrosidase in rat hepatic cells and effects of sequential deglycosylation," Biochim Biophys Acta. 673:425-434 (1981).

Furuya et al., "Structural requirements of C-type natriuretic peptide for elevation of cyclic GMP in cultured vascular smooth muscle cells," Biochem Biophys Res Commun. 183(3):964-969 (1992).

Garber et al., "Comparing outcomes and cost of 3 surgical treatments for sagittal synostosis: a retrospective study including procedure-related cost analysis," Neurosurgery. 81(4):680-7 (2017).

Garg, "Investigation of the role of FcRn in the absorption, distribution, and elimination of monoclonal antibodies," Dissertation: State University of New York at Buffalo, 2007 (Abstract only) (2 pages).

Gasque et al., "Improvement of the skeletal and dental hypophosphatasia phenotype in Alpl−/−mice by administration of soluble (non-targeted) chimeric alkaline phosphatase," Available in PMC Mar. 1, 2016, published in final edited form as: Bone. 72:137-147 (2015) (25 pages).

Gates et al., "Effects of age, sex, and comorbidities on the pediatric outcomes data collection instrument (PODCI) in the general population," J Pediatr Orthop. 35(2):203-9 (2015).

Gilbert et al., "Chimeric peptides of statherin and osteopontin that bind hydroxyapatite and mediate cell adhesion," J Biol Chem. 275(21):16213-8 (2000).

Ginelliová et al., "Sudden death associated with syndromic craniosynostosis," Forensic Sci Med Pathol. 12(4):506-9 (2016).

Glass et al., "The infant skull: a vault of information," Radiographics. 24(2):507-22 (2004).

Graham et al., "Characteristics of a human cell line transformed by DNA from human adenovirus type 5," J Gen Virol. 36(1):59-72 (1977).

Greenberg et al., "A homoallelic $Gly^{317}$ to Asp mutation in ALPL causes the perinatal (lethal) form of hypophosphatasia in Canadian Mennonites," Genomics. 17:215-217 (1993).

Greenwood et al., "Familial incidence and associated symptoms in a population of individuals with nonsyndromic craniosynostosis," Genet Med. 16(4):302-10 (2014).

Guañabens et al., "Calcific periarthritis as the only clinical manifestation of hypophosphatasia in middle-aged sisters," J Bone Miner Res. 29(4):929-34 (2014).

Guo et al., "Protein tolerance to random amino acid change," Proc Natl Acad Sci USA. 101(25):9205-9210 (2004).

Güzel Nur et al., "Pyridoxine-responsive seizures in infantile hypophosphatasia and a novel homozygous mutation in ALPL gene," J Clin Res Pediatr Endocrinol. 8(3):360-4 (2016).

Hagiwara et al., "Autocrine regulation of rat chondrocyte proliferation by natriuretic peptide C and its receptor, natriuretic peptide receptor-B," J Biol Chem. 269(14):10729-10733 (1994).

Hagiwara et al., "cGMP produced in response to ANP and CNP regulates proliferation and differentiation of osteoblastic cells," Am J Physiol Cell Physiol. 270:C1311-18 (1996) (9 pages).

Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).

Hancarova et al., "Hypophosphatasia due to uniparental disomy," Bone. 81:765-766 (2015).

Hardy et al., "Dissection of a carboxy-terminal region of the yeast regulatory protein RAP1 with effects on both transcriptional activation and silencing," Mol Cell Biol. 12(3):1209-1217 (1992).

Harmey et al., "Concerted regulation of inorganic pyrophosphate and osteopontin by Akp2, Enpp1, and Ank," Am J Pathol. 164(4):1199-1209 (2004).

Harmey et al., "Elevated skeletal osteopontin levels contribute to the hypophosphatasia phenotype in $Akp2^{-/-}$ mice," J Bone Miner Res. 21(9):1377-1386 (2006).

Harris, "The human alkaline phosphatases: what we know and what we don't know," Clin Chim Acta. 186:133-50 (1989).

Hawrylak et al., "The solubilization of tetrameric alkaline phosphatase from human liver and its conversion into various forms by phosphatidylinositol phospholipase C or proteolysis," J Biol Chem. 263(28):14368-14373 (1988).

Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).

Henthorn et al., "Missense mutations of the tissue-nonspecific alkaline phosphatase gene in hypophosphatasia," Clin Chem. 38(12):2501-5 (1992).

Herasse et al., "Molecular study of three cases of odontohypophosphatasia resulting from heterozygosity for mutations in the tissue non-specific alkaline phosphatase gene," J Med Genet. 40(8):605-9 (2003).

Herring, "Mechanical influences on suture development and patency," Front Oral Biol. 12:41-56 (2008).

Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).

Highlights of Prescribing Information for Strensiq™ (asfotase alfa) Injection, Alexion Pharmaceuticals, Inc., <www.alexion.com/Documents/strensiq_pi-10-2015.aspx> (2015) (19 pages).

Hofmann et al., "Asfotase alfa: enzyme replacement for the treatment of bone disease in hypophosphatasia," Drugs Today (Barc). 52(5):271-85 (2016).

Hofmann et al., "Chapter 15: Recombinant enzyme replacement therapy in hypophosphatasia," *Neuronal Tissue-Nonespecific Alkaline Phosphatase (TNAP): Subcellular Biochemistry*. Caroline Fonta and Laszlo Negyessy, 76:323-41 (2015).

Hofmann et al., "Clinical aspects of hypophosphatasia: an update," Clinic Rev Bone Miner Metab. 11(2):60-70 (2013).

Hofmann et al., "Compound heterozygosity of two functional null mutations in the ALPL gene associated with deleterious neurological outcome in an infant with hypophosphatasia," Bone. 55:150-7 (2013).

Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).

Hollis et al., "Current concepts in hypophosphatasia: case report and literature review," Int J Paediatr Dent. 23(3):153-9 (2013).

Horton et al., "Achondroplasia," Lancet. 370:162-72 (2007).

Hosain et al., "Targeted delivery of antineoplastic agent to bone: biodistribution studies of technetium-99m-labeled gem-bisphosphonate conjugate of methotrexate," J Nucl Med. 37(1):105-7 (1996).

Hult et al., "Engineered enzymes for improved organic synthesis," Curr Opin Biotechnol. 14:395-400 (2003).

Hunter et al., "Modulation of crystal formation by bone phosphoproteins: structural specificity of the osteopontin-mediated inhibition of hydroxyapatite formation," Biochem J. 300:723-728 (1994).

Husain et al., "Fc site-specific labeling of immunoglobulins with calf intestinal alkaline phosphatase," Bioconjug Chem. 5(5):482-90 (1994).

Hwang et al., "Update of diagnostic evaluation of craniosynostosis with a focus on pediatric systematic evaluation and genetic studies," J Korean Neurosurg Soc. 59(3):214-8 (2016).

Ikezawa, "Glycosylphosphatidylinositol (GPI)-anchored proteins," Biol Pharm Bull. 25(4):409-17 (2002).

Inoue et al., "Four functionally distinct C-type natriuretic peptides found in fish reveal evolutionary history of the natriuretic peptide system," Proc Natl Acad Sci USA. 100(17):10079-10084 (2003).

International Preliminary Report on Patentability for International Patent Application No. PCT/CA2011/050258, dated Nov. 15, 2012 (9 pages).

International Preliminary Report on Patentability for International Patent Application No. PCT/US2012/060869, dated Apr. 22, 2014 (7 pages).

(56) References Cited

OTHER PUBLICATIONS

International Preliminary Report on Patentability for International Patent Application No. PCT/US2012/039004, dated Apr. 22, 2014 (8 pages).
International Preliminary Report on Patentability for International Patent Application No. PCT/US2016/015366, dated Aug. 10, 2017 (10 pages).
International Preliminary Report on Patentability for International Patent Application No. PCT/US2016/049983, dated Sep. 11, 2018 (9 pages).
International Search Report and Written Opinion for International Application No. PCT/US18/26868, dated Sep. 7, 2018 (30 pages).
International Search Report and Written Opinion for International Patent Application No. PCT/CA2011/050807, dated Apr. 13, 2012 (18 pages).
International Search Report and Written Opinion for International Patent Application No. PCT/CA2011/050258, dated Jul. 29, 2011 (14 pages).
International Search Report and Written Opinion for International Patent Application No. PCT/US2012/039004, dated Nov. 2, 2012 (22 pages).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/US2015/058498, dated Jan. 22, 2016 (12 pages).
International Search Report and Written Opinion for International Patent Application No. PCT/US2016/025721, dated Aug. 17, 2016 (18 pages).
International Search Report and Written Opinion for International Patent Application No. PCT/US2016/047166, dated Nov. 7, 2016 (15 pages).
International Search Report and Written Opinion for International Patent Application No. PCT/US2016/039595, dated Feb. 21, 2017 (16 pages).
International Search Report and Written Opinion for International Patent Application No. PCT/US2017/025590, dated Jun. 29, 2017 (18 pages).
International Search Report and Written Opinion for International Patent Application No. PCT/US2017/025618, dated Jul. 11, 2017 (22 pages).
International Search Report and Written Opinion for International Patent Application No. PCT/US2017/047527, dated Nov. 6, 2017 (10 pages).
International Search Report and Written Opinion for International Patent Application No. PCT/US2016/054013, dated Dec. 13, 2016 (19 pages).
International Search Report and Written Opinion for International Patent Application No. PCT/US2018/020859, dated Jun. 19, 2018 (14 pages).
International Search Report and Written Opinion for International Patent Application No. PCT/US2018/025206, dated Jul. 3, 2018 (25 pages).
International Search Report and Written Opinion for International Patent Application No. PCT/US2015/064003, dated Mar. 31, 2016 (13 pages).
International Search Report and Written Opinion for International Patent Application No. PCT/US2017/036133, dated Aug. 24, 2017 (10 pages).
International Search Report and Written Opinion for International Patent Application No. PCT/US2015/039973, dated Oct. 5, 2015 (12 pages).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
International Search Report and Written Opinion for International Application No. PCT/US2019/045963, dated Jan. 30, 2020 (26 pages).
International Search Report for International Patent Application No. PCT/US2012/060869, dated Mar. 25, 2013 (5 pages).
Invitation to Pay Additional Fees for International Patent Application No. PCT/US2012/039004, dated Aug. 29, 2012 (2 pages).
Invitation to Pay Additional Fees for International Patent Application No. PCT/CA2011/050807, dated Feb. 13, 2012 (2 pages).
Invitation to Pay Additional Fees for International Patent Application No. PCT/US2016/015366, dated Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)—>Val mutation fails to reach the cell surface and undergoes proteasome-mediated degradation," J Biochem. 134(1):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Craniosynostosis," Eur J Hum Genet. 19(4):369-76 (2011).
Johnson et al., "Matrix vesicle plasma cell membrane glycoprotein-1 regulates mineralization by murine osteoblastic MC3T3 cells," J Bone Miner Res. 14(6):883-892 (1999).
Johnson et al., "Motor proficiency in children with neurofibromatosis type 1," Pediatr Phys Ther. 22(4):344-8 (2010).
Kabbani et al., "Craniosynostosis," Am Fam Physician. 69(12):2863-70 (2004).
Kajdic et al., "Craniosynostosis—Recognition, clinical characteristics, and treatment," Bosn J Basic Med Sci. 18(2):110-6 (2018).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Katsianou et al., "Signaling mechanisms implicated in cranial sutures pathophysiology: Craniosynostosis," BBA Clin. 6:165-76 (2016).
Kaufmann et al., "Influence of low temperature on productivity, proteome and protein phosphorylation of CHO cells," Biotechnol Bioeng. 63(5):573-82 (1999).
Khanna et al., "Pictorial essay: the many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
Kishnani et al., "Monitoring guidance for patients with hypophosphatasia treated with asfotase alfa," Mol Genet Metab. 122(1-2):4-17 (2017).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Kochendoerfer, "Protein & Peptide Drug Delivery—Third International Conference: Minimally invasive delivery methods, Sep. 22-23, Philadelphia, PA, USA," IDrugs. 6(11):1043-5 (2003).

(56) References Cited

OTHER PUBLICATIONS

Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Lazdunski et al., "Structure-function relationships for some metalloalkaline phosphatases of *E. coli*," Eur J Biochem. 8(4):510-7 (1969).
Le Du et al., "Crystal structure of alkaline phosphatase from human placenta at 1.8 Å resolution. Implication for a substrate specificity," J Biol Chem. 276(12):9158-65 (2001) (9 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Leung et al., "Outcome of perinatal hypophosphatasia in manitoba mennonites: a retrospective cohort analysis," JIMD Rep. 11:73-78 (2013).
Li et al., "Standard reference for the six-minute-walk test in healthy children aged 7 to 16 years," Am J Respir Crit Care Med. 176(2):174-80 (2007).
Li et al., "Timing of the Initiation of Bisphosphonates After Surgery for Fracture Healing: A Systematic Review and Meta-Analysis of Randomized Controlled Trials," Osteoporos Int. 26(2):431-41 (2015).
Linglart et al., "Hypophosphatasia," Curr Osteoporos Rep. 14(3):95-105; DOI 10.1007/s11914-016-0309-0 (2016) (11 pages).
Liu et al., "Tissue-nonspecific alkaline phosphatase deficiency causes abnormal craniofacial bone development in the Alpl(−/−) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11(6):495-500 (1998).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Makras et al., "Medical treatment of Hypercalcaemia," Hormones. 8(2):83-95 (2009).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Mather, "Establishment and characterization of two distinct mouse testicular epithelial cell lines," Biol Reprod. 23(1):243-52 (1980).
Mathijssen, "Guideline for care of patients with the diagnoses of craniosynostosis: working group on craniosynostosis," J Craniofac Surg. 26(6):1735-807 (2015).

Matsumoto et al., "Rescue of severe infantile hypophosphatasia mice by AAV-mediated sustained expression of soluble alkaline phosphatase," Hum Gene Ther. 22(11):1355-64 (2011).
Mayer, "Chapter 4: Immunoglobulins: Structure and Function," *Microbiology and Immunology On-line*, University of South Carolina School of Medicine, <pathmicro.med.sc.edu/mayer/IgStruct2000.htm> (2009) (12 pages).
McKiernan et al., "Clinical and radiographic findings in adults with persistent hypophosphatasemia," J Bone Miner Res. 29(7):1651-60 (2014).
Mericq et al., "Regulation of fetal rat bone growth by C-type natriuretic peptide and cGMP," Pediatr Res. 47(2):189-193 (2000) (9 pages).
Merrill et al., "Bent bone dysplasia-FGFR2 type, a distinct skeletal disorder, has deficient canonical FGF signaling," Am J Hum Genet. 90(3):550-7 (2012).
Meyer, "Can biological calcification occur in the presence of pyrophosphate?" Arch Biochem Biophys. 231(1):1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Millán, *Mammalian Alkaline Phosphatases: From Biology to Applications in Medicine and Biotechnology*, Wiley-VCH Verlag GmbH & Co., Weinheim, Germany (2006) (324 pages).
Millán et al., "Alkaline phosphatase and hypophosphatasia," Calcif Tissue Int. 98(4):398-416 (2016).
Millán et al., "Enzyme replacement therapy for murine hypophosphatasia," J Bone Miner Res. 23(6):777-87 (2008).
Millán et al., "Hypophosphatasia—pathophysiology and treatment," available in PMC Sep. 22, 2014, published in final edited form as: Actual Osteol. 8(3):164-182 (2012) (21 pages).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Miyazawa et al., "Cyclic GMP-dependent protein kinase II plays a critical role in C-type natriuretic peptide-mediated endochondral ossification," Endocrinology. 143(9):3604-3610 (2002).
Mohn et al., "Hypophosphatasia in a child with widened anterior fontanelle: lessons learned from late diagnosis and incorrect treatment," Acta Paediatr. 100(7):e43-6 (2011).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Mornet, "Chapter 2: Molecular genetics of hypophosphatasia and phenotype-genotype correlations," Subcell Biochem. 76:25-43 (2015).
Mornet, "Hypophosphatasia," Best Pract Res Clin Rheumatol. 22(1):113-27 (2008).
Mornet, "Hypophosphatasia," Orphanet J Rare Dis. 2:(40) (2007) (8 pages).
Mornet et al., "A molecular-based estimation of the prevalence of hypophosphatasia in the European population," Ann Hum Genet. 75(3):439-45 (2011).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mornet, "Hypophosphatasia," Metabolism. 82:142-155; DOI: 10.1016/j.metabol.2017.08.013 (2018) (30 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "The tissue nonspecific alkaline phosphatase gene mutations database," <www.sesep.uvsq.fr/03_hypo_mutations.php>, last updated Nov. 28, 2019 (14 pages).

(56) References Cited

OTHER PUBLICATIONS

Morris et al., "Immunolocalization of alkaline phosphatase in osteoblasts and matrix vesicles of human fetal bone," Bone Miner. 19:287-298 (1992).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murgu et al., "Tracheobronchomalacia and excessive dynamic airway collapse," Respirology. 11(4):388-406 (2006).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal pancraniosynostosis in a patient with infantile hypophosphatasia," Cleft Palate Craniofac J. 53(6):741-4, doi: 10.1597/15-027 (2016).
Nakamura-Utsunomiya et al., "Clinical characteristics of perinatal lethal hypophosphatasia: a report of 6 cases," Clin Pediatr Endocrinol. 19(1):7-13 (2010).
Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).
NCBI Protein Database Accession No. AAC33858, <www.ncbi.nlm.nih.gov/protein/AAC33858>, retrieved Apr. 16, 2013 (1 page).
NCBI Protein Database Accession No. AAF64516, <www.ncbi.nlm.nih.gov/protein/AAF64516>, retrieved Apr. 16, 2013 (2 pages).
NCBI Protein Database Accession No. AAH21289, <www.ncbi.nlm.nih.gov/protein/AAH21289>, retrieved Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321:297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).

(56) References Cited

OTHER PUBLICATIONS

Office Action for U.S. Appl. No. 12/793,517, dated Aug. 16, 2010 (9 pages).
Office Action for U.S. Appl. No. 13/071,445, dated Feb. 6, 2012 (12 pages).
Office Action for U.S. Appl. No. 13/071,445, dated May 25, 2012 (14 pages).
Official Action and Translation for Japanese Application No. 2017-539393, dated Sep. 17, 2019 (14 pages).
Official Action and Translation for Japanese Application No. 2013-544989, dated Oct. 27, 2015 (6 pages).
Official Notification and Search Report for Eurasian Patent Application No. 201291138, dated Jul. 16, 2013 (3 pages).
Oginni et al., "Radiological and biochemical resolution of nutritional rickets with calcium," Arch Dis Child. 88(9):812-17 (2003).
Oikawa et al., "Enzyme replacement therapy on hypophosphatasia mouse model," J Inherit Metab Dis. 37(2):309-17 (2013).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Opperman, "Cranial sutures as intramembranous bone growth sites," Dev Dyn. 219(4):472-85 (2000).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:P9 (2013) (1 page).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).
Park et al., "Ex vivo assessment of contractility, fatigability and alternans in isolated skeletal muscles," J Vis Exp. 69:e4198 (2012) (8 page).
Park et al., "First Korean case of infantile hypophosphatasia with novel mutation in ALPL and literature review," Ann Clin Lab Sci. 46(3):302-7 (2016).
Park et al., "The Effect of Alendronate Loaded Biphasic Calcium Phosphate Scaffolds on Bone Regeneration in a Rat Tibial Defect Model," Int J Mol Sci. 16(11):26738-53 (2015) (17 pages).
Patti et al., "Critical residues in the ligand-binding site of the *Staphylococcus aureus* collagen-binding adhesin (MSCRAMM)," J Biol Chem. 270(20):12005-11 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).
Phillips et al., "Physical therapy management of infants and children with hypophosphatasia," Mol Genet Metab. 119(1-2):14-9 (2016).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Reginato et al., "Musculoskeletal manifestations of osteomalacia and rickets," Best Pract Res Clin Rheumatol. 17(6):1063-80 (2003).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, dated Apr. 22, 2016 (4 pages).
Reply to Final Office Action for U.S. Appl. No. 13/071,445, dated Oct. 25, 2012 (14 pages).
Reply to Final Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg, "Hypophosphatasia," Pediatr Endocrinol Rev. 10 Suppl 2:380-8 (2013) (Abstract only).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rodriguez et al., "Respiratory mechanics in an infant with perinatal lethal hypophosphatasia treated with human recombinant enzyme replacement therapy," Pediatr Pulmonol. 47(9):917-22 (2012).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Rottgers et al., "Outcomes of endoscopic suturectomy with post-operative helmet therapy in bilateral coronal craniosynostosis," J Neurosurg Pediatr. 18(3):281-6 (2016).
Rowe et al., "MEPE, a new gene expressed in bone marrow and tumors causing osteomalacia," Genomics. 67:54-68 (2000).
Rozovsky et al., "Cranial ultrasound as a first-line imaging examination for craniosynostosis," Pediatrics. 137(2):e20152230 (2016) (9 pages).
Russell et al., "Inorganic pyrophosphate in plasma in normal persons and in patients with hypophosphatasia, osteogenesis imperfecta, and other disorders of bone," J Clin Invest. 50:961-969 (1971).
Sabbagh et al., "Hypophosphatemia leads to rickets by impairing caspase-mediated apoptosis of hypertrophic chondrocytes," Proc Natl Acad Sci U S A. 102(27):9637-42 (2005).
Saglam et al., "Clinical and genetic findings of Turkish hypophosphatasia cases," J Clin Res Pediatr Endocrinol. 9(3):229-236 (2017).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Salih et al., "Identification of the phosphorylated sites of metabolically $^{32}$P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).

(56) References Cited

OTHER PUBLICATIONS

Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017) (1 page).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical, radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its usein the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
Sekido et al., "Novel drug delivery system to bone using acidic oligopeptide: pharmacokinetic characteristics and pharmacological potential," J Drug Target. 9(2):111-21 (2001).
"Sequence 4," SCORE Search Results for U.S. Appl. No. 12/599,679, retrieved Nov. 17, 2018 (2 pages).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Shapiro et al., "Hypophosphatasia in adults: clinical assessment and treatment considerations," J Bone Miner Res. 32(10):1977-1980 (2017).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of Hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Silver et al., "Pulmonary hypoplasia in neonatal hypophosphatasia," Pediatr Pathol. 8(5):483-93 (1988) (12 pages).
Simm et al., "Successful use of enzyme replacement therapy in infantile hypophosphatasia," J Paediatr Child Health. 53(9):925-926 (2017).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Siris et al., "Paget's disease of bone," Trends Endocrinol Metab. 2(6):207-12 (1991).

Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017) (6 pages).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).
Srinivas et al., "Assessment of dose proportionality, absolute bioavailability, and immunogenicity response of CTLA4lg (BMS-188667), a novel immunosuppressive agent, following subcutaneous and intravenous administration to rats," Pharm Res. 14(7): 911-6 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).
Stoll et al., "Severe hypophosphatasia due to mutations in the tissue-nonspecific alkaline phosphatase (TNSALP) gene," Genet Couns. 13(3):289-95 (2002).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223:1-6 (1996).
Sugano et al., "Successful gene therapy in utero for lethal murine hypophosphatasia," Hum Gene Ther. 23(4):399-406 (2012).
Supplementary European Search Report for European Patent Application No. 11853820.6, dated Mar. 25, 2014 (3 pages).
Supplementary European Search Report for European Application No. 05739065, dated Dec. 2, 2008 (3 pages).
Symersky et al., "Structure of the collagen-binding domain from a *Staphylococcus aureus* adhesin," Nat Struct Biol. 4(10):833-838 (1997).
Takahashi et al., "Parental serum alkaline phosphatase activity as an auxiliary tool for prenatal diagnosis of hypophosphatasia," Prenat Diagn. 37(5):491-6 (2017).
Takano et al., "Molecular evolution of shark C-type natriuretic peptides," Zoolog Sci. 11:451-454 (1994).
Taketani et al., Chapter 9: Hypophosphatasia. *Human Pathobiochemistry*. T. Oohashi et al. (eds.), 91-100 (2019).
Taketani et al., "Clinical and genetic aspects of hypophosphatasia in Japanese patients," Arch Dis Child. 99(3):211-5 (2014) (6 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Takinami et al., "The mutant (F310L and V365I) tissue-nonspecific alkaline phosphatase gene from hypophosphatasia," J Med Dent Sci. 51(1):67-74 (2004).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tenorio et al., "Molecular and clinical analysis of ALPL in a cohort of patients with suspicion of hypophosphatasia," Am J Med Genet A. 173(3):601-10 (2017).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).

(56) References Cited

OTHER PUBLICATIONS

Tokumaru et al., "Skull base and calvarial deformities: association with intracranial changes in craniofacial syndromes," Am J Neuroradiol. 17(4):619-30 (1996).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <abstracts.eurospe.org/hrp/0086/hrp0086FC2.5.htm> (2016) (4 pages).
Tsiantouli et al., "Hypophosphatasia," Rev Med Suisse. 13(559):855-8 (2017) (Article in French) (English Abstract Included).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
UniProtKB Accession No. P01857. Retrieved May 2, 2018 (13 pages).
UniProtKB Accession No. P05186. Retrieved May 2, 2018 (19 pages).
Urlaub et al., "Deletion of the diploid dihydrofolate reductase locus from cultured mammalian cells," Cell. 33:405-412 (1983).
Urlaub et al., "Isolation of Chinese hamster cell mutants deficient in dihydrofolate reductase activity," Proc Natl Acad Sci U S A. 77(7):4216-20 (1980).
"View of NCT02235493 on Nov. 19, 2015," ClinicalTrials.gov archive, updated Nov. 19, 2015, retrieved Jan. 27, 2017 (4 pages).
Wang et al., "A mouse model for achondroplasia produced by targeting fibroblast growth factor receptor 3," Proc Natl Acad Sci USA. 96:4455-4460 (1999).
Wang et al., "Current concepts in odontohypophosphatasia form of hypophosphatasia and report of two cases," BMC Oral Health. 16(1):70 (2016) (8 pages).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86:134-140 (2005).
Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).
Waymire et al., "Mice lacking tissue non-specific alkaline phosphatase die from seizures due to defective metabolism of vitamin B-6," Nat Genet. 11(1):45-51 (1995).
Weber et al., "Burden of disease in adult patients with hypophosphatasia: Results from two patient-reported surveys," Metabolism. 65(10):1522-30 (2016).
Weber et al., "Burden of disease in children with hypophosphatasia: results from patient-reported surveys," 7th International Conference on Children's Bone Health, Jun. 27-30, Salzburg, Austria. *Bone Abstracts.* 4: P119 (2015) (3 pages).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85:7666-7669 (1988).
Weiss et al., "Isolation and characterization of a cDNA encoding a human liver/bone/kidney-type alkaline phosphatase," Proc Natl Acad Sci USA. 83(19):7182-6 (1986) (6 pages).

Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte, Chapter 18: Heritable Forms of Rickets and Osteomalacia. *Connective Tissue and Its Heritable Disorders.* Wiley-Liss, Inc., eds. R.M. Royce and B. Steinmann, 765-87 (2002).
Whyte, Chapter 22: Hypophosphatasia, *Genetics of Bone Biology and Skeletal Disease.* Rajesh V. Thakker, Michael P. Whyte, John A. Eisman and Takashi Igarashi (eds.), 337-360 (2013).
Whyte, Chapter 73: Hypophosphatasia: Nature's Window on Alkaline Phosphatase Function in Humans, *Principles of Bone Biology, vol. 1, Third Edition.* John P. Bilezikian, Lawrence G. Raisz and T. John Martin (eds.), 1573-98 (2008).
Whyte, Chapter 207: Hypophosphatasia. *The Online Metabolic and Molecular Bases for Inherited Disease.* McGraw-Hill Book Company, Valle et al. (eds.) (2001) (41 pages).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte, "Hypophosphatasia and the role of alkaline phosphatase in skeletal mineralization," Endocr Rev. 15(4):439-461 (1994).
Whyte, "Hypophosphatasia: enzyme replacement therapy brings new opportunities and new challenges," J Bone Miner Res. 32(4):667-675 (2017).
Whyte, "Physiological role of alkaline phosphatase explored in hypophosphatasia," Ann N Y Acad Sci. 1192:190-200 (2010).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Whyte et al., "Adult hypophosphatasia treated with teriparatide," J Clin Endocrinol Metab. 92(4):1203-8 (2007).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Whyte et al., "Asfotase alfa therapy for children with hypophosphatasia," JCI Insight. 1(9):e85971 (2016) (11 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Asfotase alfa treatment improves survival for perinatal and infantile hypophosphatasia," J Clin Endocrinol Metab. 101(1):334-42 (2016) (17 pages).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012) (1 page).
Whyte et al., "Hypophosphatasia (HPP) in Children: Enzyme Replacement Therapy (EzRT) Using Bone-Targeted, Tissue-Nonspecific

(56) References Cited

OTHER PUBLICATIONS

Alkaline Phosphatase (TNSALP)," Ann Neurol. 68(Suppl 14):S70 Abstract WIP-28 (2010) (1 page).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Markedly increased circulating pyridoxal-5'-phosphate levels in hypophosphatasia," J Clin Invest. 76:752-756 (1985).
Whyte et al., "Marrow cell transplantation for infantile hypophosphatasia," J Bone Miner Res. 18(4):624-36 (2003).
Whyte et al., "Natural history of perinatal and infantile hypophosphatasia: a retrospective study," J Pediatr. 209:116-124.e4 (2019) (13 pages).
Whyte et al., "Rickets and osteomalacia," Medicine. 37(9):483-8 (2009).
Wickramasinghe et al., "A case of hypophosphatasia," Ceylon Med J. 48(3):94-5 (2003) (2 pages).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "A successful treatment with pyridoxal phosphate for West syndrome in hypophosphatasia," Pediatr Neurol. 30(3):216-8 (2004).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Yamamoto et al., "Prolonged survival and phenotypic correction of Akp2$^{-/-}$ hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86 (2004).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Zaleckas et al., "Diagnosis and treatment of craniosynostosis: Vilnius team experience," Acta Med Litu. 22(2):111-21 (2015).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
Abrams et al. "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Rodionova et al. "Hypophosphatasia in adults: clinical cases and literature review," Osteoporosis and Bone Diseases. 18(2):25-7 (2015) (4 pages).
Search Report and Translation for Russian Application No. 2018109368, dated Feb. 5, 2020 (4 pages).
Wang et al., "The effects of tissue-non-specific alkaline phosphatase gene therapy on craniosynostosis and craniofacial morphology in the FGFR2$^{C342Y/+}$ mouse model of Crouzon craniosynostosis," Orthod Craniofac Res. 18 Suppl. 1:196-206 (2015).

* cited by examiner

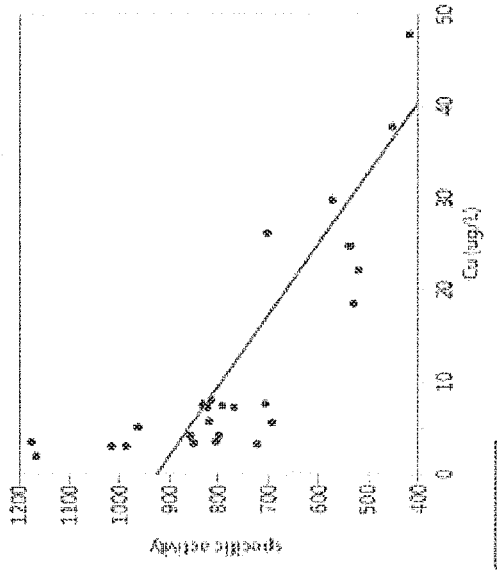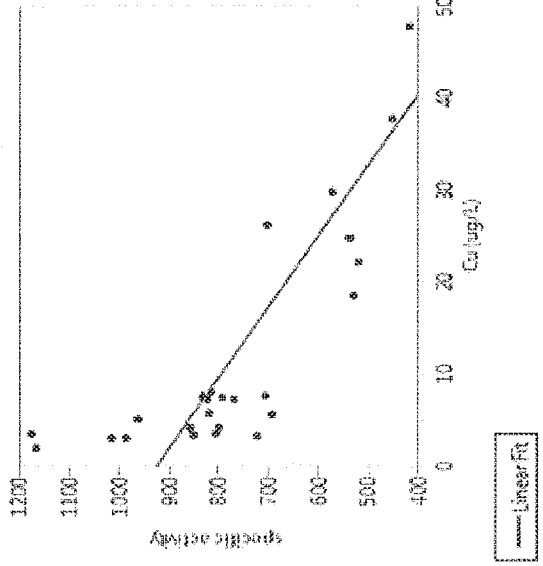
FIG. 3A          FIG. 3B
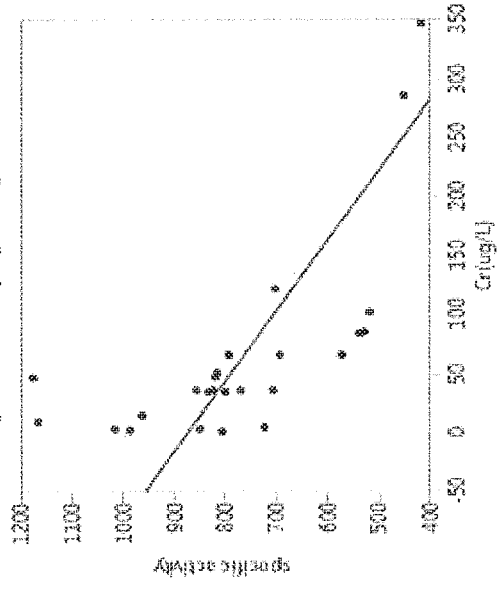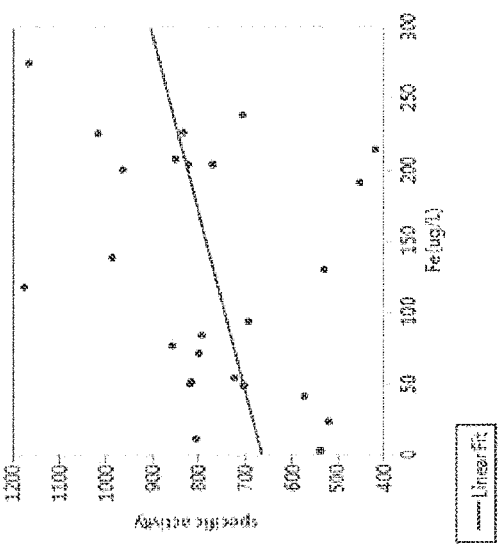
FIG. 3C

SEQUENCE LISTING

```
<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
```

```
               65                  70                  75                  80
          Ser Lys Thr Tyr Asn Thr Asn Ala Gln Val Pro Asp Ser Ala Gly Thr
                           85                  90                  95

Ala Thr Ala Tyr Leu Cys Gly Val Lys Ala Asn Glu Gly Thr Val Gly
                          100                 105                 110

Val Ser Ala Ala Thr Glu Arg Ser Arg Cys Asn Thr Thr Gln Gly Asn
                          115                 120                 125

Glu Val Thr Ser Ile Leu Arg Trp Ala Lys Asp Ala Gly Lys Ser Val
                      130                 135                 140

Gly Ile Val Thr Thr Thr Arg Val Asn His Ala Thr Pro Ser Ala Ala
          145                 150                 155                 160

Tyr Ala His Ser Ala Asp Arg Asp Trp Tyr Ser Asp Asn Glu Met Pro
                          165                 170                 175

Pro Glu Ala Leu Ser Gln Gly Cys Lys Asp Ile Ala Tyr Gln Leu Met
                          180                 185                 190

His Asn Ile Arg Asp Ile Asp Val Ile Met Gly Gly Gly Arg Lys Tyr
                      195                 200                 205

Met Tyr Pro Lys Asn Lys Thr Asp Val Glu Tyr Glu Ser Asp Glu Lys
                      210                 215                 220

Ala Arg Gly Thr Arg Leu Asp Gly Leu Asp Leu Val Asp Thr Trp Lys
          225                 230                 235                 240

Ser Phe Lys Pro Arg Tyr Lys His Ser His Phe Ile Trp Asn Arg Thr
                          245                 250                 255

Glu Leu Leu Thr Leu Asp Pro His Asn Val Asp Tyr Leu Leu Gly Leu
                      260                 265                 270

Phe Glu Pro Gly Asp Met Gln Tyr Glu Leu Asn Arg Asn Asn Val Thr
                      275                 280                 285

Asp Pro Ser Leu Ser Glu Met Val Val Ala Ile Gln Ile Leu Arg
                      290                 295                 300

Lys Asn Pro Lys Gly Phe Phe Leu Leu Val Glu Gly Gly Arg Ile Asp
          305                 310                 315                 320

His Gly His His Glu Gly Lys Ala Lys Gln Ala Leu His Glu Ala Val
                          325                 330                 335

Glu Met Asp Arg Ala Ile Gly Gln Ala Gly Ser Leu Thr Ser Ser Glu
                      340                 345                 350

Asp Thr Leu Thr Val Val Thr Ala Asp His Ser His Val Phe Thr Phe
                      355                 360                 365

Gly Gly Tyr Thr Pro Arg Gly Asn Ser Ile Phe Gly Leu Ala Pro Met
                      370                 375                 380

Leu Ser Asp Thr Asp Lys Lys Pro Phe Thr Ala Ile Leu Tyr Gly Asn
          385                 390                 395                 400

Gly Pro Gly Tyr Lys Val Val Gly Gly Glu Arg Glu Asn Val Ser Met
                          405                 410                 415

Val Asp Tyr Ala His Asn Asn Tyr Gln Ala Gln Ser Ala Val Pro Leu
                      420                 425                 430

Arg His Glu Thr His Gly Gly Glu Asp Val Ala Val Phe Ser Lys Gly
                      435                 440                 445

Pro Met Ala His Leu Leu His Gly Val His Glu Gln Asn Tyr Val Pro
                      450                 455                 460

His Val Met Ala Tyr Ala Ala Cys Ile Gly Ala Asn Leu Gly His Cys
          465                 470                 475                 480

Ala Pro Ala Ser Ser Leu Lys Asp Lys Thr His Thr Cys Pro Pro Cys
                          485                 490                 495
```

```
Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
530             535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Glu Glu
            610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
                660                 665                 670

Leu Tyr Ser Lys Leu Thr Val Asp Lys Ser Arg Trp Gln Gln Gly Asn
                675                 680                 685

Val Phe Ser Cys Ser Val Met His Glu Ala Leu His Asn His Tyr Thr
            690                 695                 700

Gln Lys Ser Leu Ser Leu Ser Pro Gly Lys Asp Ile Asp Asp Asp Asp
705                 710                 715                 720

Asp Asp Asp Asp Asp Asp
                725
```

METHOD OF PRODUCING ALKALINE PHOSPHATASE

SEQUENCE LISTING

The amino acid sequences listed in the accompanying sequence listing are shown using standard three-letter code for amino acids, as defined in 37 C.F.R. 1.822. The Sequence Listing is submitted as an ASCII text file, created on Jun. 5, 2017, about 10 KB, which is incorporated by reference herein.

BACKGROUND

Hypophosphatasia (HPP) is a life-threatening, genetic, and ultra-rare metabolic disorder that results in a failure to produce functional tissue nonspecific alkaline phosphatase (TNSALP). It leads to the accumulation of unmineralized bone matrix (e.g. rickets, osteomalacia), characterized by hypo-mineralization of bones and teeth. When growing bone does not mineralize properly, impairment of growth disfigures joints and bones. This result in turn impacts motor performance, respiratory function, and may even lead to death. Different forms of HPP include perinatal, infantile, juvenile, and adult HPP. Recently, six clinical forms have been defined, most based upon age at symptom onset, including perinatal, benign prenatal, infantile, juvenile, adult, and odonto-HPP. Asfotase alfa is an investigational, first-in-class targeted enzyme replacement therapy designed to address defective endogenous TNSALP levels. For treating HPP with TNSALP, see Whyte et al., 2012 *N Engl J Med.* 366:904-13.

Asfotase alfa is a soluble fusion glycoprotein comprised of the catalytic domain of human TNSALP, a human immunoglobulin G1 Fc domain and a deca-aspartate peptide (i.e., $D_{10}$) used as a bone-targeting domain. In vitro, asfotase alfa binds with a greater affinity to hydroxyapatite than does soluble TNSALP lacking the deca-aspartate peptide thus allowing the TNSALP moiety of asfotase alfa to efficiently degrade excess local inorganic pyrophosphate (PPi) and restore normal mineralization. Pyrophosphate hydrolysis promotes bone mineralization and its effects are similar among the species evaluated in nonclinical studies. Efficacy studies were conducted in a mouse model of HPP ($Akp2^{-/-}$ mice). The $Akp2^{-/-}$ mouse model, created by inactivating the TNSALP gene (Narisawa et al., 1997 *Dev Dyn.* 208:432-46), shares many common features of the human condition, including accumulation of unmineralized bone matrix.

BRIEF SUMMARY

Disclosed herein are methods for maintaining, preserving, modulating and/or improving the enzymatic activity of a recombinant protein, such as alkaline phosphatases (e.g., asfotase alfa) produced by culture cells. Such alkaline phosphatases (e.g., asfotase alfa) are suited for use in therapy, for example, for treatment of conditions associated with decreased alkaline phosphatase protein levels and/or function (e.g., insufficient cleavage of inorganic pyrophosphate (PPi)) in a subject, for example, a human subject.

In one aspect, the present disclosure provides a method for improving the enzymatic activity of a recombinant alkaline phosphatase (e.g., asfotase alfa) produced by culture cells. In some embodiments, such method comprises minimizing the concentration of at least one metal ion in at least one buffer and/or solution used in at least one step of downstream processes for the produced alkaline phosphatase (e.g., asfotase alfa). Such at least one metal ion may include, e.g., Nickel (Ni), Copper (Cu), Cobalt (Co), Chromium (Cr), Molybdenum (Mo), Manganese (Mn), Gold (Au), Calcium (Ca), Germanium (Ge), Chromium (Cr), Magnesium (Mg), Rhodium (Rh), Antimony (Sb), Platinum (Pt), Ruthenium (Ru), Scandium (Sc), Palladium (Pd), Vanadium (V), and Zirconium (Zr). In one embodiment, the present disclosure presents a method for improving the enzymatic activity of a recombinant alkaline phosphatase (e.g., asfotase alfa) produced by culture cells, comprising minimizing the concentration of at least one metal ion selected from the group consisting of Nickel (Ni), Copper (Cu), Cobalt (Co), Chromium (Cr), Molybdenum (Mo), and Manganese (Mn) in at least one buffer and/or solution used in at least one step of downstream processes for the produced alkaline phosphatase (e.g., asfotase alfa). In one embodiment, such at least one metal ion is selected from the group consisting of Nickel (Ni), Copper (Cu), and Cobalt (Co). In some embodiments, the method described herein comprises increasing the concentration of at least one metal ion in at least one buffer and/or solution used in at least one step of downstream processes for the produced alkaline phosphatase (e.g., asfotase alfa). Such at least one metal ion may include, e.g., Zinc (Zn), Silicon (Si), Silver (Ag), Aluminum (Al), Arsenic (As), Boron (B), Barium (Ba), Cadmium (Cd), Indium (In), Potassium (K), iron (Fe), Iridium (Ir), Niobium (Nb), Mercury (Hg), Lead (Pb), Tin (Sn), Titanium (Ti), Thallium (Tl), and Yttrium (Y). In one embodiment, such at least one metal ion is Zinc (Zn) or Silicon (Si).

In one aspect, the present disclosure provides a method of producing recombinant alkaline phosphatase comprising:
  (i) culturing an alkaline phosphatase in a recombinant cell culture;
  (ii) obtaining a preparation of recombinant alkaline phosphatase from the cell culture; and
  (iii) minimizing in the preparation a concentration of at least one metal ion selected from the group consisting of: Nickel (Ni), Cobalt (Co), Copper (Cu), Manganese (Mn), Chromium (Cr), and Molybdenum (Mo).

In another aspect, the present disclosure provides a method of producing recombinant alkaline phosphatase comprising:
  (i) culturing an alkaline phosphatase in a recombinant cell culture;
  (ii) obtaining a preparation of recombinant alkaline phosphatase from the cell culture; and
  (iii) increasing in the preparation a concentration of at least one metal ion selected from the group consisting of: Zinc (Zn) and Silicon (Si).

In another aspect, the present disclosure provides a method of producing recombinant alkaline phosphatase comprising:
  (i) culturing an alkaline phosphatase in a recombinant cell culture;
  (ii) obtaining a preparation of recombinant alkaline phosphatase from the cell culture;
  (iii) minimizing in the preparation a concentration of at least one metal ion selected from the group consisting of: Nickel (Ni), Cobalt (Co), Copper (Cu), Manganese (Mn), Chromium (Cr), and Molybdenum (Mo); and
  (iv) separating the recombinant alkaline phosphatase from the remainder of the preparation by Hydrophobic Interaction Chromatography (HIC).

In another aspect, the present disclosure provides a method of producing recombinant alkaline phosphatase comprising:
  (i) culturing an alkaline phosphatase in a recombinant cell culture;
  (ii) obtaining a preparation of recombinant alkaline phosphatase from the cell culture;
  (iii) increasing in the preparation a concentration of at least one metal ion selected from the group consisting of: Zinc (Zn) and Silicon (Si); and
  (iv) separating the recombinant alkaline phosphatase from the remainder of the preparation by Hydrophobic Interaction Chromatography (HIC).

In another aspect, the present disclosure provides a method of producing recombinant alkaline phosphatase comprising:
  (i) culturing an alkaline phosphatase in a recombinant cell culture;
  (ii) obtaining a preparation of recombinant alkaline phosphatase from the cell culture;
  (iii) minimizing in the preparation a concentration of at least one metal ion selected from the group consisting of: Nickel (Ni), Cobalt (Co), Copper (Cu), Manganese (Mn), Chromium (Cr), and Molybdenum (Mo);
  (iv) increasing in the preparation a concentration of at least one metal ion selected from the group consisting of: Zinc (Zn) and Silicon (Si); and
  (v) separating the recombinant alkaline phosphatase from the remainder of the preparation by Hydrophobic Interaction Chromatography (HIC).

In another aspect, the present disclosure provides a method of producing purified recombinant alkaline phosphatase comprising:
  (i) culturing an alkaline phosphatase in a recombinant cell culture;
  (ii) obtaining a preparation of recombinant alkaline phosphatase from the cell culture;
  (iii) minimizing in the preparation a concentration of at least one metal ion selected from the group consisting of: Nickel (Ni), Cobalt (Co), Copper (Cu), and Manganese (Mn); and
  (iv) separating the recombinant alkaline phosphatase from the reminder of the preparation by Hydrophobic Interaction Chromatography (HIC).

In another aspect, the present disclosure provides a method of producing purified recombinant alkaline phosphatase comprising:
  (i) culturing an alkaline phosphatase in a recombinant cell culture;
  (ii) obtaining a preparation of recombinant alkaline phosphatase from the cell culture;
  (iii) minimizing in the preparation a concentration of at least one metal ion selected from the group consisting of: Nickel (Ni), Cobalt (Co), Copper (Cu), and Manganese (Mn);
  (iv) increasing in the preparation a concentration of at least one metal ion selected from the group consisting of: Zinc (Zn) and Silicon (Si); and
  (v) separating the recombinant alkaline phosphatase from the remainder of the preparation by Hydrophobic Interaction Chromatography (HIC).

In some embodiments, the steps used for producing, purifying, and/or separating the alkaline phosphatase from the culture cells, as disclosed herein, further comprise at least one of steps selected from the group consisting of: a harvest clarification process (or a similar process to remove the intact cells and cell debris from the cell culture), an ultrafiltration (UF) process (or a similar process to concentrate the produced alkaline phosphatase), a diafiltration (DF) process (or a similar process to change or dilute the buffer comprising the produced alkaline phosphatase from previous processes), a viral inactivation process (or a similar process to inactivate or remove viral particles), an affinity capture process (or any one of chromatography methods to capture the produced alkaline phosphatase and separate it from the rest of the buffer/solution components), a formulation process and a bulk fill process. In one embodiment, the steps for producing, purifying, and/or separating the alkaline phosphatase from the culture cells, as disclosed herein, comprise at least a harvest clarification process (or a similar process to remove the intact cells and cell debris from the cell culture), a post-harvest ultrafiltration (UF) process (or a similar process to concentrate the produced alkaline phosphatase), a post-harvest diafiltration (DF) process (or a similar process to change or dilute the buffer comprising the produced alkaline phosphatase from previous processes), a solvent/detergent viral inactivation process (or a similar process to chemically inactivate viral particles), an intermediate purification process (such as hydrophobic interaction chromatography (HIC) or any one of chromatography methods to capture the produced alkaline phosphatase and separate it from the rest of the buffer/solution components), a post-HIC UF/DF process (or a similar process to concentrate and/or buffer exchange for the produced alkaline phosphatase), a viral reduction filtration process (or a similar process to further remove any viral particles or other impurities or contaminants); a mixed-mode chromatography (such as CAPTO® Adhere agarose chromatography, or a similar process to further purify and/or concentrate the produced alkaline phosphatase), a formulation process and a bulk fill process. In one embodiment, the separating step of the method provided herein further comprises at least one of harvest clarification, ultrafiltration, diafiltration, viral inactivation, affinity capture, HIC chromatography, mixed-mode chromatography and combinations thereof.

In some embodiments, the method described herein further comprises measuring recombinant alkaline phosphatase activity, wherein the recombinant alkaline phosphatase activity increases after the separating step described herein, compared to the activity in the preparation prior to step (iii). For example, the activity may be measured by at least one method selected from: a pNPP-based alkaline phosphatase enzymatic assay and an inorganic pyrophosphate (PPi) hydrolysis assay, or other routine methods known in the art. The activity may be shown using various routine parameters known in the art. For example, at least one of the recombinant alkaline phosphatase $K_{cat}$ and $K_m$ values may increase in an inorganic pyrophosphate (PPi) hydrolysis assay described herein.

In some embodiments, the method described herein further comprises:
  providing at least one solution selected from the group consisting of: load dilution solution, pre-equilibration solution, equilibration solution, wash solution, and elution solution to the separating by Hydrophobic Interaction Chromatography (HIC); and
  (a) minimizing in said at least one HIC solution the concentration of at least one metal ion selected from the group consisting of: Nickel (Ni), Cobalt (Co), Copper (Cu), Manganese (Mn), Chromium (Cr), and Molybdenum (Mo);
  (b) increasing in said at least one HIC solution the concentration of at least one metal ion selected from the group consisting of: Zinc (Zn) and Silicon (Si); or
  (c) both (a) and (b).

In some embodiments, the method described herein further comprises: providing at least one solution selected from the group consisting of: load dilution solution, pre-equilibration solution, wash solution(s), equilibration solution, wash solution(s), and elution solution to the separating by Hydrophobic Interaction Chromatography (HIC); and (a) minimizing in said at least one HIC solution the concentration of at least one metal ion selected from the group consisting of: Nickel (Ni), Cobalt (Co), Copper (Cu), and Manganese (Mn);

(b) increasing in said at least one HIC solution the concentration of at least one metal ion selected from the group consisting of: Zinc (Zn) and Silicon (Si); or (c) both (a) and (b).

In some embodiments, the steps used for purifying the produced alkaline phosphatase from the culture cells, as disclosed herein, comprise an affinity capture process. In one embodiment, the affinity capture process is a chromatography process. Such chromatography process may involve, at least, a Hydrophobic Interaction Chromatography (HIC), a Protein A chromatography, or a CAPTO® Adhere mixed-mode agaroase chromatography. In one embodiment, the chromatography process is a Hydrophobic Interaction Chromatography (HIC) process.

In some embodiments, the described method comprises minimizing the concentration of at least one metal ion selected from the group consisting of: Cobalt (Co), Chromium (Cr), Copper (Cu), Molybdenum (Mo), Manganese (Mn), and Nickel (Ni); (b) increasing the concentration of at least one metal ion selected from the group consisting of: Silicon (Si) and Zinc (Zn); or (c) both (a) in at least one buffer and/or solution used in each step of downstream processes, as disclosed herein. Some exemplary buffers/solutions include the load dilution buffer, the pre-equilibration buffer, the equilibration buffer, the wash buffer(s), the elution buffer, the strip buffer and the storage buffer. The buffers/solutions described herein may contain ammonium sulfate (AMS), sodium sulfate, other ammonium salts, and/or other sulfate salts. In one embodiment, the buffers/solutions described herein comprise ammonium sulfate (AMS), particularly from about 0.2M to about 3M. In one embodiment, the buffers/solutions described herein comprise sodium sulfate, particularly from about 0.2M to about 1.5M. In one embodiment, the buffers/solutions described herein comprise sodium chloride (NaCl), particularly from about 0.5M to about 3M. It was discovered that AMS in the buffers/solutions used in the downstream processes rendered the alkaline phosphatase activity more sensitive to the metal impact described herein. On the contrary, changing metal ion concentrations in buffers/solutions containing sodium sulfate resulted in minor changes in the alkaline phosphatase activity.

In one embodiment, the method described herein comprises minimizing or reducing the concentration of at least one metal ion selected from the group consisting of: Nickel (Ni), Copper (Cu), Cobalt (Co), Chromium (Cr), Molybdenum (Mo), and Manganese (Mn) in at least one of the buffers or solutions used for purifying the produced alkaline phosphatase from the culture cells. In another embodiment, the method described herein comprises minimizing the concentration of at least one metal ion selected from the group consisting of: Nickel (Ni), Cobalt (Co), Copper (Cu), and Manganese (Mn) in at least one of the buffers or solutions used for purifying the produced alkaline phosphatase from the culture cells. In yet another embodiment, the method described herein comprises increasing the concentration of at least one metal ion selected from the group consisting of: Zinc (Zn) and Silicon (Si) in at least one of the buffers or solutions used for purifying the produced alkaline phosphatase from the culture cells.

While not being limited by this theory, the rationale of minimizing or reducing the concentration of certain metal ions and/or increasing the concentration of other certain metal ions is to facilitate the enzyme stability and/or activity through interaction with zinc ions. For example, for those metal ions having potential negative impact on the activity (usually represented by its specific activity) of the produced alkaline phosphatase, such as Ni, Cu, Co, Mn, and others disclosed herein, minimizing the concentration of such metal ions may help to prevent the disruption of Zn-enzyme interaction by those metal ions, resulting in stabilizing the alkaline phosphatase activity. Similarly, for those metal ions having potential positive impact on the activity (usually represented by its specific activity) of the produced alkaline phosphatase, such as Zn and others disclosed herein, increasing the concentration of such metal ions may increase the metal-enzyme molar ratio and thus result in stabilizing/increasing the alkaline phosphatase activity. Thus, the methods provided by the present disclosure are targeted to minimize the concentration of metal ions having potential negative impact on the alkaline phosphatase activity, or increasing the concentration of metal ions having potential positive impact on the alkaline phosphatase activity, or combining both strategies. In some embodiments, the concentration of the metal ions having potential negative impact on the alkaline phosphatase activity is decreased below a certain level, measured by their absolute amount (e.g., their concentrations) or the molar ratio of these metal ions to the zinc content in the buffer/solution. In some embodiments, the concentration of the metal ions having potential positive impact on the alkaline phosphatase activity is increased beyond a certain level, measured by their absolute amount (e.g., their concentrations) or the molar ratio of these metal ions to the zinc content in the buffer/solution. For such supplementation scenarios, any metal ions (i.e., those having potential positive impact on the alkaline phosphatase activity) may be supplemented in any form of salts or other forms known in common knowledge. For example, zinc may be supplemented in at least one form of: zinc sulfate ($ZnSO_4$), zinc sulfate heptahydrate, zinc phosphate ($Zn_3(PO_4)_2$), zinc nitrate ($Zn(NO_3)_2$), zinc chlorate ($Zn(ClO_3)_2$), zinc molybdate ($ZnMoO_4$), zinc chromate ($ZnCrO_4$), zinc arsenite ($Zn(AsO_2)_2$), zinc arsenate octahydrate ($Zn(AsO_4)_2 \cdot 8H_2O$), and any forms of organic compounds (such as zinc acetate $Zn(O_2CCH_3)_2$). In one embodiment, zinc sulfate is supplemented. In another embodiment, zinc sulfate heptahydrate is supplemented. In the present disclosure, zinc may be added to reach a certain concentration or a desired zinc molar ratio.

In some embodiments, the method provided by the present disclosure comprises minimizing or reducing the concentration of Nickel (Ni) in at least one buffer or solution described herein to less than about 10, 9, 8, 7, 6, 5, 4, 3, 2, 1, 0.9, 0.8, 0.7, 0.6, 0.5, 0.4, 0.3, 0.2, 0.1, 0.05, or less, ppm. In one embodiment, the concentration of Nickel (Ni) is minimized or reduced to less than about 5 ppm. In one embodiment, the concentration of Nickel (Ni) is minimized or reduced to less than about 3 ppm. In one embodiment, the concentration of Nickel (Ni) is minimized or reduced to less than about 2 ppm. In one embodiment, the concentration of Nickel (Ni) is minimized or reduced to less than about 1 ppm. In one embodiment, the concentration of Nickel (Ni) is minimized or reduced to less than about 2.33 ppm. In another embodiment, the concentration of Nickel (Ni) is minimized or reduced to less than about 1.87 ppm. In another embodiment, the concentration of Nickel (Ni) is minimized or reduced to less than about 0.7 ppm.

In some embodiments, the method provided by the present disclosure comprises minimizing or reducing the concentration of Cobalt (Co) in at least one buffer or solution described herein to less than about 10, 9, 8, 7, 6, 5, 4, 3, 2, 1, 0.9, 0.8, 0.7, 0.6, 0.5, 0.4, 0.3, 0.2, 0.1, 0.05, or less, ppm. In one embodiment, the concentration of Cobalt (Co) is minimized or reduced to less than about 5 ppm. In one embodiment, the concentration of Cobalt (Co) is minimized or reduced to less than about 3 ppm. In one embodiment, the concentration of Cobalt (Co) is minimized or reduced to less than about 2 ppm. In one embodiment, the concentration of Cobalt (Co) is minimized or reduced to less than about 1 ppm. In one embodiment, the concentration of Cobalt (Co) is minimized or reduced to less than about 0.5 ppm. In one embodiment, the concentration of Cobalt (Co) is minimized or reduced to less than about 0.30 ppm. In one embodiment, the concentration of Cobalt (Co) is minimized or reduced to less than about 0.1 ppm. In one embodiment, the concentration of Cobalt (Co) is minimized or reduced to less than about 0.30 ppm. In another embodiment, the concentration of Cobalt (Co) is minimized or reduced to less than about 0.24 ppm. In another embodiment, the concentration of Cobalt (Co) is minimized or reduced to less than about 0.09 ppm.

In some embodiments, the method provided by the present disclosure comprises minimizing or reducing the concentration of Copper (Cu) in at least one buffer or solution described herein to less than about 50, 45, 40, 35, 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, or less, ppm. In one embodiment, the concentration of Copper (Cu) is minimized or reduced to less than about 50 ppm. In one embodiment, the concentration of Copper (Cu) is minimized or reduced to less than about 30 ppm. In one embodiment, the concentration of Copper (Cu) is minimized or reduced to less than about 20 ppm. In one embodiment, the concentration of Copper (Cu) is minimized or reduced to less than about 10 ppm. In one embodiment, the concentration of Copper (Cu) is minimized or reduced to less than about 8 ppm. In one embodiment, the concentration of Copper (Cu) is minimized or reduced to less than about 5 ppm. In one embodiment, the concentration of Copper (Cu) is minimized or reduced to less than about 1 ppm. In one embodiment, the concentration of Copper (Cu) is minimized or reduced to less than about 24.82 ppm. In another embodiment, the concentration of Copper (Cu) is minimized or reduced to less than about 19.86 ppm. In another embodiment, the concentration of Copper (Cu) is minimized or reduced to less than about 7.45 ppm.

In some embodiments, the method provided by the present disclosure comprises minimizing or reducing the concentration of Manganese (Mn) in at least one buffer or solution described herein to less than about 50, 45, 40, 35, 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, or less, ppm. In one embodiment, the concentration of Manganese (Mn) is minimized or reduced to less than about 50 ppm. In one embodiment, the concentration of Manganese (Mn) is minimized or reduced to less than about 30 ppm. In one embodiment, the concentration of Manganese (Mn) is minimized or reduced to less than about 20 ppm. In one embodiment, the concentration of Manganese (Mn) is minimized or reduced to less than about 10 ppm. In one embodiment, the concentration of Manganese (Mn) is minimized or reduced to less than about 8 ppm. In embodiment, the concentration of Manganese (Mn) is minimized or reduced to less than about 5 ppm. In one embodiment, the concentration of Manganese (Mn) is minimized or reduced to less than about 1 ppm. In one embodiment, the concentration of Manganese (Mn) is minimized or reduced to less than about 9.13 ppm.

In some embodiments, the method provided by the present disclosure comprises minimizing or reducing the concentration of metal ions having potential negative impact on alkaline phosphatase activity in at least one buffer or solution described herein to be below a certain level measured by the metal ion/zinc molar ratio. For example, the concentration of Nickel (Ni) may be minimized or reduced so that the molar ratio of Nickel/Zinc is less than about 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, or less. In one embodiment, the concentration of Nickel (Ni) may be minimized or reduced so that the molar ratio of Nickel/Zinc is less than about 5. In one embodiment, the concentration of Nickel (Ni) may be minimized or reduced so that the molar ratio of Nickel/Zinc is less than about 3. In one embodiment, the concentration of Nickel (Ni) may be minimized or reduced so that the molar ratio of Nickel/Zinc is less than about 2. In one embodiment, the concentration of Nickel (Ni) may be minimized or reduced so that the molar ratio of Nickel/Zinc is less than about 1. In one embodiment, the concentration of Nickel (Ni) may be minimized or reduced so that the molar ratio of Nickel/Zinc is less than about 0.9. In one embodiment, the concentration of Nickel (Ni) may be minimized or reduced so that the molar ratio of Nickel/Zinc is less than about 0.8. In one embodiment, the concentration of Nickel (Ni) may be minimized or reduced so that the molar ratio of Nickel/Zinc is less than about 0.5. In one embodiment, the concentration of Nickel (Ni) may be minimized or reduced so that the molar ratio of Nickel/Zinc is less than about 1.90. In another embodiment, the concentration of Nickel (Ni) may be minimized or reduced so that the molar ratio of Nickel/Zinc is less than about 0.85.

In some embodiments, the concentration of Cobalt (Co) may be minimized or reduced so that the molar ratio of Cobalt/Zinc is less than about 30, 25, 15, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.005, or less. In one embodiment, the concentration of Cobalt (Co) may be minimized or reduced so that the molar ratio of Cobalt/Zinc is less than about 5. In one embodiment, the concentration of Cobalt (Co) may be minimized or reduced so that the molar ratio of Cobalt/Zinc is less than about 3. In one embodiment, the concentration of Cobalt (Co) may be minimized or reduced so that the molar ratio of Cobalt/Zinc is less than about 2. In one embodiment, the concentration of Cobalt (Co) may be minimized or reduced so that the molar ratio of Cobalt/Zinc is less than about 1. In one embodiment, the concentration of Cobalt (Co) may be minimized or reduced so that the molar ratio of Cobalt/Zinc is less than about 0.5. In one embodiment, the concentration of Cobalt (Co) may be minimized or reduced so that the molar ratio of Cobalt/Zinc is less than about 0.2. In one embodiment, the concentration of Cobalt (Co) may be minimized or reduced so that the molar ratio of Cobalt/Zinc is less than about 0.1. In one embodiment, the concentration of Cobalt (Co) may be minimized or reduced so that the molar ratio of Cobalt/Zinc is less than about 0.08. In one embodiment, the concentration of Cobalt (Co) may be minimized or reduced so that the molar ratio of Cobalt/Zinc is less than about 0.01. In one embodiment, the concentration of Cobalt (Co) may be minimized or reduced so that the molar ratio of Cobalt/Zinc is less than about 0.09. In another embodiment, the concentration of Cobalt (Co) may be minimized or reduced so that the molar ratio of Cobalt/Zinc is less than about 0.05.

In some embodiments, the concentration of Copper (Cu) may be minimized or reduced so that the molar ratio of Cobalt/Zinc is less than about 30, 25, 15, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.005, or less. In one embodiment, the concentration of Copper (Cu) may be minimized or reduced so that the molar ratio of Copper/Zinc is less than about 5. In one embodiment, the concentration of Copper (Cu) may be minimized or reduced so that the molar ratio of Copper/Zinc is less than about 3. In one embodiment, the concentration of Copper (Cu) may be minimized or reduced so that the molar ratio of Copper/Zinc is less than about 2. In one embodiment, the concentration of Copper (Cu) may be minimized or reduced so that the molar ratio of Copper/Zinc is less than about 1. In one embodiment, the concentration of Copper (Cu) may be minimized or reduced so that the molar ratio of Copper/Zinc is less than about 0.5. In one embodiment, the concentration of Copper (Cu) may be minimized or reduced so that the molar ratio of Cobalt/Zinc is less than about 0.2. In one embodiment, the concentration of Copper (Cu) may be minimized or reduced so that the molar ratio of Copper/Zinc is less than about 0.1. In one embodiment, the concentration of Copper (Cu) may be minimized or reduced so that the molar ratio of Copper/Zinc is less than about 0.05. In one embodiment, the concentration of Copper (Cu) may be minimized or reduced so that the molar ratio of Copper/Zinc is less than about 0.16. In another embodiment, the concentration of Copper (Cu) may be minimized or reduced so that the molar ratio of Copper/Zinc is less than about 0.09.

In some embodiments, the method provided by the present disclosure comprises increasing the concentration of metal ions having potential positive impact on alkaline phosphatase activity in at least one buffer or solution described herein to be above a certain level measured by the concentration of such metal ions and/or the metal ion/zinc molar ratio. Such metal ions may include, e.g., Zinc (Zn), Silicon (Si), and others disclosed herein. For example, the concentration of Zinc (Zn) may be increased by zinc supplementation so that the Zn concentration is more than about 1, 5, 10, 15, 20, 25, 30, 35, 40, 45, 50, 55, 60, 65, 70, 75, 80, 85, 90, 95, 100, 110, 120, 130, 140, 150, 200, 225, 250, 325, 350, 375, 400, 425, 450, 475, 500, 525, 550, 575, 600, 625, 650, 675, 700, 725, 750, 775, 800, 825, 850, 875, 900, 925, 950, 975, 1000, 1200, 1400, 1500, 1600, 1700, 1800, 2000, or more, ppm. In one embodiment, the zinc concentration is increased to at least about 550 ppm. In another embodiment, the Zinc concentration is increased to at least about 600 ppm. In another embodiment, the Zinc concentration is increased to at least about 680 ppm. In another embodiment, the Zinc concentration is increased to from about 550 to about 680 ppm. In the present disclosure, zinc ion may be supplemented in any form of zinc salts or other forms known in the art.

In various embodiments, the alkaline phosphatase disclosed herein includes any polypeptide having alkaline phosphatase functions, which may include any functions of alkaline phosphatase known in the art, such as enzymatic activity toward natural substrates including phosphoethanolamine (PEA), inorganic pyrophosphate (PPi) and pyridoxal 5'-phosphate (PLP). Such recombinant polypeptide may be any recombinant and/or fusion forms of soluble alkaline phosphatases (sALPs). For example, such sALPs may be fused to the full-length or fragment (e.g., the fragment crystallizable region (Fc)) of an immunoglobulin molecule. In some embodiments, the recombinant polypeptide comprises a structure of W-sALP-X-Fc-Y-$D_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n$ is a poly-aspartate, poly-glutamate, or combination thereof, wherein n=10 or 16; and said sALP is a soluble alkaline phosphatase. In one embodiment, n=10. In another embodiment, W and Z are absent from said polypeptide. In some embodiments, said Fc comprises a CH2 domain, a CH3 domain and a hinge region. In some embodiments, said Fc is a constant domain of an immunoglobulin selected from the group consisting of IgG-1, IgG-2, IgG-3, IgG-3 and IgG-4. In one embodiment, said Fc is a constant domain of an immunoglobulin IgG-1. In one particular embodiment, said Fc comprises the sequence as set forth in D488-K714 of SEQ ID NO:1.

In some embodiments, the alkaline phosphatase disclosed herein comprises the structure of W-sALP-X-Fc-Y-$D_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n$ is a poly-aspartate, poly-glutamate, or combination thereof, wherein n=10 or 16; and said sALP is a soluble alkaline phosphatase. Such sALP is capable of catalyzing the cleavage of at least one of phosphoethanolamine (PEA), inorganic pyrophosphate (PPi) and pyridoxal 5'-phosphate (PLP). In various embodiments, the sALP disclosed herein is capable of catalyzing the cleavage of inorganic pyrophosphate (PPi). Such sALP may comprise all amino acids of the active anchored form of alkaline phosphatase (ALP) without C-terminal glycolipid anchor (GPI). Such ALP may be at least one of tissue-non-specific alkaline phosphatase (TNALP), placental alkaline phosphatase (PALP), germ cell alkaline phosphatase (GCALP), and intestinal alkaline phosphatase (IAP), or their chimeric or fusion forms or variants disclosed herein. In one particular embodiment, the ALP comprises tissue-non-specific alkaline phosphatase (TNALP). In another embodiment, the sALP disclosed herein is encoded by a polynucleotide encoding a polypeptide comprising the sequence as set forth in L1-S485 of SEQ ID NO:1. In yet another embodiment, the sALP disclosed herein comprises the sequence as set forth in L1-S485 of SEQ ID NO:1.

In some embodiments, the alkaline phosphatase disclosed herein is encoded by a first polynucleotide which hybridizes under high stringency conditions to a second polynucleotide comparing the sequence completely complementary to a third polynucleotide encoding a polypeptide comprising the sequence as set forth in SEQ ID NO:1. Such high stringency conditions may comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for 5 minutes.

In one particular embodiment, the alkaline phosphatase disclosed herein is encoded by a polynucleotide encoding a polypeptide comprising the sequence as set forth in SEQ ID NO:1. In another embodiment, the alkaline phosphatase disclosed herein comprises the sequence as set forth in SEQ ID NO:1.

In some embodiments, the improved enzymatic activity of the produced alkaline phosphatase (e.g., asfotase alfa), by minimizing the concentration of metal ions having potential negative impact on activity or increasing the concentration of metal ions having potential positive impact on activity or both as described herein, may be measured by any known method. Such methods include, e.g., those in vitro and in vivo assays measuring the enzymatic activity of the produced alkaline phosphatase (e.g., asfotase alfa) to substrates of an alkaline phosphatase, such as phosphoethanolamine (PEA), inorganic pyrophosphate (PPi) and pyridoxal 5'-phosphate (PLP).

BRIEF DESCRIPTION OF THE DRAWINGS

In the appended drawings:

FIGS. 3A-3C are graphs showing the linear correlation between the concentration of metal ions Cr (FIG. 3A), Cu (FIG. 3B), and Fe (FIG. 3C) in the AMS used in the HIC step and the specific activity of the produced asfotase alfa in the final BDS. The specific activity in view of Cr was calculated to be equal to 875.03−1.67×[Cr], while $R^2=0.5$ and the p value<0.001. The specific activity in view of Cu was calculated to be equal to 926.73−12.96×[Cu], while $R^2=0.7$ and the p value<0.001. The specific activity in view of Fe was calculated to be equal to 666.69+0.80×[Fe], while $R^2=0.1$ and the p value=0.09.

HIC 587.24−88.99 (Mn/Zn molar ratio), while $R^2=0.55$.

Figure 14:
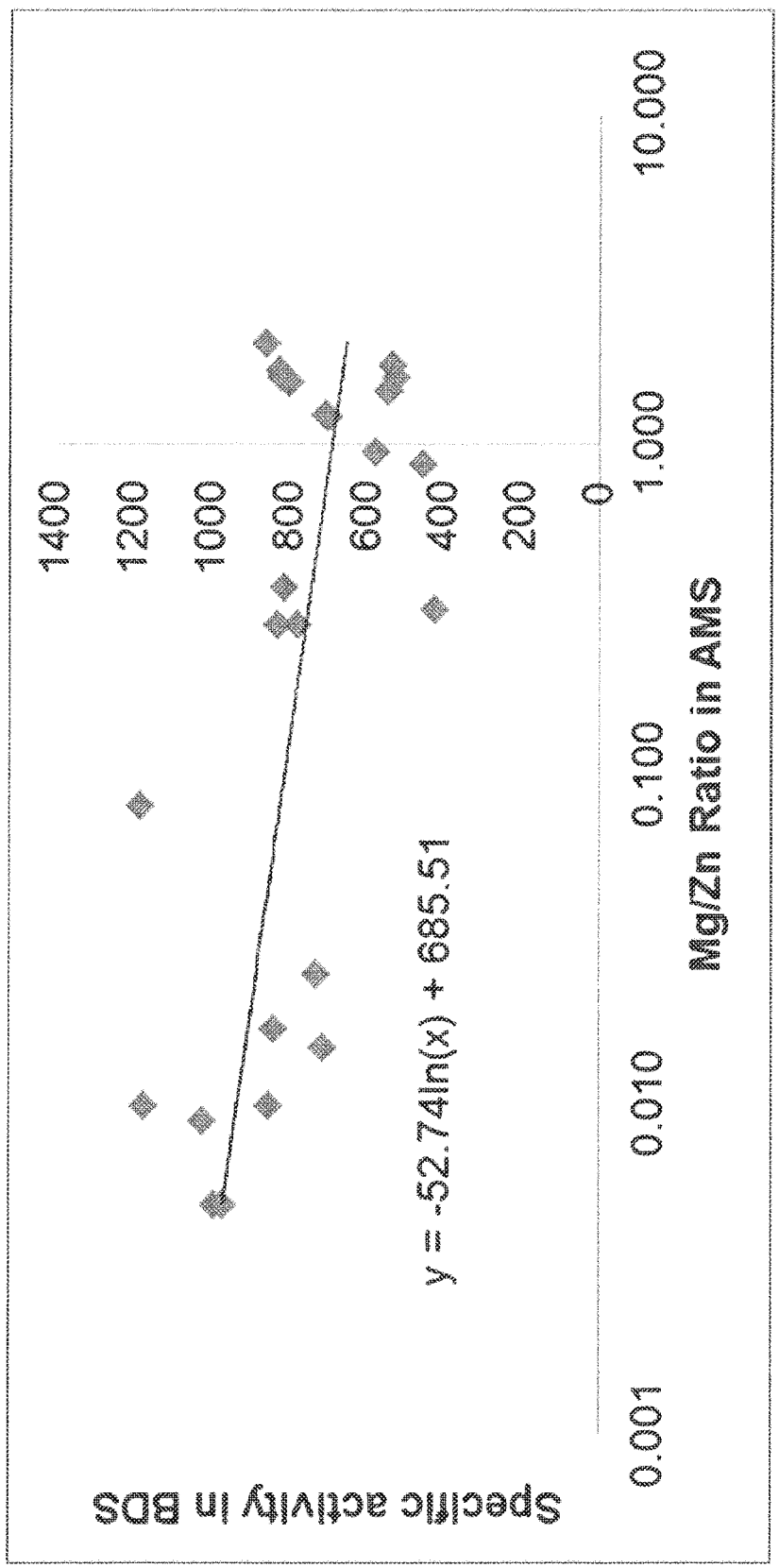

FIG. 14 is a graph showing the correlation between the Mg/Zn molar ratio in the AMS used in the HIC step and the specific activity in the final BDS. The specific activity was calculated to be equal to 685.51−52.74×ln (Mg/Zn molar ratio), while $R^2=0.34$.

Figure 15:
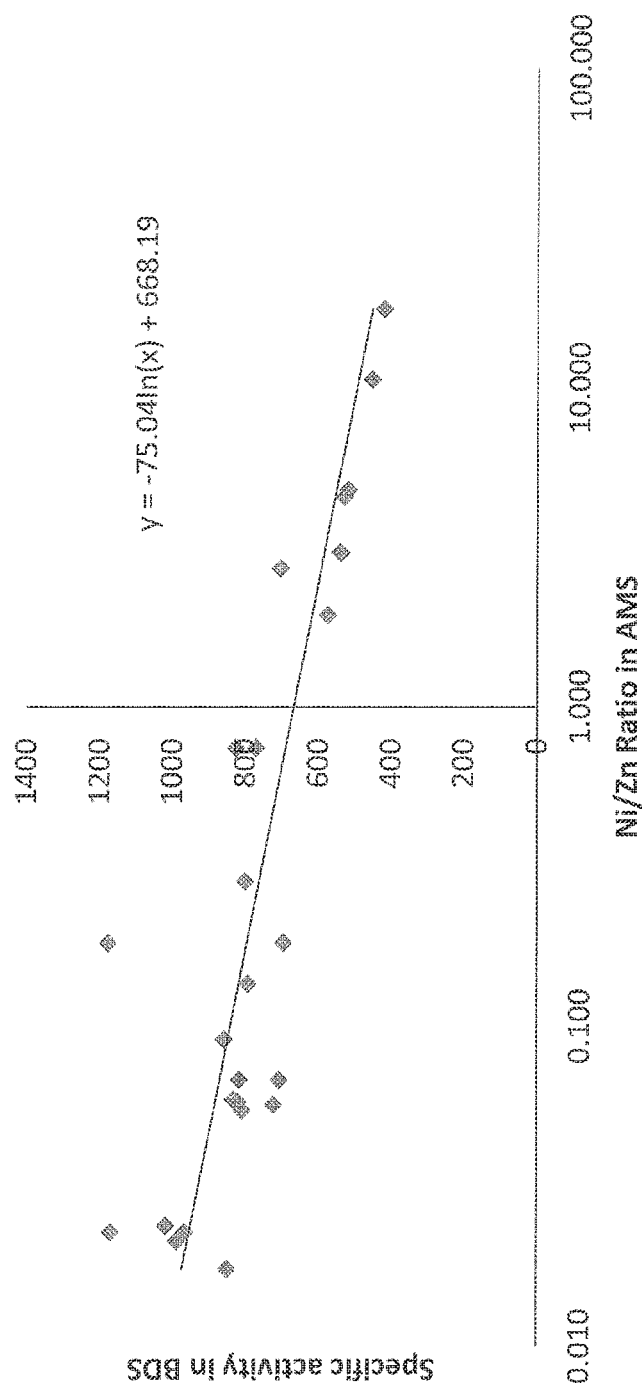

FIG. 15 is a graph showing the correlation between the Ni/Zn molar ratio in the AMS used in the HIC step and the specific activity in the final BDS. The specific activity was calculated to be equal to 668.19−75.04×ln (Ni/Zn molar ratio), while $R^2=0.66$.

Figure 16:
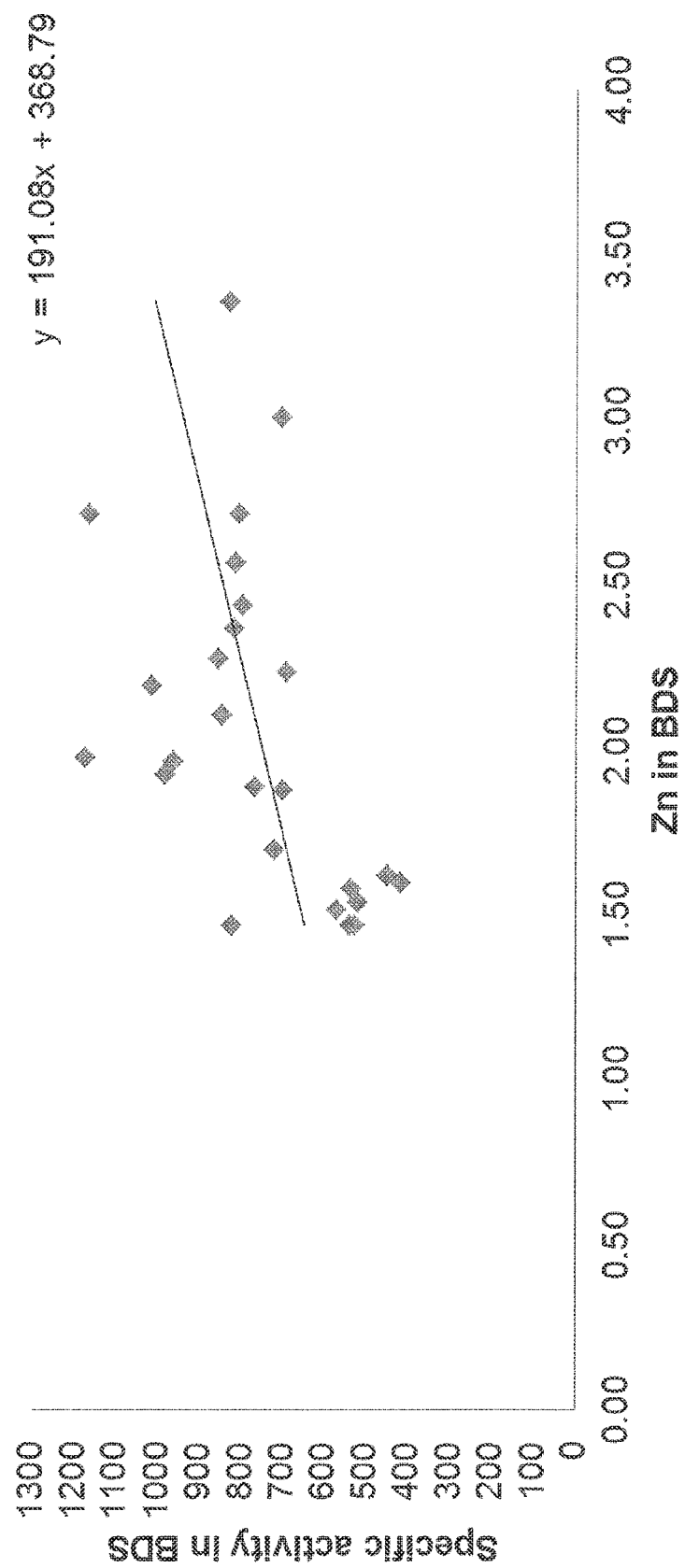

FIG. 16 is a graph showing the correlation between the Zn molar ratio (i.e., moles of zinc/mole of asfotase alfa monomer) in the asfotase alfa bulk drug substance (BDS) and the specific activity in the final BDS. The specific activity was calculated to be equal to 368.79+191.08×Zn molar ratio, while $R^2=0.24$. The correlation between the Zn content in the BDS vs. the specific activity of the BDS was lower than the cut-off threshold, showing only weak correlation.

Figure 17:
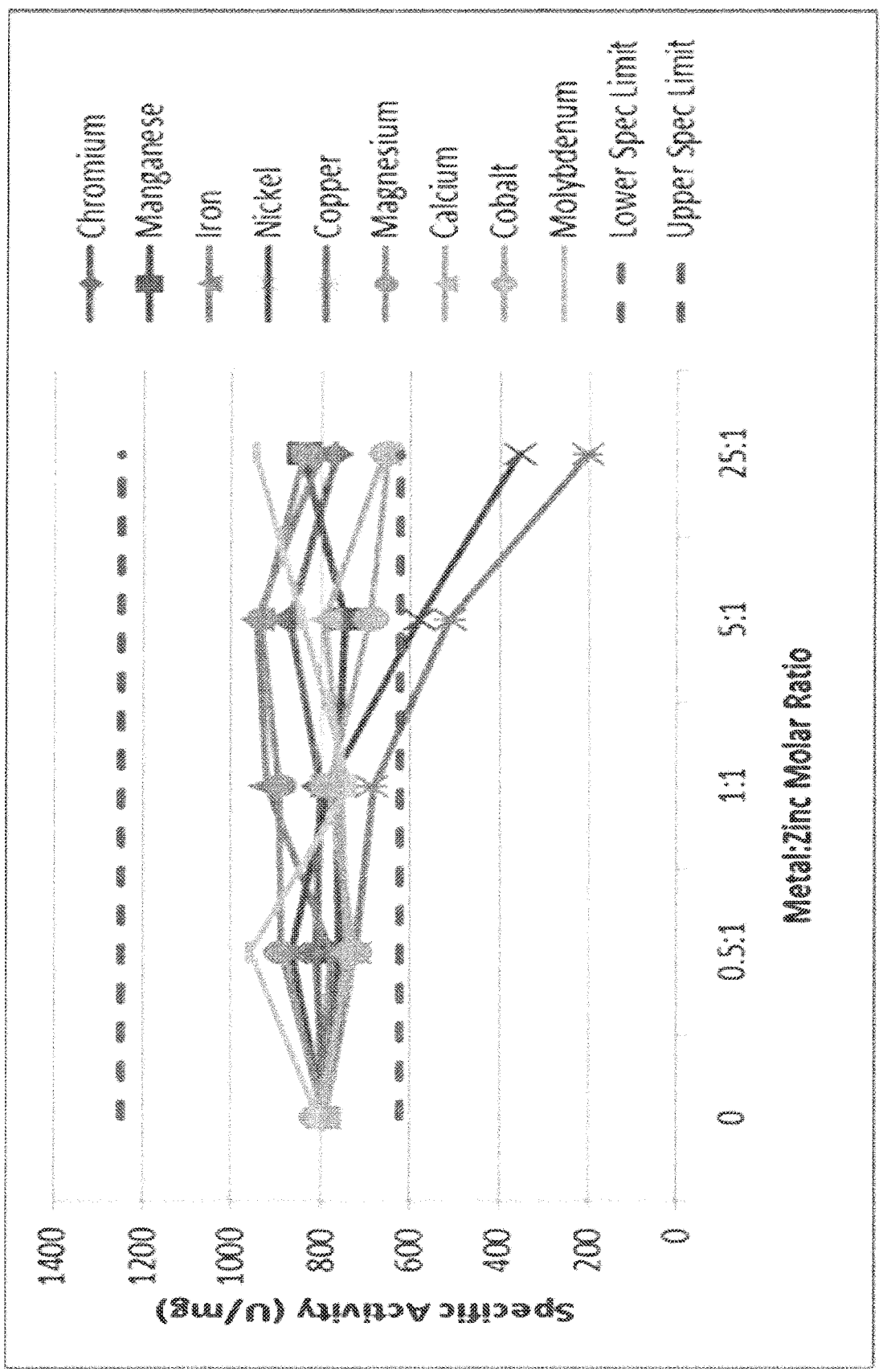

FIG. 17 is a graph showing the impact of different metal/Zn molar ratios in the AMS used in the HIC step on the specific activity of the produced asfotase alfa in the HIC pools. The dotted lines represent the lower limit and the upper limit for the specific activity of asfotase alfa.

Figure 18:
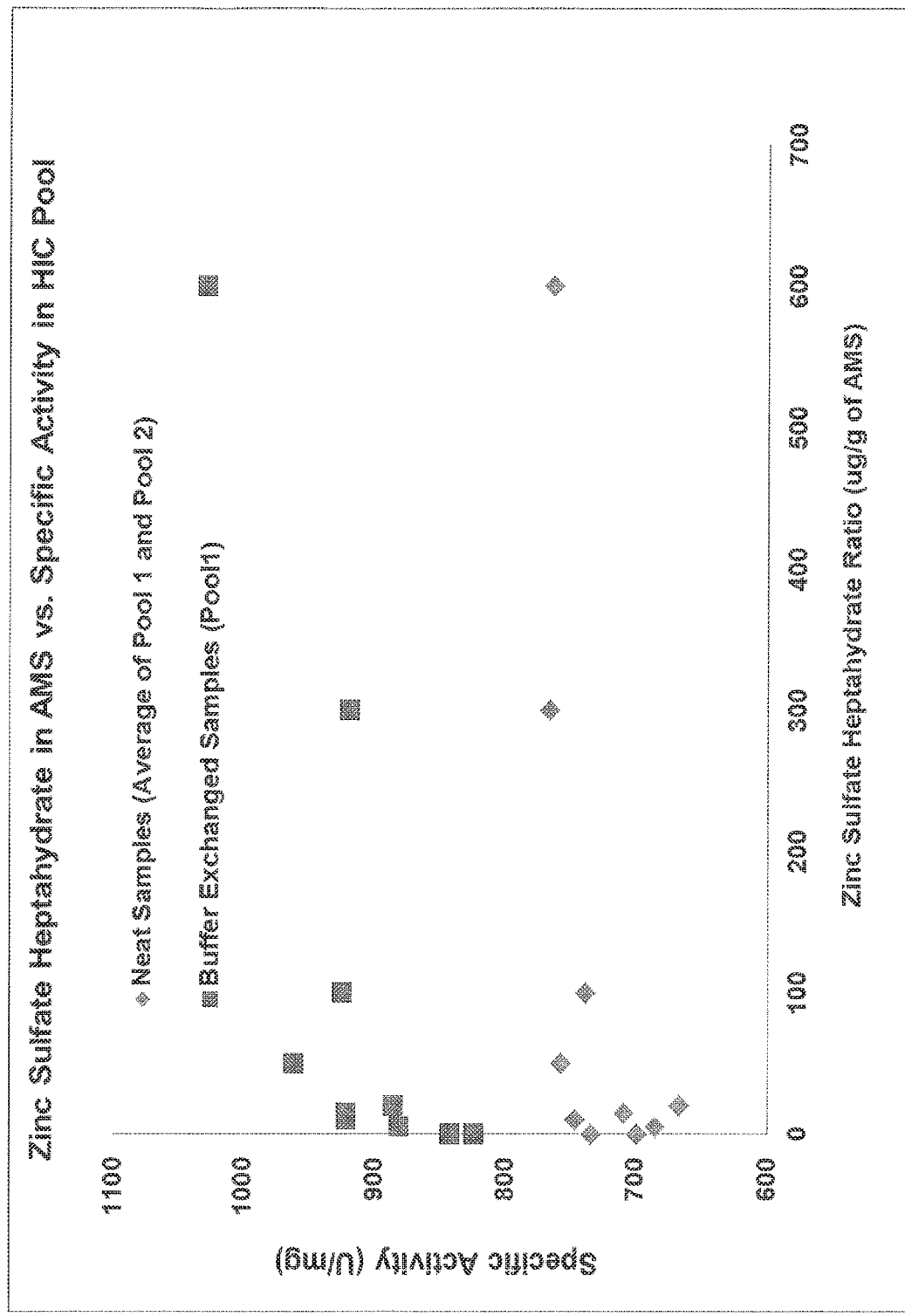

FIG. 18 is a graph showing the impact of Zn supplementation to the AMS used in the HIC step on the specific activity of the produced asfotase alfa in the HIC pools.

Figure 19:
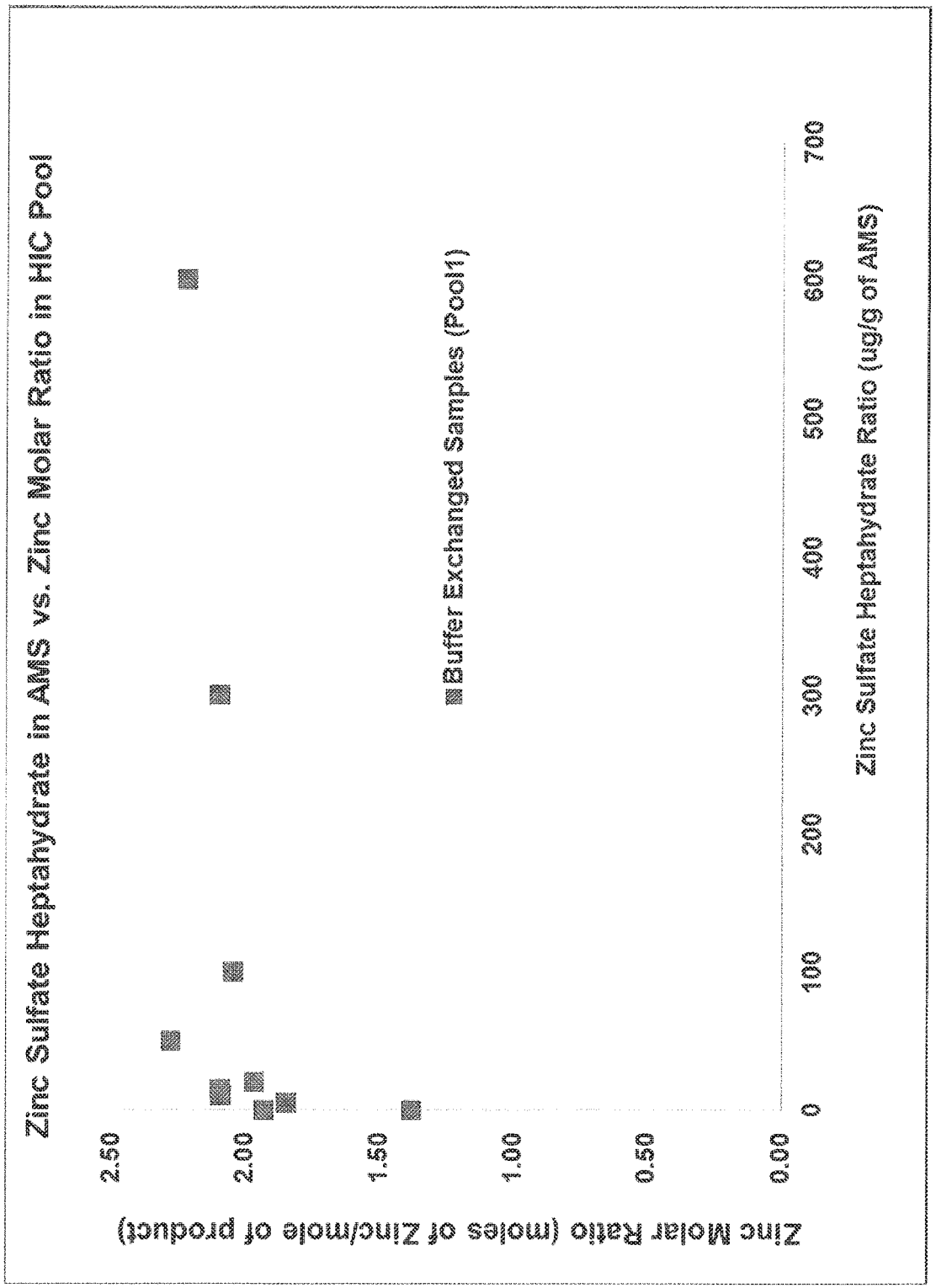

FIG. 19 is a graph showing the impact of Zn supplementation to the AMS used in the HIC step on the Zinc molar ratio in the HIC pools.

Figure 20:
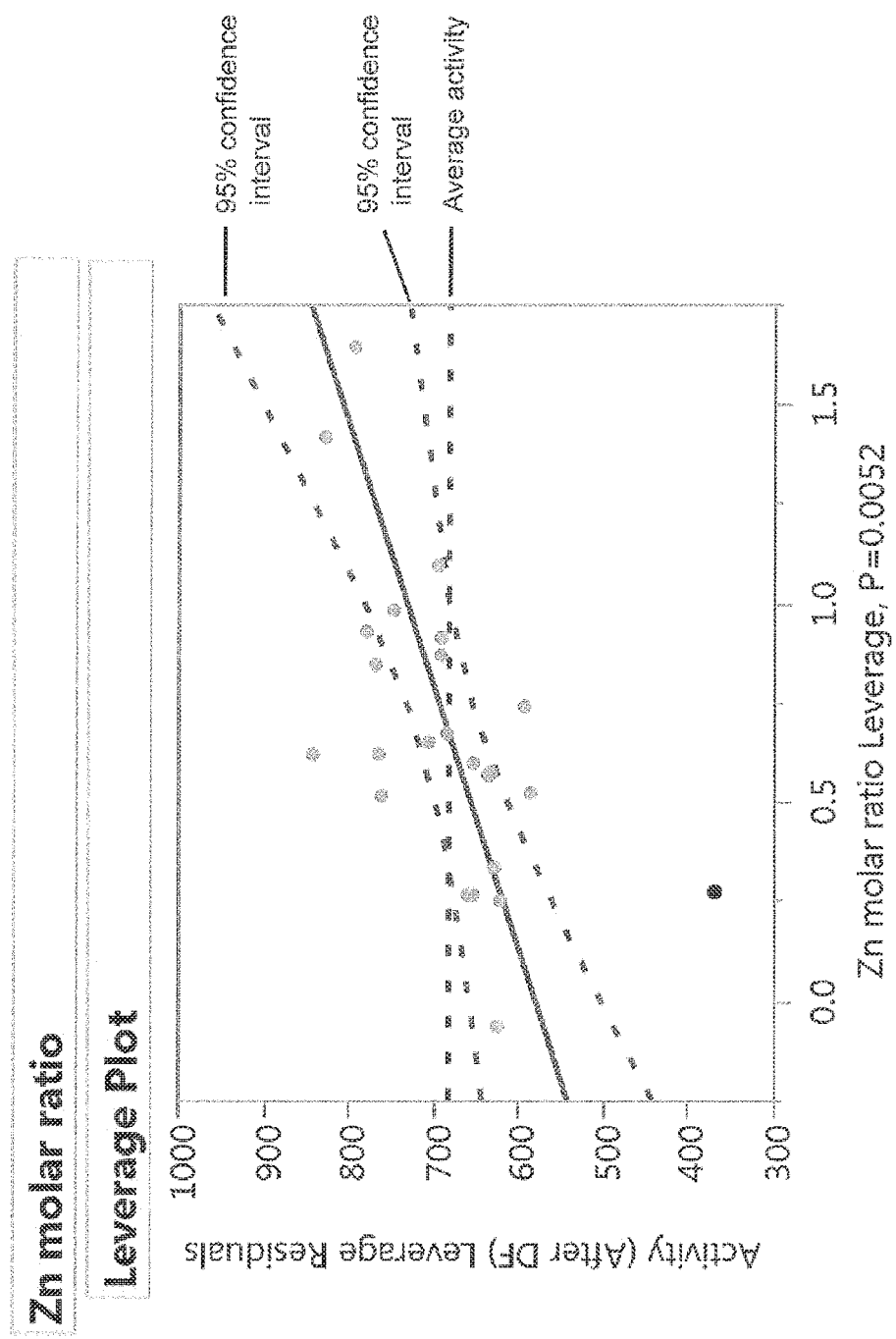

FIG. 20 is an actual-by-predicted plot showing a linear correlation (the solid line) between the Zn molar ratio (i.e., moles of zinc/mole of asfotase alfa monomer) in the HIC pool and the specific activity in the HIC pool. The two curved dotted lines represent the 95% confidence interval. The horizontal dotted line represents the average activity of all tested examples.

Figure 21:
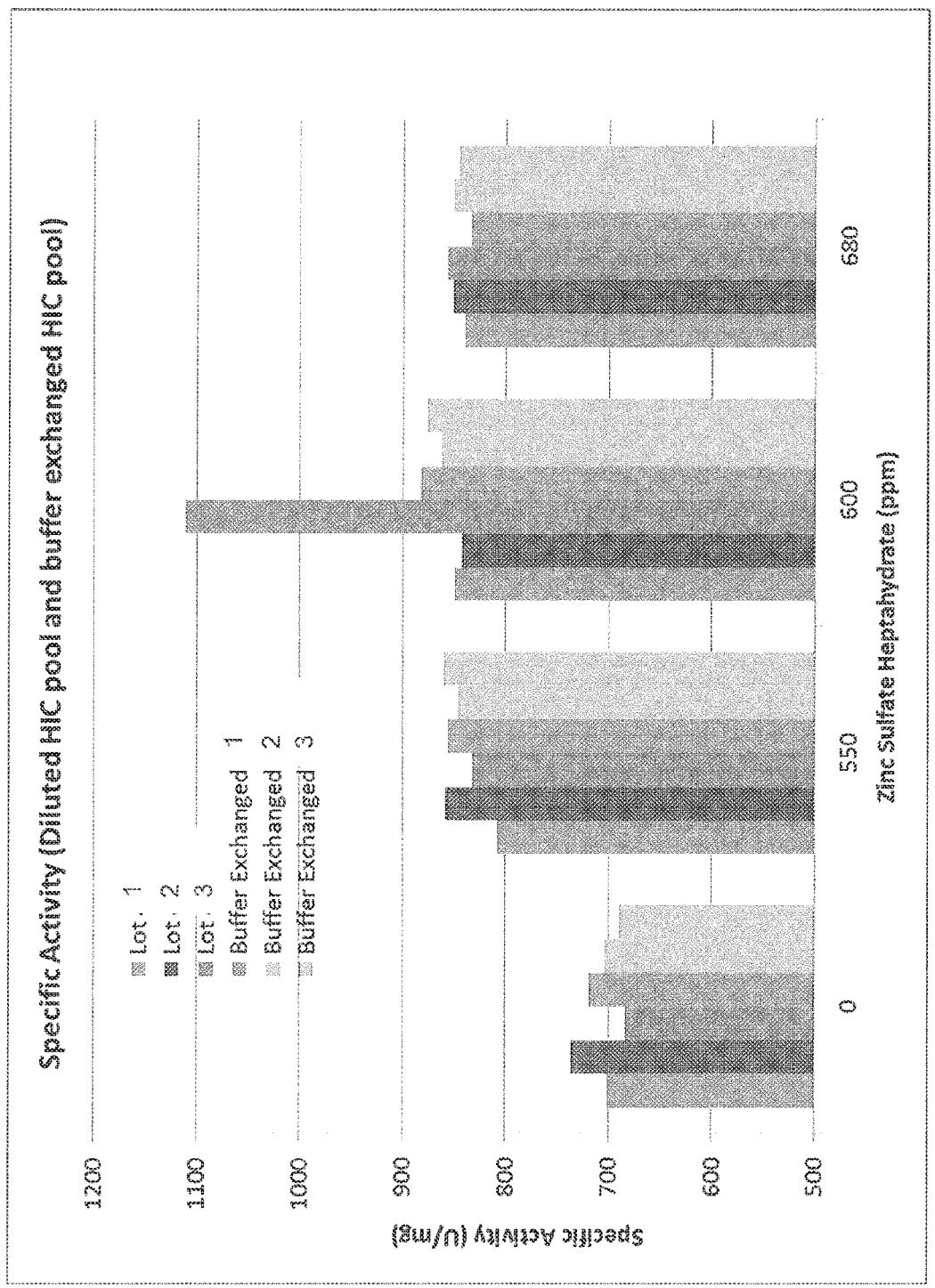

FIG. 21 is a graph showing the impact of Zn supplementation (500, 600, or 680 ppm, in the format of zinc sulfate heptahydrate) to the AMS used in the HIC step on the specific activity of the produced asfotase alfa in the HIC pools in three lots of AMS (with or without buffer exchange).

Figure 22:
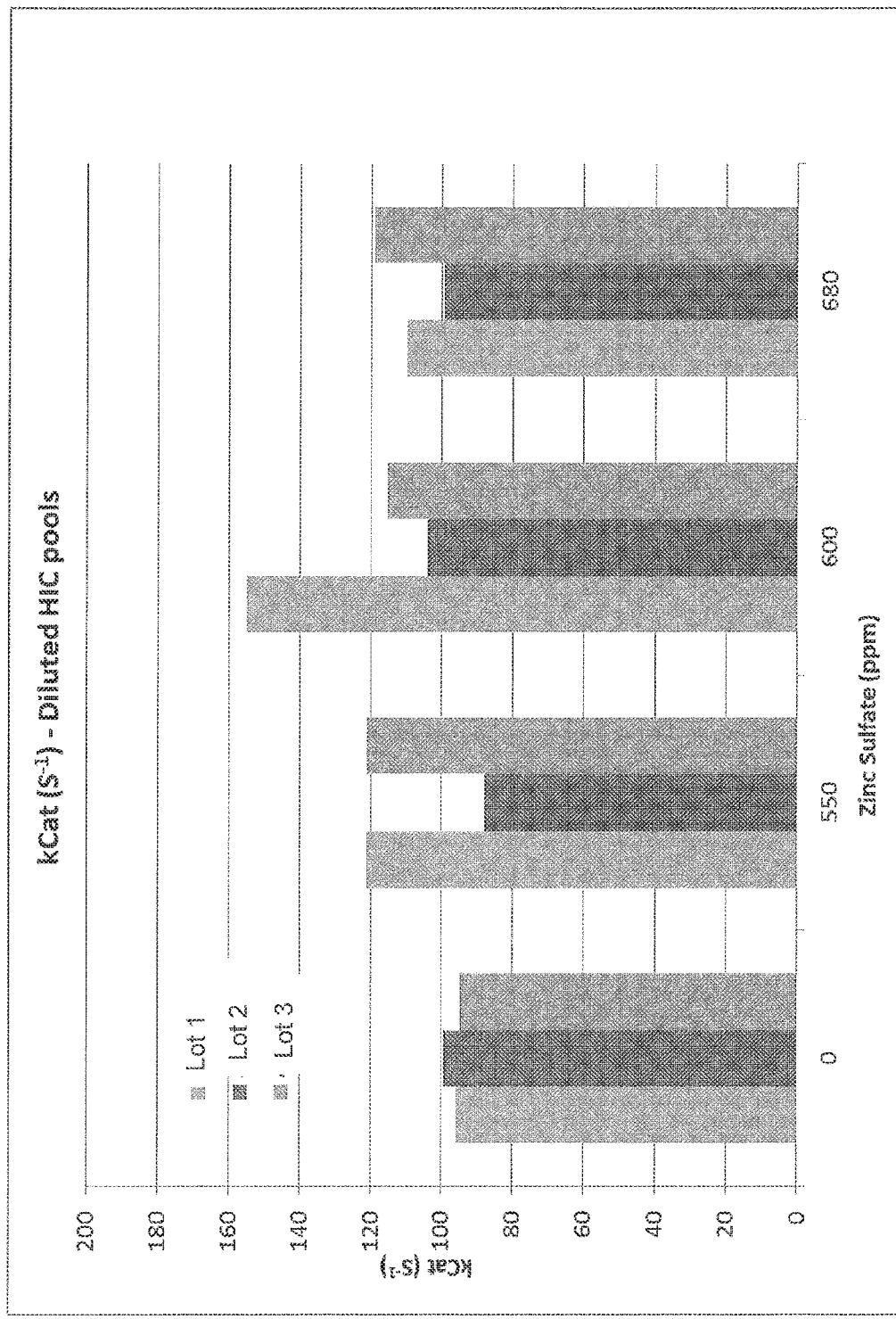

FIG. 22 is a graph showing the impact of Zn supplementation (500, 600, or 680 ppm, in the format of zinc sulfate) to the AMS used in the HIC step on the $K_{cat}$ of the produced asfotase alfa in the HIC pools in three lots of AMS.

Figure 23:
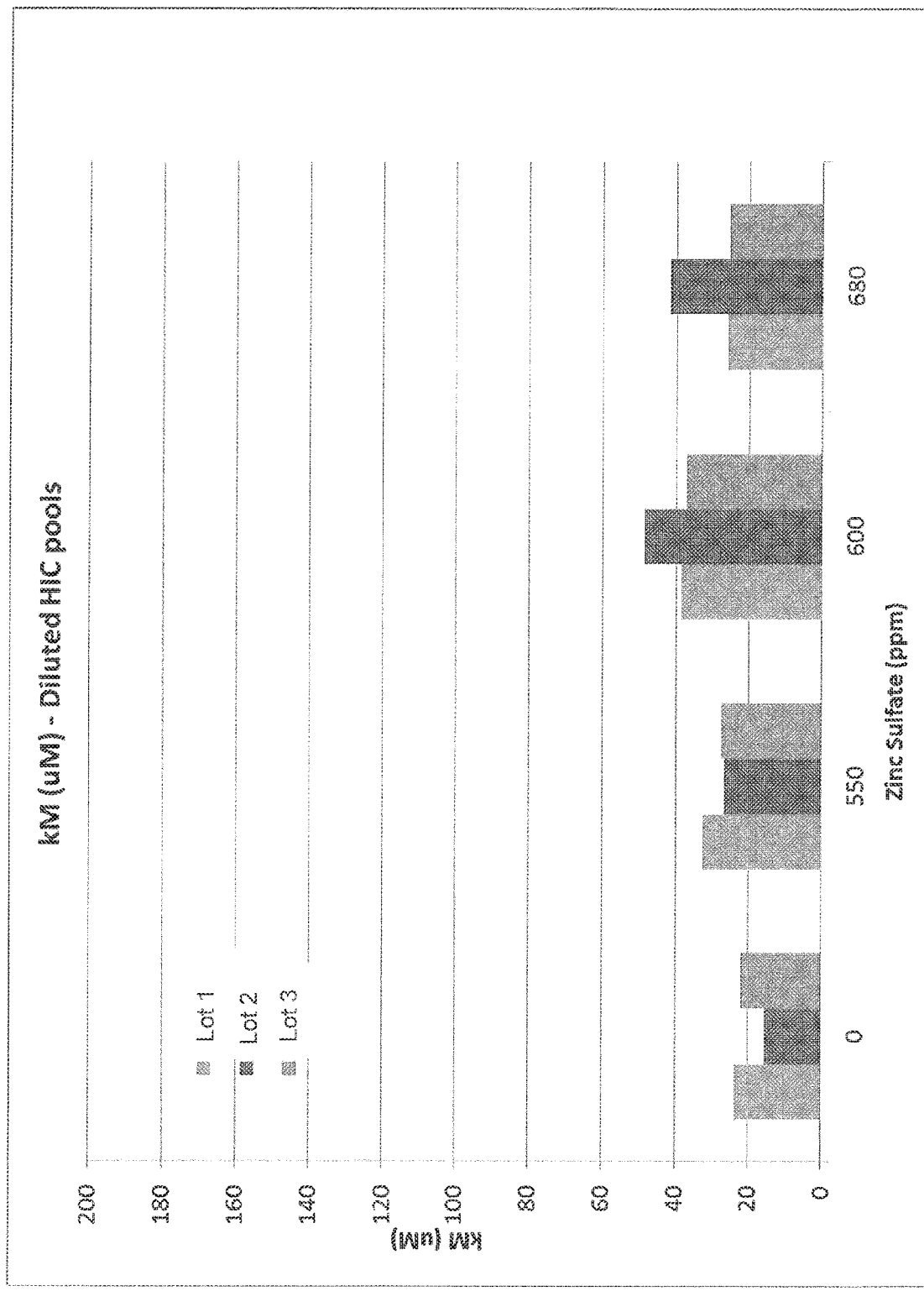

FIG. 23 is a graph showing the impact of Zn supplementation (500, 600, or 680 ppm, in the format of zinc sulfate) to the AMS used in the HIC step on the $K_m$ of the produced asfotase alfa in the HIC pools in three lots of AMS.

Figure 24:
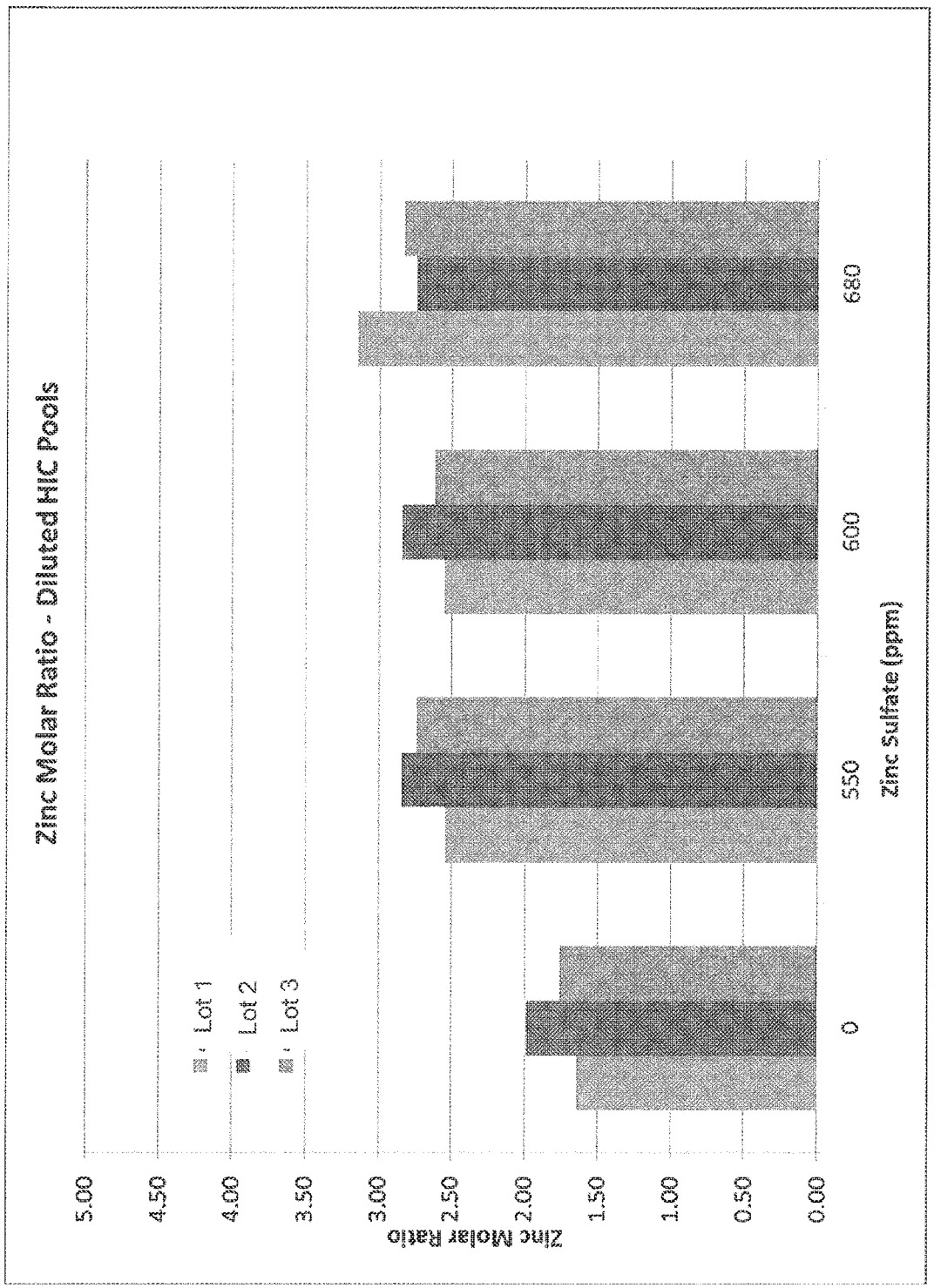

FIG. 24 is a graph showing the impact of Zn supplementation (500, 600, or 680 ppm, in the format of zinc sulfate) to the AMS used in the HIC step on the Zinc molar ratio in the HIC pools in three lots of AMS.

Figure 25A:
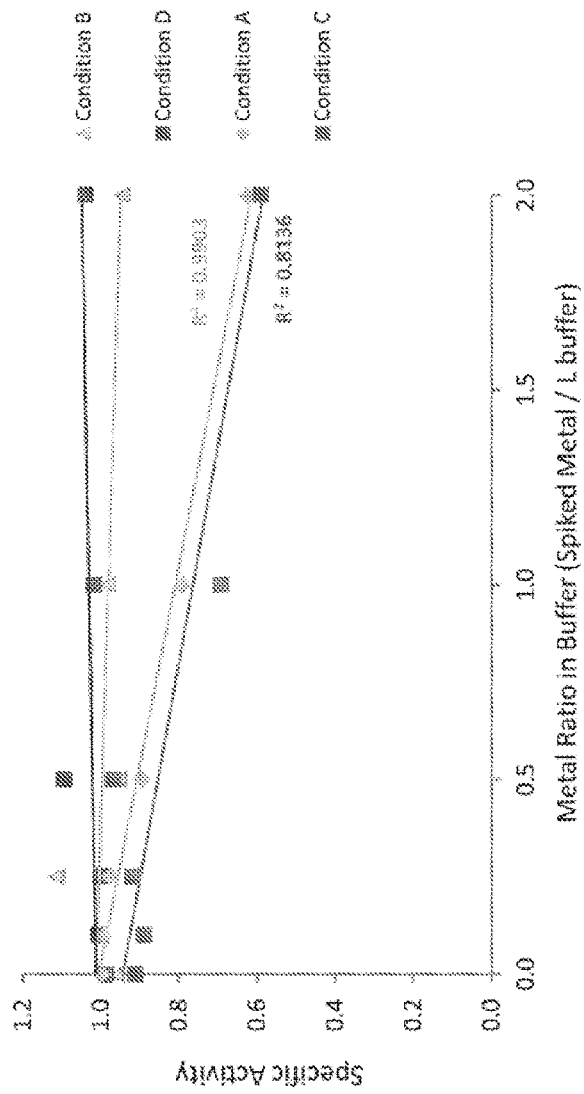
Figure 25B:
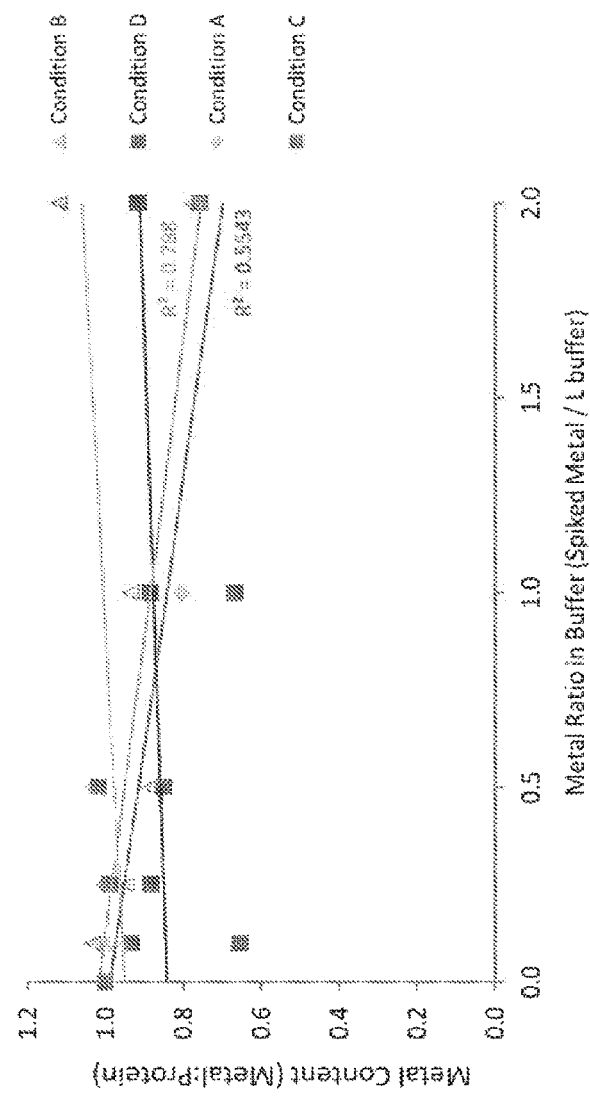

FIGS. 25A-25B are graphs showing the effect of HIC buffer composition and Ni spiked into HIC buffers (0-2 mg/L) on the specific activity of asfotase alfa in the HIC purified pool (FIG. 25A) and the zinc content of asfotase alfa in the HIC purified pool (FIG. 25B). Shown are the results for Condition A (Butyl SEPHAROSE® HP resin and AMS buffer), Condition B (Butyl SEPHAROSE® HP resin and sodium sulfate buffer), Condition C (CAPTO® Butyl and AMS buffer), and Condition D (CAPTO® Butyl agarose resin and sodium sulfate buffer). The $R^2$ displayed is for linear regression of Conditions A and C, and the specific activity and zinc content for FIGS. 25A and 25B are normalized to that of the non-spiked control within each condition.

DETAILED DESCRIPTION

Definitions

"About", "Approximately": As used herein, the terms "about" and "approximately", as applied to one or more particular cell culture conditions, refer to a range of values that are similar to the stated reference value for that culture condition or conditions. In certain embodiments, the term "about" refers to a range of values that fall within 25, 20, 19, 18, 17, 16, 15, 14, 13, 12, 11, 10, 9, 8, 7, 6, 5, 4, 3, 2, 1 percent or less of the stated reference value for that culture condition or conditions.

"Amino acid": The term "amino acid," as used herein, refers to any of the twenty naturally occurring amino acids that are normally used in the formation of polypeptides, or analogs or derivatives of those amino acids. Amino acids of the present disclosure can be provided in medium to cell cultures. The amino acids provided in the medium may be provided as salts or in hydrate form.

"Culture" and "cell culture": These terms, as used herein, refer to a cell population that is suspended in a medium (see definition of "medium" below) under conditions suitable for survival and/or growth of the cell population. As will be clear to those of ordinary skill in the art, these terms as used herein may refer to the combination comprising the cell population and the medium in which the population is suspended.

"Fragment": The term "fragment," as used herein, refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In some embodiments the fraction of activity retained is at least 10% of the activity of the full-length polypeptide. In various embodiments the fraction of activity retained is at least 20%, 30%, 40%, 50%, 60%, 70%, 80% or 90% of the activity of the full-length polypeptide. In other embodiments the fraction of activity retained is at least 95%, 96%, 97%, 98% or 99% of the activity of the full-length polypeptide. In one embodiment, the fraction of activity retained is 100% of the activity of the full-length polypeptide. The term as used herein also refers to any portion of a given polypeptide that includes at least an established sequence element found in the full-length polypeptide. In some embodiments, the sequence element spans at least 4-5 amino acids of the full-length polypeptide. In some embodiments, the sequence element spans at least about 10, 15, 20, 25, 30, 35, 40, 45, 50 or more amino acids of the full-length polypeptide.

"Medium", "cell culture medium", and "culture medium": These terms, as used herein, refer to a solution containing nutrients which nourish growing mammalian cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is, e.g., formulated to a pH and salt concentration optimal for cell survival and proliferation. The medium may also be a "defined media"—a serum-free media that contains no proteins, hydrolysates or components of unknown composition. Defined media are free of animal-derived components and all components have a known chemical structure.

"Metabolic waste product": The term "metabolic waste product," as used herein, refers to compound produced by the cell culture as a result of normal or non-normal metabolic processes that are in some way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, glycosylation or other post-translational modification of the expressed polypeptide or protein, or may be detrimental to the cells and/or expression or activity of the recombinant polypeptide or protein in any number of other ways. Exemplary metabolic waste products include lactate, which is produced as a result of glucose metabolism, and ammonium, which is produced as a result of glutamine metabolism. In one embodiment, methods are taken to slow production of, reduce or even eliminate metabolic waste products in cell cultures.

"Polypeptide": The term "polypeptide," as used herein, refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond.

"Protein": The term "protein," as used herein, refers to one or more polypeptides that function as a discrete unit. If a single polypeptide is the discrete functioning unit and does not require permanent physical association with other polypeptides in order to form the discrete functioning unit, the terms "polypeptide" and "protein" as used herein are used interchangeably.

"Recombinantly-expressed polypeptide" and "recombinant polypeptide": These terms, as used herein, refer to a polypeptide expressed from a host cell that has been genetically engineered to express that polypeptide. The recombinantly-expressed polypeptide can be identical or similar to a polypeptide that is normally expressed in the mammalian host cell. The recombinantly-expressed polypeptide can also be foreign to the host cell, i.e., heterologous to peptides normally expressed in the host cell. Alternatively, the recombinantly-expressed polypeptide can be chimeric in that portions of the polypeptide contain amino acid sequences that are identical or similar to polypeptides normally expressed in the mammalian host cell, while other portions are foreign to the host cell.

As used herein, the term "hydrophobic interaction chromatography (HIC) column" refers to a column containing a stationary phase or resin and a mobile or solution phase in which the hydrophobic interaction between a protein and hydrophobic groups on the stationary phase or resin separates a protein from impurities including fragments and aggregates of the subject protein, other proteins or protein fragments and other contaminants such as cell debris, or residual impurities from other purification steps. The stationary phase or resin comprises a base matrix or support such as a cross-linked agarose, silica or synthetic copolymer material to which hydrophobic ligands are attached. Examples of such stationary phase or resins include phenyl-, butyl-, octyl-, hexyl- and other alkyl substituted agarose, silica, or other synthetic polymers. Columns may be of any size containing the stationary phase, or may be open and batch processed.

As used herein, the term "preparation" refers to a solution comprising a protein of interest (e.g., a recombinant alkaline phosphatase described herein) and at least one impurity from a cell culture producing such protein of interest and/or a solution used to extract, concentrate, and/or purify such protein of interest from the cell culture. For example, a preparation of a protein of interest (e.g., a recombinant alkaline phosphatase described herein) may be prepared by homogenizing cells, which grow in a cell culture and produce such protein of interest, in a homogenizing solution.

As used herein, the term "solution" refers to a homogeneous, molecular mixture of two or more substances in a liquid form. Specifically, the proteins to be purified, such as the recombinant alkaline phosphatases or their fusion proteins (e.g., asfotase alfa) in the present disclosure represent one substance in a solution. The term "buffer" or "buffered solution" refers to solutions which resist changes in pH by the action of its conjugate acid-base range. Examples of buffers that control pH at ranges of about pH 5 to about pH 7 include HEPES, citrate, phosphate, and acetate, and other mineral acid or organic acid buffers, and combinations of these. Salt cations include sodium, ammonium, and potassium. As used herein the term "loading buffer/solution" or "equilibrium buffer/solution" refers to the buffer/solution containing the salt or salts which is mixed with the protein preparation for loading the protein preparation onto a HIC column. This buffer/solution is also used to equilibrate the column before loading, and to wash to column after loading the protein. The "elution buffer/solution" refers to the buffer/solution used to elute the protein from the column. As used herein, the term "solution" refers to either a buffered or a non-buffered solution, including water.

The term "HIC pool" refers to, unless otherwise specified, the elution fraction after the HIC step, comprising a protein of interest (e.g., a recombinant alkaline phosphatase), initially bound to a HIC column and then eluted off by at least one elution solution. In one example, a HIC pool comprises the recombinant alkaline phosphatase described herein either in a higher concentration or in a more enzymatically active state, compared to the recombinant alkaline phosphatase described herein in the preparation prior to the HIC step, or both.

The term "minimize," or in other similar forms, refers to reducing the concentration of certain molecules (e.g., at least one of metal ions) in certain solutions (e.g., a preparation comprising a recombinant alkaline phosphatase, or other solutions used in the purification processes for such recombinant alkaline phosphatase, such as solutions for a HIC step), preferably to less than a certain level. For example, the method described herein may comprise minimizing or reducing the concentration of certain metal ions (e.g., Ni, Cu, Co, Mn, etc.) in a preparation comprising a recombinant alkaline phosphatase produced by a cell culture or in solutions for at least one purification processes for such recombinant alkaline phosphatase (e.g., solutions for a HIC step) to less than a certain level so that such metal ions may not interfere the Zinc-enzyme structural formulation for the purified recombinant alkaline phosphatase. Thus, by minimizing the concentration of certain metal ions to less than said certain level, the purified recombinant alkaline phosphatase has increased activity compared to, or does not lose as much activity as, the recombinant alkaline phosphatase purified through same processes but without minimizing the concentration of said certain metal ions.

The present disclosure provides a method of improving the enzymatic function of a recombinant protein which is expressed by cell culture (e.g., mammalian cells including but not limited to Chinese Hamster Ovary (CHO) cells). Specifically, a recombinant protein may be produced by a certain type of cells (e.g., mammalian cells including but not limited to Chinese Hamster Ovary (CHO) cells) through, for example, a fermentation process. The total processes of inoculation and growth of the cells, induction of protein expression, and various parameter optimizations for protein expression are referred as upstream processing steps. Correspondingly, the downstream processing steps may include, e.g., the recovery and purification of the produced proteins (i.e., separation of the produced proteins from other impurities and/or contaminants originated from the cells and the culture medium). Exemplary downstream process steps include, for example, protein capturing from harvest, removing host cell debris, host cell proteins (HCPs), and host cell DNAs, endotoxins, viruses and other containments, buffer-exchanging, and formulation adjustment, etc.

The present disclosure provides a method of improving the enzymatic function of an alkaline phosphatase (e.g., asfotase alfa) which is produced by cell culture. In certain embodiments, such method includes targeting the downstream processing steps for the produced alkaline phosphatase (e.g., asfotase alfa). For example, such method may include adjusting metal ion concentrations in the buffers and/or solutions used in the downstream processing steps (e.g., separation, purification, filtration (e.g., ultrafiltration (UF) and diafiltration (DF)), concentration, formulation and bulk fill, etc.). The concentration of different metal ions may be decreased or increased according to each metal ion's own characteristics which affect the enzymatic function of the alkaline phosphatase (e.g., asfotase alfa).

Proteins

The present disclosure relates to the downstream processing (e.g., separation and purification) of an alkaline phosphatase protein (e.g., asfotase alfa) which is expressed in cell culture. The alkaline phosphatase protein includes any polypeptides or molecules comprising polypeptides that comprise at least some alkaline phosphatase activity. In certain embodiments, such alkaline phosphatase protein, after being produced and then purified by the methods disclosed herein, can be used to treat or prevent alkaline phosphatase-related diseases or disorders. For example, such alkaline phosphatase protein may be administered to a subject having decreased and/or malfunctioned endogenous alkaline phosphatase, or having overexpressed (e.g., above normal level) alkaline phosphatase substrates. In some embodiments, the alkaline phosphatase protein in this disclosure is a recombinant protein. In some embodiments, the alkaline phosphatase protein is a fusion protein. In some embodiments, the alkaline phosphatase protein in this disclosure specifically targets a cell type, tissue (e.g., connective, muscle, nervous, or epithelial tissues), or organ (e.g., liver, heart, kidney, muscles, bones, cartilage, ligaments, tendons, etc.). For example, such alkaline phosphatase protein may comprise a full-length alkaline phosphatase (ALP) or fragment of at least one alkaline phosphatase (ALP). In some embodiments, the alkaline phosphatase protein comprises a soluble ALP (sALP) linked to a bone-targeting moiety (e.g., a negatively-charged peptide as described below). In some embodiments, the alkaline phosphatase protein comprises a soluble ALP (sALP) linked to an immunoglobulin moiety (full-length or fragment). For example, such immunoglobulin moiety may comprise a fragment crystallizable region (Fc). In some embodiments, the alkaline phosphatase protein comprises a soluble ALP (sALP) linked to both a bone-targeting moiety and an immunoglobulin moiety (full-length or fragment). For more detailed description of the alkaline phosphatase protein disclosed herein, see PCT Publication Nos. WO 2005/103263 and WO 2008/138131, the entire teachings of both of which are incorporated by reference herein in their entirety.

In some embodiments, the alkaline phosphatase protein described herein comprises any one of the structures selected from the group consisting of: sALP-X, X-sALP, sALP-Y, Y-sALP, sALP-X-Y, sALP-Y-X, X-sALP-Y, X-Y-sALP, Y-sALP-X, and Y-X-sALP, wherein X comprises a bone-targeting moiety, as described herein, and Y comprises an immunoglobulin moiety, as described herein. In one embodiment, the alkaline phosphatase protein comprises the structure of W-sALP-X-Fc-Y-$D_n$/$E_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n$/$E_n$ is a polyaspartate, polyglutamate, or combination thereof wherein n=8-20; and sALP is a soluble alkaline phosphatase (ALP). In some embodiments, $D_n$/$E_n$ is a polyaspartate sequence. For example, $D_n$ may be a polyaspartate sequence wherein n is any number between 8 and 20 (both included) (e.g., n may be 8, 9, 10, 11, 12, 13, 14, 15, 16, 17, 18, 19, and 20). In one embodiment, $D_n$ is $D_{10}$ or $D_{16}$. In some embodiments, $D_n$/$E_n$ is a polyglutamate sequence. For example, $E_n$ may be a polyglutamate sequence wherein n is any number between 8 and 20 (both included) (e.g., n may be 8, 9, 10, 11, 12, 13, 14, 15, 16, 17, 18, 19, and 20). In one embodiment, $E_n$ is $E_{10}$ or $E_{16}$. In one embodiment, the alkaline phosphatase protein comprises the structure of TNALP-Fc-$D_{10}$ (SEQ ID NO: 1, as listed below). Underlined asparagine (N) residues correspond to potential glycosylation sites (i.e., N 123, 213, 254, 286, 413 & 564). Bold underlined amino acid residues ($L_{486}$-$K_{487}$ & $D_{715}$-$I_{716}$) correspond to linkers between sALP and Fc, and Fc and $D_{10}$ domains, respectively.

```
                                          (SEQ ID NO: 1)
         10          20          30          40
LVPEKEKDPK  YWRDQAQETL  KYALELQKLN  TNVAKNVIMF 50          60          70          80
LGDGMGVSTV  TAARILKGQL  HHNPGEETRL  EMDKFPFVAL 90         100         110         120
SKTYNTNAQV  PDSAGTATAY  LCGVKANEGT  VGVSAATERS 130         140         150         160
RCNTTQGNEV  TSILRWAKDA  GKSVGIVTTT  RVNHATPSAA 170         180         190         200
YAHSADRDWY  SDNEMPPEAL  SQGCKDIAYQ  LMHNIRDIDV 210         220         230         240
IMGGGRKYMY  PKNKTDVEYE  SDEKARGTRL  DGLDLVDTWK 250         260         270         280
SFKPRYKHSH  FIWNRTELLT  LDPHNVDYLL  GLFEPGDMQY 290         300         310         320
ELNRNNVTDP  SLSEMVVVAI  QILRKNPKGF  FLLVEGGRID 330         340         350         360
HGHHEGKAKQ  ALHEAVEMDR  AIGQAGSLTS  SEDTLTVVTA 370         380         390         400
DHSHVFTFGG  YTPRGNSIFG  LAPMLSDTDK  KPFTAILYGN 410         420         430         440
GPGYKVVGGE  RENVSMVDYA  HNNYQAQSAV  PLRHETHGGE 450         460         470         480
DVAVFSKGPM  AHLLHGVHEQ  NYVPHVMAYA  ACIGANLGHC 490         500         510         520
APASSLKDKT  HTCPPCPAPE  LLGGPSVFLF  PPKPKDTLMI 530         540         550         560
SRTPEVTCVV  VDVSHEDPEV  KFNWYVDGVE  VHNAKTKPRE
```

```
              570        580        590        600
         EQYNSTYRVV SVLTVLHQDW LNGKEYKCKV SNKALPAPIE 610        620        630        640
         KTISKAKGQP REPQVYTLPP SREEMTKNQV SLTCLVKGFY 650        660        670        680
         PSDIAVEWES NGQPENNYKT TPPVLDSDGS FFLYSKLTVD 690        700        710        720
         KSRWQQGNVF SCSVMHEALH NHYTQKSLSL SPGKDIDDDD

DDDDDD
```

Asfotase alfa is a soluble Fc fusion protein consisting of two TNALP-Fc-$D_{10}$ polypeptides each with 726 amino acids as shown in SEQ ID NO:1. Each polypeptide or monomer is composed of five portions. The first portion (sALP) containing amino acids L1-S485 is the soluble part of the human tissue non-specific alkaline phosphatase enzyme, which contains the catalytic function. The second portion contains amino acids L486-K487 as a linker. The third portion (Fc) containing amino acids D488-K714 is the Fc part of the human Immunoglobulin gamma 1 (IgG1) containing hinge, $CH_2$ and $CH_3$ domains. The fourth portion contains D715-1716 as a linker. The fifth portion contains amino acids D717-D726 ($D_{10}$)), which is a bone targeting moiety that allows asfotase alfa to bind to the mineral phase of bone. In addition, each polypeptide chain contains six potential glycosylation sites and eleven cysteine (Cys) residues. Cys102 exists as free cysteine. Each polypeptide chain contains four intra-chain disulfide bonds between Cys122 and Cys184, Cys472 and Cys480, Cys528 and Cys588, and Cys634 and Cys692. The two polypeptide chains are connected by two inter-chain disulfide bonds between Cys493 on both chains and between Cys496 on both chains. In addition to these covalent structural features, mammalian alkaline phosphatases are thought to have four metal-binding sites on each polypeptide chain, including two sites for zinc, one site for magnesium and one site for calcium.

Alkaline Phosphatases (ALPs)

There are four known isozymes of ALP, namely tissue non-specific alkaline phosphatase (TNALP) further described below, placental alkaline phosphatase (PALP) (as described e.g., in GenBank Accession Nos. NP_112603 and NP_001623), germ cell alkaline phosphatase (GCALP) (as described, e.g., in GenBank Accession No. P10696) and intestinal alkaline phosphatase (IAP) (as described, e.g., in GenBank Accession No. NP_001622). These enzymes possess very similar three-dimensional structures. Each of their catalytic sites contains four metal-binding domains, for metal ions that are necessary for enzymatic activity, including two Zn and one Mg. These enzymes catalyze the hydrolysis of monoesters of phosphoric acid and also catalyze a transphosphorylation reaction in the presence of high concentrations of phosphate acceptors. Three known natural substrates for ALP (e.g., TNALP) include phosphoethanolamine (PEA), inorganic pyrophosphate (PPi) and pyridoxal 5′-phosphate (PLP) (Whyte et al., 1995 *J Clin Invest* 95:1440-1445). An alignment between these isozymes is shown in FIG. 30 of WO 2008/138131, the entire teachings of which are incorporated by reference herein in their entirety.

The alkaline phosphatase protein in this disclosure may comprise a dimer or multimers of any ALP protein, alone or in combination. Chimeric ALP proteins or fusion proteins may also be produced, such as the chimeric ALP protein that is described in Kiffer-Moreira et al. 2014 *PLUS One* 9:e89374, the entire teachings of which are incorporated by reference herein in its entirety.

TNALP

As indicated above, TNALP is a membrane-bound protein anchored through a glycolipid to its C-terminus (for human TNALP, see UniProtKB/Swiss-Prot Accession No. P05186). This glycolipid anchor (GPI) is added post translationally after removal of a hydrophobic C-terminal end which serves both as a temporary membrane anchor and as a signal for the addition of the GPI. Hence, in one embodiment a soluble human TNALP comprises a TNALP wherein the first amino acid of the hydrophobic C-terminal sequence, namely alanine, is replaced by a stop codon. The soluble TNALP (herein called sTNALP) so formed contains all amino acids of the native anchored form of TNALP that are necessary for the formation of the catalytic site but lacks the GPI membrane anchor. Known TNALPs include, e.g., human TNALP [GenBank Accession Nos. NP-000469, AAI10910, AAH90861, AAH66116, AAH21289, and AAI26166]; rhesus TNALP [GenBank Accession No. XP-001109717]; rat TNALP [GenBank Accession No. NP_037191]; dog TNALP [GenBank Accession No. AAF64516]; pig TNALP [GenBank Accession No. AAN64273], mouse TNALP [GenBank Accession No. NP_031457], bovine TNALP [GenBank Accession Nos. NP_789828, NP_776412, AAM 8209, and AAC33858], and cat TNALP [GenBank Accession No. NP_001036028].

As used herein, the terminology "extracellular domain" is meant to refer to any functional extracellular portion of the native protein (e.g., without the peptide signal). Recombinant sTNALP polypeptide retaining original amino acids 1 to 501 (18 to 501 when secreted), amino acids 1 to 502 (18 to 502 when secreted), amino acids 1 to 504 (18 to 504 when secreted), or amino acids 1 to 505 (18-505 when secreted) are enzymatically active (see Oda et al., 1999 *J. Biochem* 126:694-699). This indicates that amino acid residues can be removed from the C-terminal end of the native protein without affecting its enzymatic activity. Furthermore, the soluble human TNALP may comprise one or more amino acid substitutions, wherein such substitution(s) does not reduce or at least does not completely inhibit the enzymatic activity of the sTNALP. For example, certain mutations that are known to cause hypophosphatasia (HPP) are listed in PCT Publication No. WO 2008/138131 and should be avoided to maintain a functional sTNALP.

Negatively-Charged Peptide

The alkaline phosphatase protein of the present disclosure may comprise a target moiety which may specifically target the alkaline phosphatase protein to a pre-determined cell type, tissue, or organ. In some embodiments, such pre-determined cell type, tissue, or organ is bone tissues. Such bone-targeting moiety may include any known polypeptide, polynucleotide, or small molecule compounds known in the art. For example, negatively-charged peptides may be used as a bone-targeting moiety. In some embodiments, such negatively-charged peptides may be a poly-aspartate, poly-glutamate, or combination thereof (e.g., a polypeptide comprising at least one aspartate and at least one glutamate, such as a negatively-charged peptide comprising a combination of aspartate and glutamate residues). In some embodiments, such negatively-charged peptides may be $D_6$, $D_7$, $D_8$, $D_9$, $D_{10}$, $D_{11}$, $D_{12}$, $D_{13}$, $D_{14}$, $D_{15}$, $D_{16}$, $D_{17}$, $D_{18}$, $D_{19}$, $D_{20}$, or a polyaspartate having more than 20 aspartates. In some embodiments, such negatively-charged peptides may be $E_6$, $E_7$, $E_8$, $E_9$, $E_{10}$, $E_{11}$, $E_{12}$, $E_{13}$, $E_{14}$, $E_{15}$, $E_{16}$, $E_{17}$, $E_{18}$, $E_{19}$, $E_{20}$, or a polyglutamate having more than 20 glutamates. In one embodiment, such negatively-charged peptides may comprise at least one selected from the group consisting of $D_{10}$ to $D_{16}$ or $E_{10}$ to $E_{16}$.

Spacer

In some embodiments, the alkaline phosphatase protein of the present disclosure comprises a spacer sequence between the ALP portion and the targeting moiety portion. In one embodiment, such alkaline phosphatase protein comprises a spacer sequence between the ALP (e.g., TNALP) portion and the negatively-charged peptide targeting moiety. Such spacer may be any polypeptide, polynucleotide, or small molecule compound. In some embodiments, such spacer may comprise fragment crystallizable region (Fc) fragments. Useful Fc fragments include Fc fragments of IgG that comprise the hinge, and the $CH_2$ and $CH_3$ domains. Such IgG may be any of IgG-1, IgG-2, IgG-3, IgG-3 and IgG-4, or any combination thereof.

Without being limited to this theory, it is believed that the Fc fragment used in bone-targeted sALP fusion proteins (e.g., asfotase alfa) acts as a spacer, which allows the protein to be more efficiently folded given that the expression of sTNALP-Fc-$D_{10}$ was higher than that of sTNALP-$D_{10}$ (see Example 2 below). One possible explanation is that the introduction of the Fc fragment alleviates the repulsive forces caused by the presence of the highly negatively-charged $D_{10}$ sequence added at the C-terminus of the sALP sequence exemplified herein. In some embodiments, the alkaline phosphatase protein described herein comprises a structure selected from the group consisting of: sALP-Fc-$D_{10}$, sALP-$D_{10}$-Fc, $D_{10}$-sALP-Fc, $D_{10}$-Fc-sALP, Fc-sALP-$D_{10}$, and Fc-$D_{10}$-sALP. In other embodiments, the $D_{10}$ in the above structures is substituted by other negatively-charged polypeptides (e.g., $D_8$, $D_{16}$, $E_{10}$, $E_8$, $E_{16}$, etc.).

Useful spacers for the present disclosure include, e.g., polypeptides comprising a Fc, and hydrophilic and flexible polypeptides able to alleviate the repulsive forces caused by the presence of the highly negatively-charged bone-targeting sequence (e.g., $D_{10}$) added at the C-terminus of the sALP sequence.

Dimers/Tetramers

In specific embodiments, the bone-targeted sALP fusion proteins of the present disclosure are associated so as to form dimers or tetramers.

In the dimeric configuration, the steric hindrance imposed by the formation of the interchain disulfide bonds is presumably preventing the association of sALP domains to associate into the dimeric minimal catalytically-active protein that is present in normal cells.

Without being limited to this particular theory, it is believed that in its tetrameric structure, the association of the fusion proteins involves one sALP domain from one dimer linking to another sALP domain from a different dimer.

The bone-targeted sALP may further optionally comprise one or more additional amino acids 1) downstream from the negatively-charged peptide (e.g., the bone tag); and/or 2) between the negatively-charged peptide (e.g., the bone tag) and the Fc fragment; and/or 3) between the spacer (e.g., an Fc fragment) and the sALP fragment. This could occur, for example, when the cloning strategy used to produce the bone-targeting conjugate introduces exogenous amino acids in these locations. However the exogenous amino acids should be selected so as not to provide an additional GPI anchoring signal. The likelihood of a designed sequence being cleaved by the transamidase of the host cell can be predicted as described by Kezawa, 2002 Glycosylphosphatidylinositol (GPI)-anchored proteins. *Biol Pharm Bull.* 25:409-17.

The present disclosure also encompasses a fusion protein that is post-translationally modified, such as by glycosylation including those expressly mentioned herein, acetylation, amidation, blockage, formylation, gamma-carboxyglutamic acid hydroxylation, methylation, phosphorylation, pyrrolidone carboxylic acid, and sulfation.

Asfotase Alfa

The alkaline phosphatase protein described herein include, e.g., bone-targeted sALP fusion proteins, such as asfotase alfa (i.e., TNALP-Fc-$D_{10}$; SEQ ID NO:1). Specifically, asfotase alfa is a complex soluble glycoprotein with a polypeptide length of 726 amino acids. Asfotase alfa is an Fc-fusion protein composed of 3 domains. From the N-terminus to the C terminus, asfotase alfa comprises: (1) the soluble catalytic domain of human tissue non-specific alkaline phosphatase (TNSALP) (UniProtKB/Swiss-Prot Accession No. P05186), (2) the human immunoglobulin G1 Fc domain (UniProtKB/Swiss-Prot Accession No. P01857) and (3) a deca-aspartate peptide ($D_{10}$) used as a bone-targeting domain (Nishioka et al. 2006 *Mol Genet Metab* 88:244-255). The protein associates into a homo-dimer from two primary protein sequences. This fusion protein contains 6 confirmed complex N-glycosylation sites. Five of these N-glycosylation sites are located on the sALP domain and one on the Fc domain. Another important post-translational modification present on asfotase alfa is the presence of disulfide bridges stabilizing the enzyme and the Fc-domain structure. A total of 4 intra-molecular disulfide bridges are present per monomer and 2 inter-molecular disulfide bridges are present in the dimer. One cysteine of the alkaline phosphatase domain is free.

Asfotase alfa may be used as an enzyme-replacement therapy for the treatment of hypophosphatasia (HPP). In patients with HPP, loss-of-function mutation(s) in the gene encoding TNSALP causes a deficiency in TNSALP enzymatic activity, which leads to elevated circulating levels of substrates, such as inorganic pyrophosphate (PPi) and pyridoxal-5'-phosphate (PLP). Administration of asfotase alfa to patients with HPP cleaves PPi, releasing inorganic phosphate for combination with calcium, thereby promoting hydroxyapatite crystal formation and bone mineralization, and restoring a normal skeletal phenotype. For more details on asfotase alfa and its uses in treatment, see PCT Publication Nos. WO 2005/103263 and WO 2008/138131, the teachings of which are incorporated herein by reference in their entirety. In another embodiment, asfotase alfa may be used as an enzyme-replacement therapy for the treatment of Neurofibromatosis type I (NF1). For more details on asfotase alfa and its uses (together with the uses of other alkaline phosphatases) in treatment of NF1, see PCT Publication No. WO 2013/058833, the teachings of which are incorporated herein by reference in their entirety.

Manufacturing Process

The alkaline phosphatase protein described herein (e.g., asfotase alfa) may be produced by mammalian or other cells using routine methods known in the art. Such cells may be grown in culture dishes, flask glasses, or bioreactors. Specific processes for cell culture and producing recombinant proteins are known in the art, such as described in Nelson and Geyer, 1991 *Bioprocess Technol.* 13:112-143 and Rea et al., *Supplement to BioPharm International* March 2008, 20-25. Exemplary bioreactors include batch, fed-batch, and continuous reactors. In some embodiments, the alkaline phosphatase protein is produced in a fed-batch bioreactor.

Potential variability in the cell culture process physicochemical environment includes, for example, changes in pH, temperature, cell culture media composition, raw material lot-to-lot variation, medium filtration material, bioreactor scale difference, gassing strategy (air, oxygen, and carbon dioxide), etc. As disclosed herein, the glycosylation profiles of manufactured alkaline phosphatase protein may be affected by alterations in one or more parameters.

Development of Cell Culture Processes

For recombinant protein production in cell culture, the recombinant gene with the necessary transcriptional regulatory elements is first transferred to a host cell. Optionally, a second gene is transferred that confers to recipient cells a selective advantage. In the presence of the selection agent, which may be applied a few days after gene transfer, only those cells that express the selector gene survive. Two exemplary genes for selection are dihydrofolate reductase (DHFR), an enzyme involved in nucleotide metabolism, and glutamine synthetase (GS). In both cases, selection occurs in the absence of the appropriate metabolite (hypoxanthine and thymidine, in the case of DHFR, glutamine in the case of GS), preventing growth of nontransformed cells. In general, for efficient expression of the recombinant protein, it is not important whether the biopharmaceutical-encoding gene and selector genes are on the same plasmid or not.

Following selection, surviving cells may be transferred as single cells to a second cultivation vessel, and the cultures are expanded to produce clonal populations. Eventually, individual clones are evaluated for recombinant protein expression, with the highest producers being retained for further cultivation and analysis. From these candidates, one cell line with the appropriate growth and productivity characteristics is chosen for production of the recombinant protein. A cultivation process is then established that is determined by the production needs.

Cells

Any mammalian cell or non-mammalian cell type, which can be cultured to produce a polypeptide, may be utilized in accordance with the present disclosure. Non-limiting examples of mammalian cells that may be used include, e.g., Chinese hamster ovary cells +/−DHFR (CHO, Urlaub and Chasin, 1980 *Proc. Natl. Acad. Sci. USA*, 77:4216); BALB/c mouse myeloma line (NSO/1, ECACC Accession No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., 1977 *J. Gen Virol.*, 36:59); baby hamster kidney cells (BHK, ATCC CCL 10); mouse Sertoli cells (TM4, Mather, *Biol. Reprod.*, 23:243-251 (1980)); monkey kidney cells (CV1 ATCC CCL 70); African green monkey kidney cells (VERO-76, ATCC CRL-I 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 1982, *Annals N.Y. Acad. Sci.* 383:44-68); MRC 5 cells; FS4 cells; and a human hepatoma line (Hep G2). In a particular embodiment, culturing and expression of polypeptides and proteins occurs from a Chinese Hamster Ovary (CHO) cell line.

Additionally, any number of commercially and non-commercially available hybridoma cell lines that express polypeptides or proteins may be utilized in accordance with the present disclosure. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Downstream Processes

The term "downstream process(es)" used herein is generally referred to the whole or part(s) of the processes for recovery and purification of the alkaline phosphatases (e.g., asfotase alfa) produced from sources such as culture cells or fermentation broth, including the recycling of salvageable components and the proper treatment and disposal of waste.

Generally, downstream processing brings a product from its natural state as a component of a tissue, cell or fermentation broth through progressive improvements in purity and concentration. For example, the removal of insolubles may be the first step, which involves the capture of the product as a solute in a particulate-free liquid (e.g., separating cells, cell debris or other particulate matter from fermentation broth). Exemplary operations to achieve this include, e.g., filtration, centrifugation, sedimentation, precipitation, flocculation, electro-precipitation, gravity settling, etc. Additional operations may include, e.g., grinding, homogenization, or leaching, for recovering products from solid sources, such as plant and animal tissues. The second step may be a "product-isolation" step, which removes components whose properties vary markedly from that of the desired product. For most products, water is the chief impurity and isolation steps are designed to remove most of it, reducing the volume of material to be handled and concentrating the product. Solvent extraction, adsorption, ultrafiltration, and precipitation may be used alone or in combinations for this step. The next step is about product purification, which separates contaminants that resemble the product very closely in physical and chemical properties. Possible purification methods include, e.g., affinity, ion-exchange chromatography, hydrophobic interaction chromatography, mixed-mode chromatography, size exclusion, reversed phase chromatography, ultrafiltration-diafiltration, crystallization and fractional precipitation. The last step may be used for product polishing, which may end with packaging of the product in a form that is stable, easily transportable and convenient. Storage at 2-8° C., freezing at −20° C. to −80° C., crystallization, desiccation, lyophilization, freeze-drying and spray drying are exemplary methods in this final step. Depending on the product and its intended use, polishing may also sterilize the product and remove or deactivate trace contaminants (e.g., viruses, endotoxins, metabolic waste products, and pyrogens), which may compromise product safety.

Product recovery methods may combine two or more steps discussed herein. For example, expanded bed adsorption (EBA) accomplishes removal of insolubles and product isolation in a single step. For a review of EBA, see Kennedy, *Curr Protoc Protein Sci.* 2005 June; Chapter 8: Unit 8.8. In addition, affinity chromatography often isolates and purifies in a single step.

For a review of downstream processes for purifying a recombinant protein produced in culture cells, see Rea, 2008 Solutions for Purification of Fc-fusion Proteins. *BioPharm Int. Supplements* March 2:20-25. The downstream processes for alkaline phosphatases disclosed herein may include at least one, or any combination, of the following exemplary steps:

a harvest clarification process. In this step, the intact cells and cell debris are removed by sterile filtration and the product (i.e., the produced alkaline phosphatase) is recovered. Possible used solutions in this step may include a recovery buffer (e.g., 50 mM Sodium Phosphate, 100 mM NaCl, pH 7.50);

a post-harvest ultrafiltration (UF) and/or diafiltration (DF) process. The purpose for this step is for concentration and buffer dilution. Exemplary steps for the UF process include, e.g., pre-use cleaning/storage of the filter membrane, post-clean/post-storage flush, equilibration (e.g., with a buffer containing 50 mM Sodium Phosphate, 100 mM NaCl, pH 7.50), loading, concentration, dilution/flush/recovery (e.g., with a buffer containing 50 mM Sodium Phosphate, 100 mM NaCl, pH 7.50), and post-use flush/clean/storage of the filter membrane;

a solvent/detergent viral inactivation process to chemically inactivate viral particles. Exemplary solvent/detergent may contain 10% Polysorbate 80, 3% TNBP, 50 mM Sodium Phosphate, and 100 mM NaCl;

a certain type of column chromatography to further purify the product and/or separate the impurities/contaminants, such as gel filtration chromatography, ion exchange chromatography, reversed-phase chromatography (RP), affinity chromatography, expanded bed adsorption (EBA), mixed-mode chromatography and hydrophobic interaction chromatography (HIC). Affinity capture process, e.g., Protein A chromatography, may be used to capture the product (i.e., the alkaline phosphatase, such as asfotase alfa). For example, a process of GE Healthcare Mab Select SuRe Protein A chromatography may be used. HIC chromatography may use Butyl Sepharose or CAPTO® Butyl agarose columns. Exemplary buffers and solutions used in a Protein A chromatography include, e.g., equilibration/wash buffer (e.g., 50 mM Sodium Phosphate, 100 mM NaCl, pH 7.50), elution buffer (e.g., 50 mM Tris, pH 11.0), strip buffer (e.g., 100 mM Sodium Citrate, 300 mM NaCl, pH 3.2), flushing buffer, cleaning solution (e.g., 0.1 M NaOH), etc. Exemplary buffers and solutions used in a CAPTO® Butyl agarose HIC process include, e.g., loading dilution buffer/pre-equilibration buffer (e.g., 50 mM sodium phosphate, 1.4 M sodium sulfate, pH 7.50), equilibration buffer/wash buffer/elution buffer (e.g., all containing sodium phosphate and sodium sulfate), strip buffer (e.g., containing sodium phosphate), etc. Exemplary buffers and solutions used in a Butyl HIC process include, e.g., loading dilution buffer/pre-equilibration buffer (e.g., 10 mM HEPES, 2.0 M ammonium sulfate, pH 7.50), equilibration buffer/wash buffer(s)/elution buffer (e.g., all containing sodium phosphate or HEPES and ammonium sulfate), strip buffer (e.g., containing sodium phosphate);

a post-HIC UF/DF process for, e.g., product concentration and/or buffer exchange. Exemplary buffers and solutions used in this process include, e.g., equilibration buffer (e.g., 20 mM Sodium Phosphate, 100 mM NaCl, pH 6.75), diafiltration buffer (20 mM Sodium Phosphate, 100 mM NaCl, pH 6.75), etc.;

a viral reduction filtration process to further remove any viral particles;

a mixed-mode chromatography, such as CAPTO® Adhere agarose chromatography. Commercially available mixed-mode materials include, e.g., resins containing hydrocarbyl amine ligands (e.g., PPA Hypercel and HEA Hypercel from Pall Corporation, Port Washington, N.Y.), which allow binding at neutral or slightly basic pH, by a combination of hydrophobic and electrostatic forces, and elution by electrostatic charge repulsion at low pH (see Brenac et al., 2008 *J Chromatogr A.* 1177:226-233); resins containing 4-mercapto-ethyl-pyridine ligand (MEP Hypercel, Pall Corporation), which achieves hydrophobic interaction by an aromatic residue and the sulphur atom facilitates binding of the target protein by thiophilic interaction (Lees et al., 2009 *Bioprocess hit.* 7:42-48); resins such as CAPTO® MMC mixed-mode chromatography and CAPTO® adhere agarose chromatography (GE Healthcare, Amersham, UK) containing ligands with hydrogen bonding groups and aromatic residues in the proximity of ionic groups, which leads to the salt-tolerant adsorption of proteins at different conductivities (Chen et al., 2010 *J Chromatogr A.* 1217:216-224); and other known chromatography materials, such as affinity resins with dye ligands, hydroxyapatite, and some ion-exchange resins (including, but not limited to, Amberlite CG 50 (Rohm & Haas, Philadelphia, Pa.) or Lewatit CNP 105 (Lanxess, Cologne, Del.). For an exemplary agarose HIC chromatography step, exemplary buffers and solutions used in this process include, e.g., pre-equilibration buffer (e.g., 0.5 M Sodium Phosphate, pH 6.00), equilibration/wash buffer (e.g., 20 nM Sodium Phosphate, 440 mM NaCl, pH 6.50), load titration buffer (e.g., 20 mM Sodium Phosphate, 3.2 M NaCl, pH 5.75), pool dilution buffer (e.g., 25 mM Sodium Phosphate, 150 mM NaCl, pH 7.40), and strip buffer (0.1 M Sodium Citrate, pH 3.20;

a virus filtration for viral clearance (by, e.g., size exclusion). Exemplary buffers and solutions used in this process include, e.g., pre-use and post-product flush buffer (e.g., 20 mM Sodium Phosphate, 100 mM NaCl, pH 6.75);

a formulation (may comprise UF/DF process for, e.g., concentration and/or buffer exchange) process. Exemplary buffers and solutions used in this process include, e.g., filter flush/equilibration/diafiltration/recovery buffer (e.g., 25 mM Sodium Phosphate, 150 mM NaCl, pH 7.40); and a bulk fill process comprising sterile filtration (exemplary filters are Millipak 60 or Equivalent sized PVDF filters (EMD Millipore, Billerica, Mass.).

Hydrophobic interaction chromatography (HIC) is a bioseparation tool in the purification of proteins. HIC separates molecules based on their hydrophobicity under relatively less denaturing conditions. For more details of HIC, see Hjerten 1981 *Methods Biochem Anal.,* 27:89-108 and Periat et al., 2015 *J Sep Sci.* 38:357-367. Generally, proteins can be separated and, thus, purified, from a preparation or solution containing such proteins and at least one impurity, through a HIC column due to hydrophobic interactions between non-polar regions on the surface of the proteins and insoluble, immobilized hydrophobic groups on the HIC column matrix. The salt in the preparation or solution reduces the solvation of the proteins. As solvation decreases, hydrophobic regions that become exposed are adsorbed by the matrix. The more hydrophobic the molecule, the less salt is needed to promote binding. Usually a high salt concentration is used for proteins to bind to the HIC column matrix, while a decreasing salt gradient is used to elute the bound proteins from the column in order of increasing hydrophobicity. Elution may also be assisted by the addition of mild organic modifiers or detergents to the elution buffer. For example, between about 0.7 and about 2 M ammonium sulfate and between about 1.0 and about 4.0 M NaCl salt concentration may be used for protein purification through HIC columns.

All references cited herein are incorporated by reference in their entirety.

Although the foregoing disclosure has been described in some detail by way of illustration and example for purposes of clarity of understanding, it is apparent to those skilled in the art that certain minor changes and modifications will be practiced. Therefore, the description and examples should not be construed as limiting the scope of the disclosure.

EXAMPLES

Example 1

General Manufacturing Process for Asfotase Alfa

As described herein, an optional manufacturing process to produce alkaline phosphatases (e.g., asfotase alfa (5TNALP-Fc-$D_{10}$)) has been developed.

Stable CHO cell lines expressing asfotase alfa were developed using a gene expressin system, e.g., the GS ore the DHFR gene expression system. Secondary clones were derived from high producing primary clones in a single round of limited dilution cloning and a final cell line was selected.

An exemplary manufacturing process is described herein. A vial of the Master Cell Bank was thawed and the entire volume of the vial was re-suspended. The entire volume was transferred to a 250 mL shake flask for growth. Samples were taken daily for counts and viability tests (also for all following expansion steps). Cells were expanded through several steps and inoculated into a 1,000 L seed bioreactor (N-3 low level), a 1,000 L seed bioreactor (N-2 high level), and a 4,000 L seed bioreactor (N-1) and then a 20,000 L production bioreactor. After production of asfotase alfa, the harvest clarification process was employed to remove intact cells and cell debris by centrifugation, depth filtration and sterile filtration. The harvest was then ultrafiltered (Post Harvest UF) for concentration and buffer dilution. Further processes included, for example, viral inactivation (to chemically inactivate viral particles), MabSelect Sure Protein A chromatography, ammonium sulfate addition, hydrophobic interaction chromatography (HIC, using either Butyl SEPHAROSE® HP resin or CAPTO® Butyl HIC resin), post HIC UF/DF (UF/DF2), agarose mixed-mode chromatography, virus filtration (by size exclusion), formulation (UF/DF3), and bulk fill.

Multiple manufacturing processes were performed including, for example, 2,000 L-scale processes and the following scale-up to the 20,000 L production scale. As tested, the produced asfotase alfa had comparable characteristics across all batches between the 2,000 L and 20,000 L scales.

Example 2

Impact of Metal Content in the Ammonium Sulfate on the Specific Activity in the HIC Process Step In an exemplary process for manufacturing asfotase alfa, the downstream product purification contained three chromatography steps, designed to remove impurities and contaminants. Following a solvent/detergent viral inactivation step, the produced asfotase alfa was purified through a MabSelect SuRe Protein A chromatography. The MAbSelect pool was adjusted for conductivity with 40 mM 4-(2-hydroxyethyl)-1-piperazineethanesulfonic acid (HEPES)/ 2.0 M ammonium sulphate (AMS), pH 7.5. The adjusted MabSelect pool was then processed through the Hydrophobic Interaction Chromatography (HIC) step, which utilized resins, such as Butyl SEPHAROSE® HP resin or agarose HIC resin (e.g., GE Healthcare CAPTO® Butyl agarose resin (Supplier Catalog Number: 17-5459), Pittsburgh, Pa.), to further purify the produced asfotase alfa. Upon completion of the HIC step, the in-process product was buffer-exchanged (thus removing AMS) and filtered through a virus reduction filter, prior to processing over the mixed mode chromatography column and the following steps. Some exemplary buffers/solutions used in the downstream processes include, load dilution buffer (40 mM HEPES, 2.0 M Ammonium Sulfate, pH 7.5), pre-use sanitization buffer (0.5 M Sodium hydroxide), pre-conditioning buffer (10 mM Sodium phosphate pH 5.2), equilibration buffer (20 mM HEPES, 1.1 M ammonium sulfate, pH 7.50), post-load wash 1 buffer (20 mM HEPES, 1.1 M ammonium sulfate, pH 7.50), post-load wash 2 buffer (20 mM HEPES, 0.95 M ammonium sulfate, pH 7.50), elution buffer (25 mM Sodium phosphate, 0.5 M ammonium sulfate, pH 7.50), post elution wash (10 mM Sodium phosphate, pH 5.20), cleaning buffer (1.0 M Sodium hydroxide), and storage buffer (0.1 M Sodium hydroxide).

High metal content, for example, in the AMS, was identified as the root cause for the low specific activity of the produced asfotase alfa on a number of manufacturing batches. For example, the specific activity of the asfotase alfa bulk drug substance (BDS) was from about 620 to about 1250 U/mg, while values of specific activity in the HIC pool may range from about 744 to about 1078 U/mg. Two batches of produced asfotase alfa had lower than expected specific activities (432 and 469 U/mg for asfotase alfa in the HIC pool and 419 and 452 U/mg for asfotase alfa in the final bulk drug substance (BDS)). Preliminary investigation showed that the nickel (Ni) metal content in BDS for these two batches was about 50 to 100 fold higher than other lots. The high nickel content was eventually traced back to one lot of ammonium sulfate (lot X) used in the manufacture of these two batches.

Figure 1:
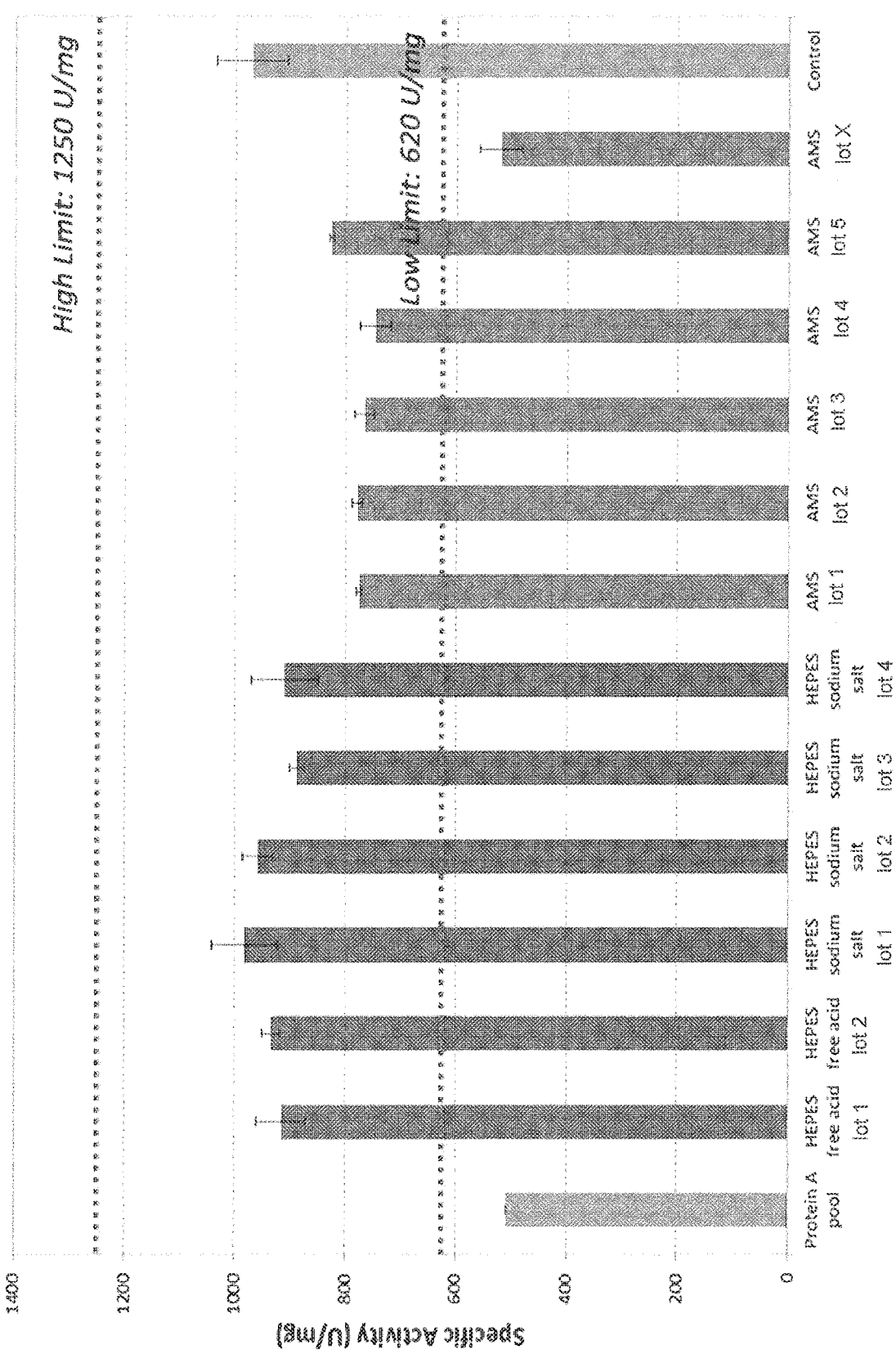
FIG. 1 is a graph comparing the specific activity of the produced asfotase alfa purified with different lots of buffer components used in the Hydrophobic Interaction Chromatography (HIC) step, such as two lots of 4-(2-hydroxyethyl)-1-piperazineethanesulfonic acid (HEPES) free acid, four lots of HEPES sodium salt, and six test lots of ammonium sulfate (AMS). The "Protein A pool" column shows the specific activity of asfotase alfa after the initial purification step through Protein A chromatography. The "control" column shows the specific activity of asfotase alfa purified using a "control" lot of AMS that shows acceptable activity (620-1250 U/mg).
Figure 2A:
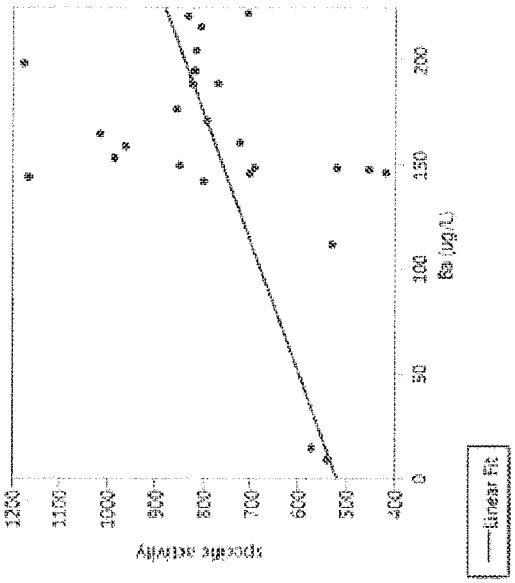
FIGS. 2A-2C are graphs showing the linear correlation between the concentration of metal ions B (FIG. 2A), Ba (FIG. 2B), and Co (FIG. 2C) in the AMS used in the HIC step and the specific activity of the produced asfotase alfa in the final BDS. Data from a total of 26 manufacturing batches were used in this analysis. The specific activity in view of B was calculated to be equal to 510.11+0.54×[B], while $R^2=0.3$ and the p value=0.01. The specific activity in view of Ba was calculated to be equal to 521.20+1.61×[Ba], while $R^2=0.2$ and the p value=0.02. The specific activity in view of Co was calculated to be equal to 976.16−25.45×[Co], while $R^2=0.7$ and the p value<0.001.
Figure 2B:
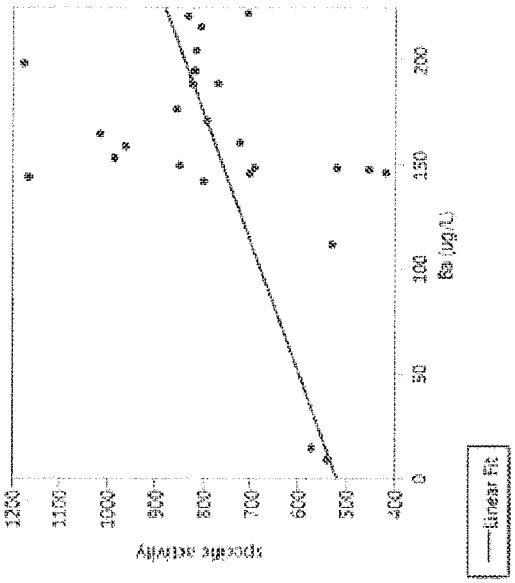
Figure 2C:
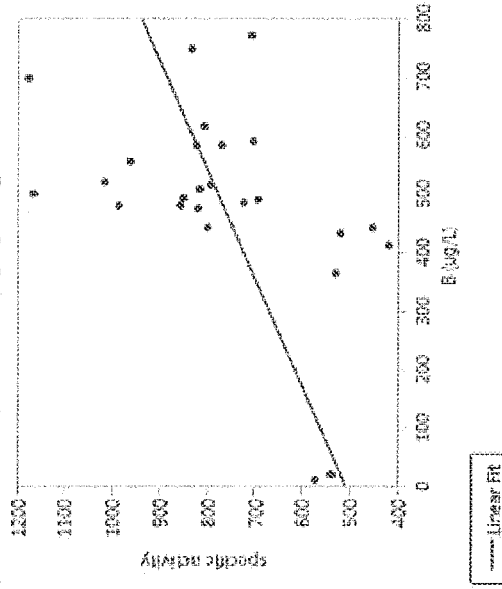
Figure 2C:
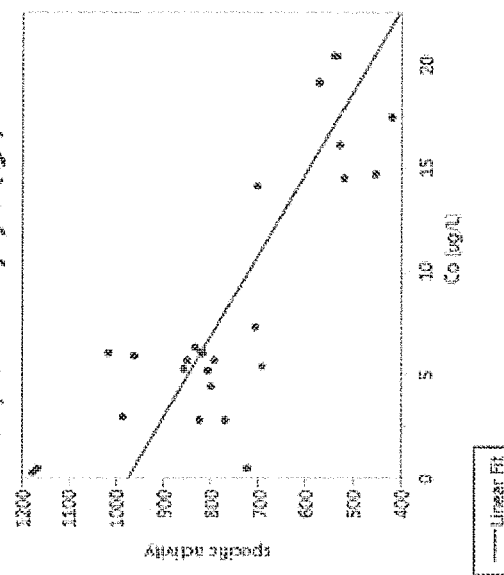
Figure 4A:
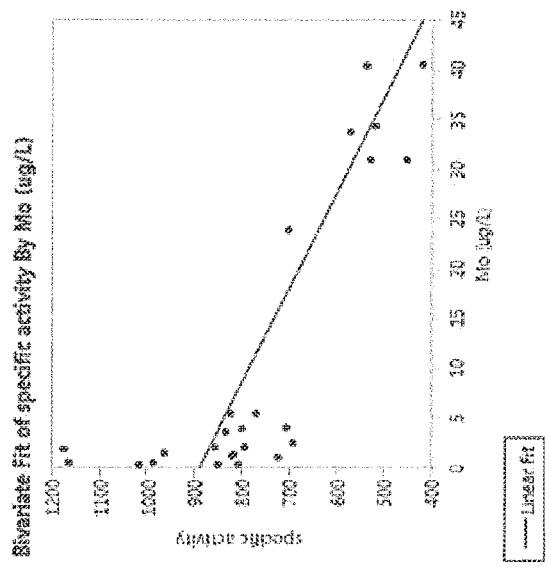
FIGS. 4A-4C are graphs showing the linear correlation between the concentration of metal ions Ir (FIG. 4A), Mo (FIG. 4B), and Nb (FIG. 4C) in the AMS used in the HIC step and the specific activity of the produced asfotase alfa in the final BDS. The specific activity in view of Ir was calculated to be equal to 857.02−1401.88×[Ir], while $R^2=0.2$ and the p value=0.01. The specific activity in view of Mo was calculated to be equal to 891.12−10.46×[Mo], while $R^2=0.7$ and the p value<0.001. The specific activity in view of Nb was calculated to be equal to 819.28−4537.83×[Nb], while $R^2=0.2$ and the p value=0.03.
Figure 4B:
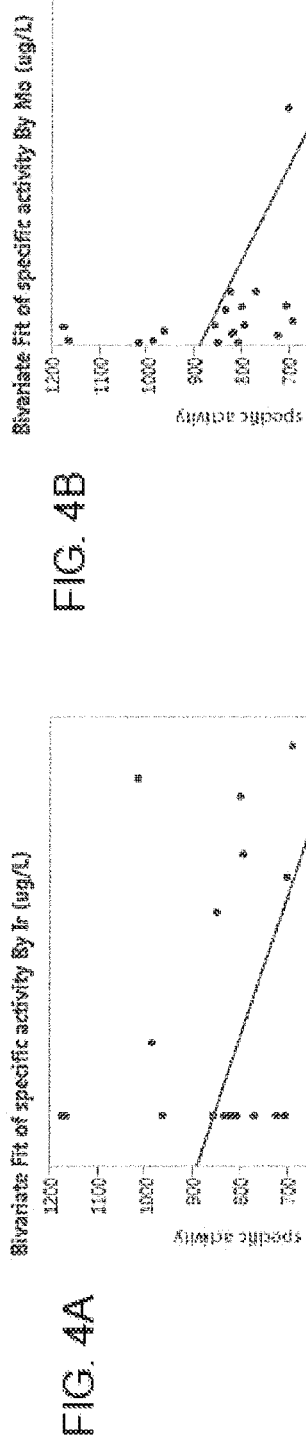
Figure 4C:
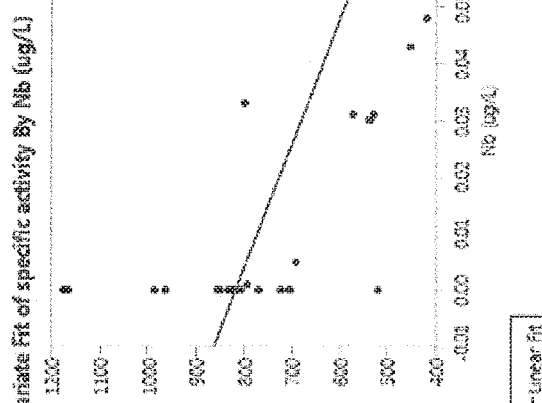
Figure 5B:
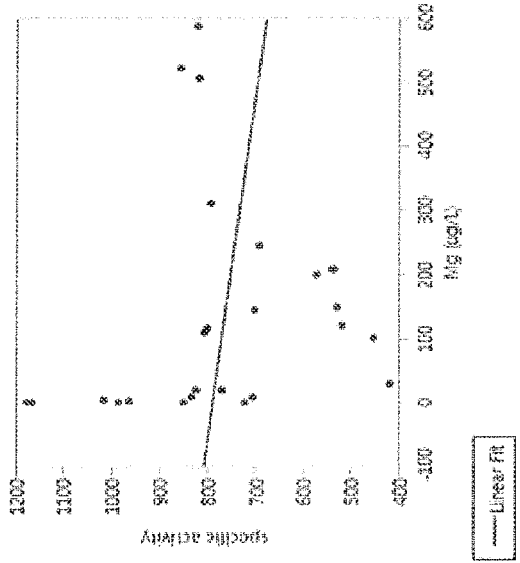
FIGS. 5A-5C are graphs showing the linear correlation between the concentration of metal ions Hg (FIG. 5A), Mg (FIG. 5B), and Mn (FIG. 5C) in the AMS used in the HIC step and the specific activity of the produced asfotase alfa in the final BDS. The specific activity in view of Hg was calculated to be equal to 801.39−8290.23×[Hg], while $R^2=0.1$ and the p value=0.21. The specific activity in view of Mg was calculated to be equal to 790.33−0.18×[Mg], while $R^2=0.1$ and the p value=0.44. The specific activity in view of Mn was calculated to be equal to 863.31−1.71×[Mn], while $R^2=0.4$ and the p value<0.001.
Figure 5C:
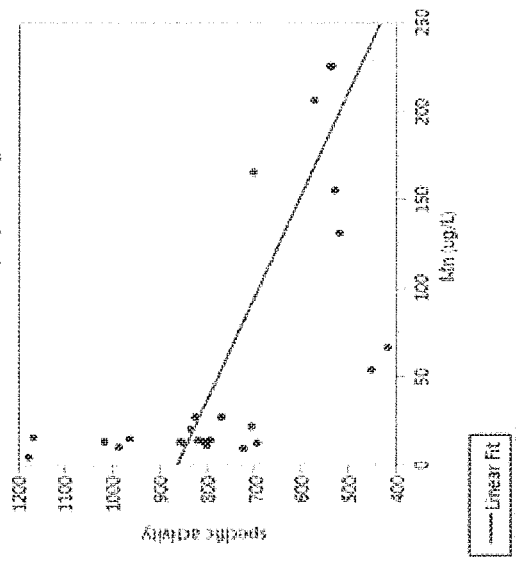
Figure 5A:
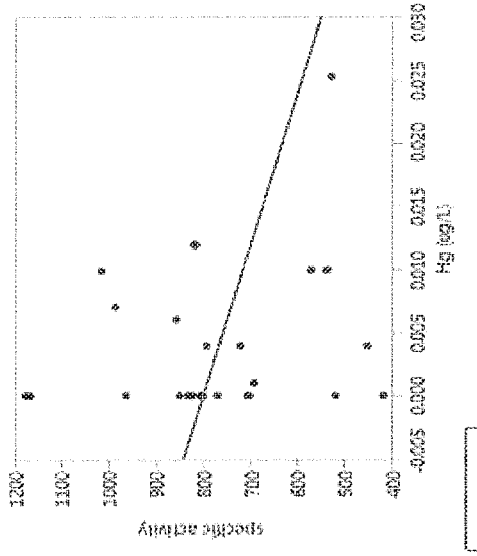
Figure 6A:
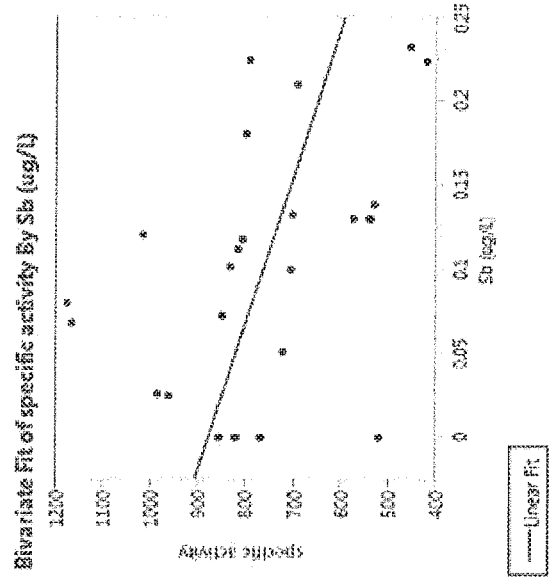
FIGS. 6A-6C are graphs showing the linear correlation between the concentration of metal ions Rh (FIG. 6A), Sb (FIG. 6B), and Ni (FIG. 6C) in the AMS used in the HIC step and the specific activity of the produced asfotase alfa in the final BDS. The specific activity in view of Rh was calculated to be equal to 808.17−2835.92×[Rh], while $R^2=0.2$ and the p value=0.03. The specific activity in view of Sb was calculated to be equal to 879.41×1146.69×[Sb], while $R^2=0.2$ and the p value=0.03. The specific activity in view of Ni was calculated to be equal to 842.64−0.36×[Ni], while $R^2=0.5$ and the p value<0.001.
Figure 6B:
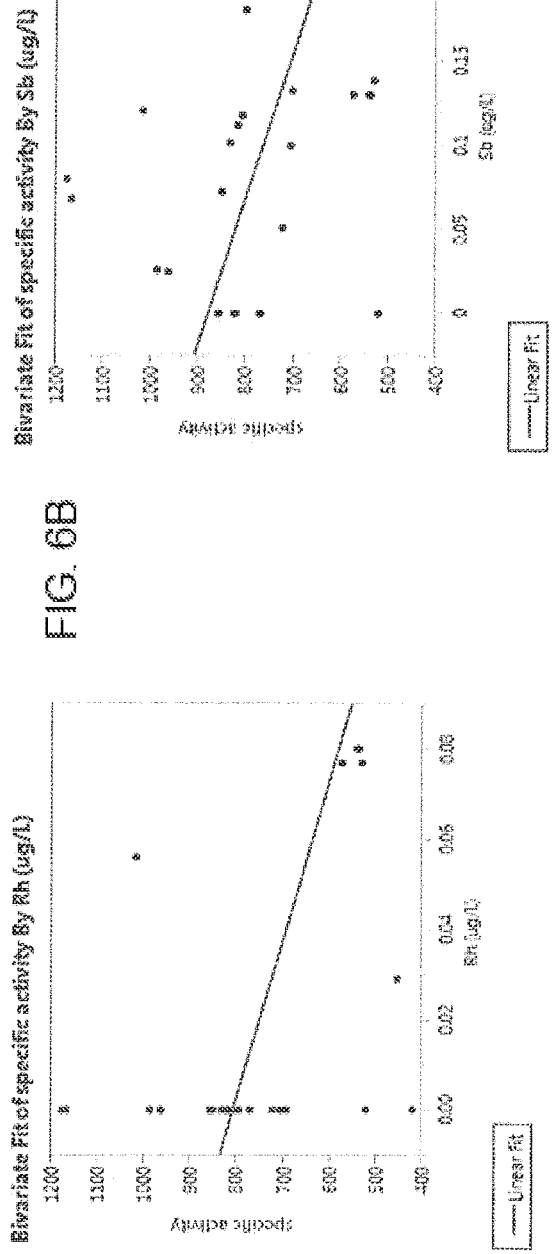
Figure 6C:
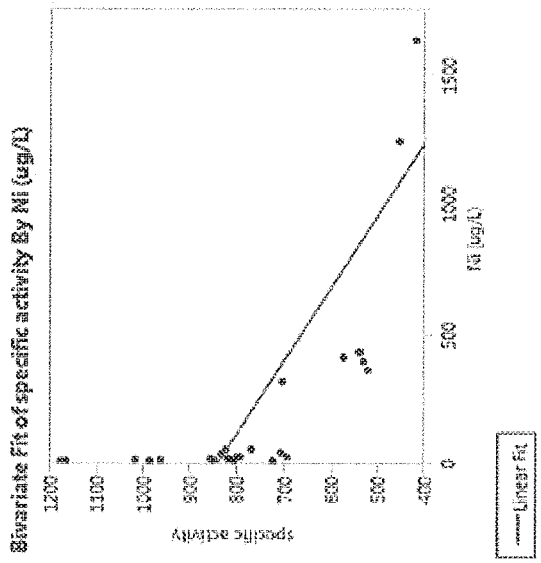

Studies were then performed (using either a 96-well plate purification method and a 1-cm column purification method) in an exemplary Butyl SEPHAROSE® agarose gel solid phase HP process with different HIC solutions made from various buffer components to analyze the impact of each solution component on the specific activity of asfotase alfa. The HIC solution components suspected to have introduced the metal contamination included, at least, 4-(2-hydroxyethyl)-1-piperazineethanesulfonic acid (HEPES) free acid, HEPES sodium salt, and ammonium sulfate. In the first part of the study, the impact of different lots of HEPES free acid, HEPES sodium salt, and ammonium sulfate in the HIC Load Dilution buffer, the HIC Equilibration/Post-Load Wash 1 buffer and the HIC Post-Load Wash 2 buffer was tested. All lots led to specific activity within the limits of 620 to 1250 U/mg, except for a specific lot of ammonium sulfate (lot X, in which the specific activity of the produced asfotase alfa was about 440 U/mg, as shown in FIG. 1). In the second part of the study, the impact of different ammonium sulfate lots was tested in the HIC Elution buffer, while the HIC Load Dilution buffer, the HIC Equilibration/Post-Load Wash 1 buffer and the HIC Post-Load Wash 2 buffer were prepared using control buffer components. Specific activity results from the HIC pool for all these runs were within the limits of 620 to 1250 U/mg. No impact was seen using ammonium sulfate lot X in the elution buffer alone. Thus, these data showed that the ammonium sulfate lots had an impact (at least when used in the preparation of the loading dilution buffer, the HIC equilibration buffer, and/or the HIC post-load wash buffer) on the specific activity of the produced asfotase alfa in the HIC pool. Specifically, the lot with the highest nickel content (i.e., lot X, which had about 100 fold higher nickel content than other lots of ammonium sulfate) had the lowest specific activity for the produced asfotase alfa in the HIC pool.

Additional studies were further carried out to test the impact of different metal ions in the AMS on the specific activity of the produced asfotase alfa in the HIC pool and in the final BDS. In an exemplary study, a total of 26 BDS batches were used for analysis with JMP software version 11. Table 1 summarizes exemplary statistics of the different metal levels measured in the AMS of the HIC Load Dilution buffer (by ICP-MS) along with the specific activity and the Zinc molar ratio of the BDS. The metal content in the AMS is expressed in µg/L in a 2 M solution. The data showed that specific activity in the BDS ranged from about 419 U/mg to about 1176 U/mg (previously set specification=620-1200 U/mg). The zinc molar ratio in BDS ranged from about 1.3 mole/mole to about 3.4 mole/mole. The data allow an evaluation of which metals are most abundant in the AMS. The data also show that the ranges and coefficient of variation (CV) observed for some of the metals was much higher than other metal levels, indicating fluctuations in levels of some metals in AMS.

Bivariate analysis was performed for each metal detected in the AMS and used in the load dilution buffer, to identify which metals have a statistical impact on the specific activity of the asfotase alfa (BDS). FIGS. 2A-2C, 3A-3C, 4A-4C, 5A-5C, 6A-6C, and 7A-7C show analytic results for some exemplary metal ions. Those metal ions, which have a p value<0.05 and $R^2 \geq 0.4$ (meaning that the model explains at least 40% of the observed variation) under this analysis, were selected for further analysis. Other metal ions, such as Ag, Al, As, Au, Ca, Cd, Ge, In, K, Pb, Pt, Ru, Sn, Ti, Tl, V, Y, Zn, and Zr, were also analyzed. Their data are not shown here since there was no strong linear correlation, i.e., none gave a p value<0.05 and $R^2 \geq 0.4$. Among them, the metal ions having a negative impact on specific activity of asfotase alfa (i.e., increasing their concentrations in the AMS decreased the specific activity of asfotase alfa) were Gold (Au), Calcium (Ca), Germanium (Ge), Chromium (Cr), Magnesium (Mg), Rhodium (Rh), Antimony (Sb), Platinum (Pt), Ruthenium (Ru), Scandium (Sc), Palladium (Pd), Vanadium (V), and Zirconium (Zr). The metal ions having a positive impact on specific activity of asfotase alfa (i.e., increasing their concentrations in the AMS increased the

TABLE 1

Statistics Summary of the metal concentrations in the AMS of the HIC Load Dilution Buffer and Bulk Drug Substance (BDS)

| Parameter | N | Mean | Std Dev | Min | Max | Range | CV | Median |
|---|---|---|---|---|---|---|---|---|
| Specific activity (U/mg) | 26 | 764.654 | 200.185 | 419.000 | 1176.000 | 757.000 | 26.180 | 796.500 |
| Zn in BDS (mol Zn/mol product) | 25* | 2.13 | 0.48 | 1.33 | 3.36 | 2.03 | 22.33 | 1.98 |
| Ag (µg/L) | 26 | 0.019 | 0.011 | 0.001 | 0.041 | 0.040 | 55.989 | 0.023 |
| Al (µg/L) | 26 | 37.447 | 35.343 | 2.700 | 140.965 | 138.265 | 94.383 | 29.473 |
| As (µg/L) | 26 | 75.183 | 28.851 | 0.032 | 93.328 | 93.296 | 38.375 | 85.922 |
| B (µg/L) | 26 | 469.587 | 193.001 | 13.326 | 771.004 | 757.678 | 41.100 | 484.596 |
| Ba (µg/L) | 26 | 150.645 | 59.123 | 9.144 | 222.021 | 212.877 | 39.247 | 151.276 |
| Co (µg/L) | 26 | 8.293 | 6.408 | 0.262 | 20.369 | 20.107 | 77.271 | 5.896 |
| Au (µg/L) | 26 | 0.354 | 0.123 | 0.000 | 0.444 | 0.444 | 34.824 | 0.438 |
| Ca (µg/L) | 26 | 479.892 | 324.891 | 102.011 | 1250.000 | 1147.989 | 67.701 | 395.877 |
| Cd (µg/L) | 26 | 0.316 | 0.215 | 0.065 | 0.857 | 0.792 | 67.926 | 0.241 |
| Ge (µg/L) | 26 | 2.684 | 1.428 | 1.568 | 8.823 | 7.255 | 53.214 | 3.000 |
| In (µg/L) | 26 | 0.091 | 0.013 | 0.081 | 0.139 | 0.058 | 14.404 | 0.082 |
| K (µg/L) | 26 | 773.562 | 2065.430 | 130.000 | 10100.000 | 9970.000 | 267.002 | 147.762 |
| Cr (µg/L) | 26 | 66.056 | 81.335 | 0.891 | 347.572 | 346.681 | 123.130 | 41.824 |
| Cu (µg/L) | 26 | 12.510 | 12.401 | 2.087 | 47.819 | 45.732 | 99.134 | 7.292 |
| Fe (µg/L) | 26 | 121.858 | 85.088 | 2.900 | 276.131 | 273.231 | 69.825 | 105.566 |
| Ir (µg/L) | 26 | 0.120 | 0.024 | 0.100 | 0.190 | 0.090 | 19.912 | 0.110 |
| Mo (µg/L) | 26 | 12.088 | 15.539 | 0.444 | 40.506 | 40.062 | 128.555 | 3.068 |
| Nb (µg/L) | 26 | 0.044 | 0.014 | 0.031 | 0.061 | 0.030 | 32.975 | 0.032 |
| Hg (µg/L) | 26 | 0.010 | 0.001 | 0.010 | 0.012 | 0.002 | 5.880 | 0.010 |
| Mg (µg/L) | 26 | 140.603 | 171.855 | 4.312 | 586.726 | 582.414 | 122.227 | 106.157 |
| Mn (µg/L) | 26 | 57.611 | 74.518 | 5.029 | 225.885 | 220.856 | 129.348 | 16.050 |
| Rh (µg/L) | 26 | 0.069 | 0.010 | 0.055 | 0.078 | 0.023 | 15.205 | 0.077 |
| Sb (µg/L) | 26 | 0.091 | 0.074 | 0.013 | 0.232 | 0.219 | 81.249 | 0.079 |
| Ni (µg/L) | 26 | 217.538 | 395.021 | 8.464 | 1628.459 | 1619.995 | 181.587 | 27.978 |
| Pb (µg/L) | 26 | 1.201 | 2.089 | 0.048 | 9.309 | 9.261 | 173.954 | 0.516 |
| Pt (µg/L) | 26 | 0.091 | 0.043 | 0.051 | 0.243 | 0.192 | 46.846 | 0.081 |
| Ru (µg/L) | 26 | 0.029 | 0.023 | 0.001 | 0.059 | 0.058 | 78.770 | 0.045 |
| Sc (µg/L) | 26 | 0.399 | 0.040 | 0.343 | 0.434 | 0.091 | 10.045 | 0.430 |
| Si (µg/L) | 26 | 154.377 | 66.031 | 38.000 | 304.756 | 266.756 | 42.773 | 153.030 |
| Pd (µg/L) | 26 | 0.178 | 0.092 | 0.062 | 0.253 | 0.191 | 51.760 | 0.250 |
| Sn (µg/L) | 26 | 0.100 | 0.052 | 0.056 | 0.160 | 0.104 | 51.523 | 0.057 |
| Ti (µg/L) | 26 | 2.489 | 0.256 | 1.996 | 3.031 | 1.035 | 10.275 | 2.506 |
| Tl (µg/L) | 26 | 0.142 | 0.141 | 0.019 | 0.555 | 0.536 | 99.596 | 0.073 |
| V (µg/L) | 26 | 0.484 | 0.144 | 0.000 | 0.586 | 0.586 | 29.628 | 0.580 |
| Y (µg/L) | 26 | 1.199 | 0.456 | 0.140 | 1.743 | 1.603 | 38.009 | 1.250 |
| Zn (µg/L) | 26 | 292.186 | 251.105 | 54.551 | 889.310 | 834.759 | 85.940 | 186.443 |
| Zr (µg/L) | 26 | 3.482 | 1.330 | 1.413 | 6.714 | 5.301 | 38.187 | 3.240 |

N represents the total number of AMS lots tested for each parameter.
*refers to an analysis (i.e., Zn concentration) in which only 25 BDS samples were tested.

specific activity of asfotase alfa) were Silver (Ag), Aluminum (Al), Arsenic (As), Boron (B), Barium (Ba), Cadmium (Cd), Indium (In), Potassium (K), iron (Fe), Iridium (Ir), Niobium (Nb), Mercury (Hg), Lead (Pb), Tin (Sn), Titanium (Ti), Thallium (Tl), and Yttrium (Y).

Figure 7A:
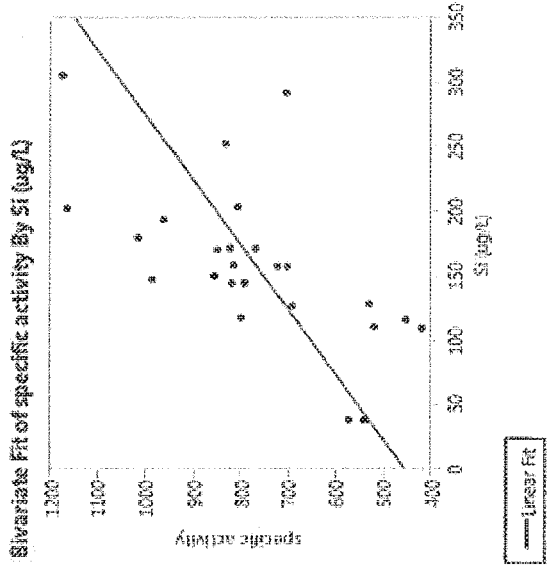
FIGS. 7A-7C are graphs showing the linear correlation between the concentration of metal ions Sc (FIG. 7A), Si (FIG. 7B), and Pd (FIG. 7C) in the AMS used in the HIC step and the specific activity of the produced asfotase alfa in the final BDS. The specific activity in view of Sc was calculated to be equal to 806.55−487.79×[Sc], while $R^2=0.2$ and the p value=0.04. The specific activity in view of Si was calculated to be equal to 456.34+1.99×[Si], while $R^2=0.4$ and the p value<0.001. The specific activity in view of Pd was calculated to be equal to 815.22−1074.17×[Pd], while $R^2=0.2$ and the p value=0.01.
Figure 7B:
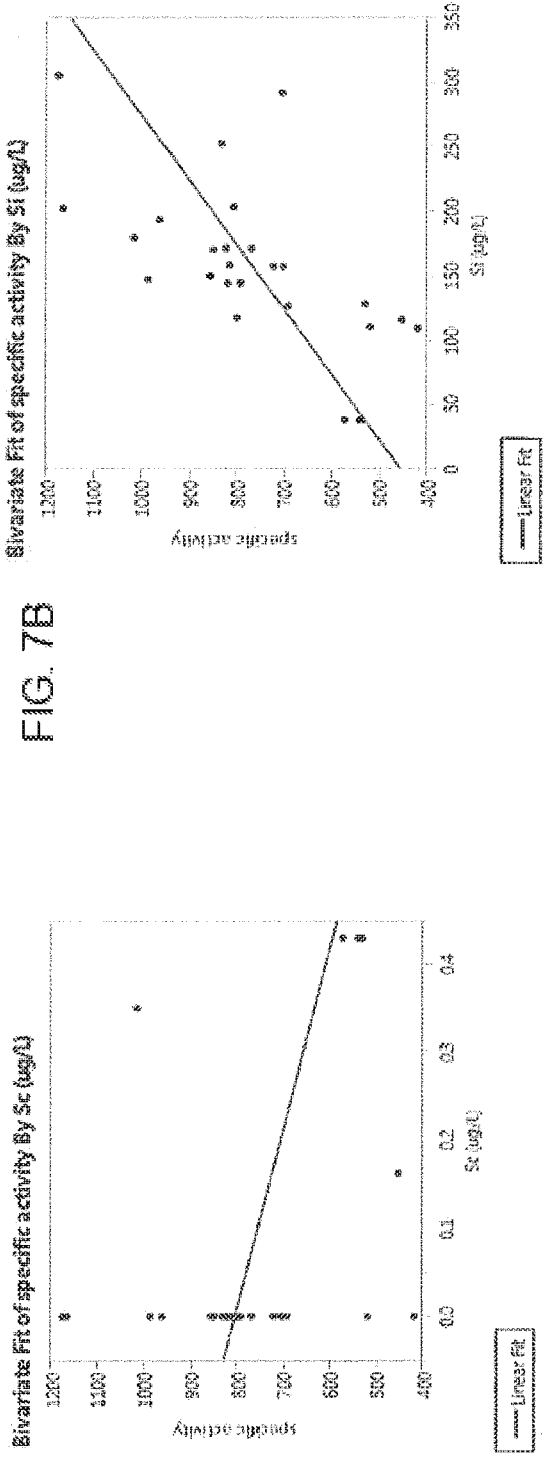
Figure 7C:
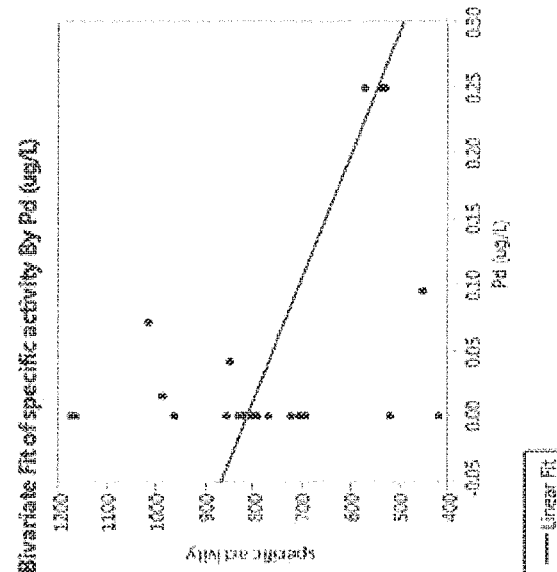

As shown in FIGS. 2A-2C, 3A-3C, 4A-4C, 5A-5C, 6A-6C, and 7A-7C, the metals that may have a negative impact on BDS specific activity (i.e., increasing their concentrations in the AMS decreased specific activity) were identified as Cobalt (Co), Chromium (Cr), Copper (Cu), Molybdenum (Mo), Manganese (Mn), and Nickel (Ni). Interestingly, Silicon (Si) seemed to show a positive impact on BDS specific activity (FIG. 7B). Under this analysis Zinc (Zn) was also found to have a weak correlation in positively impacting BDS specific activity.

Figure 8:
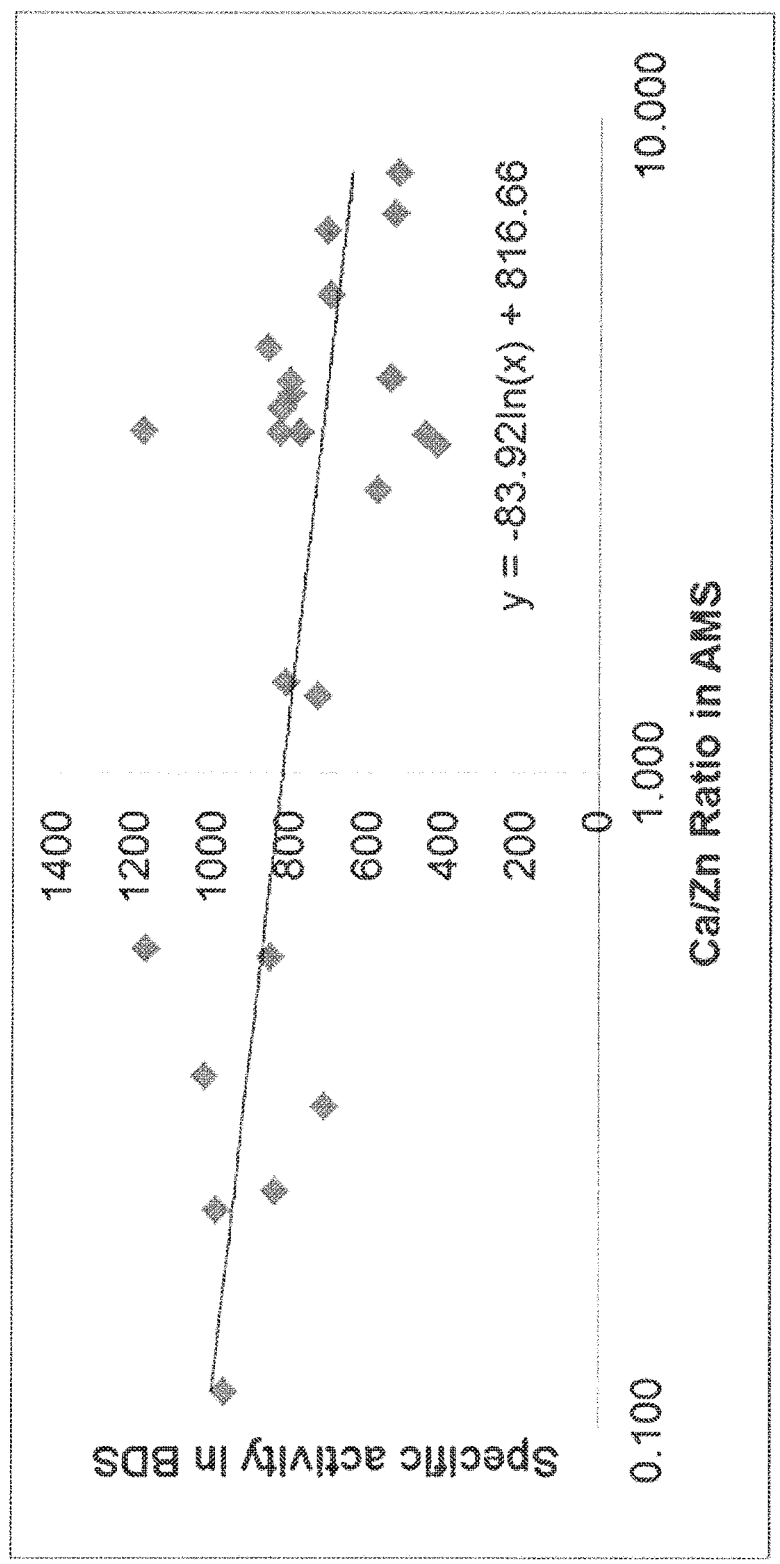
FIG. 8 is a graph showing the correlation between the Ca/Zn molar ratio in the AMS used in the HIC step and the specific activity in the final BDS. The specific activity was calculated to be equal to 816.66−83.92×ln (Ca/Zn molar ratio), while $R^2=0.27$.
Figure 9:
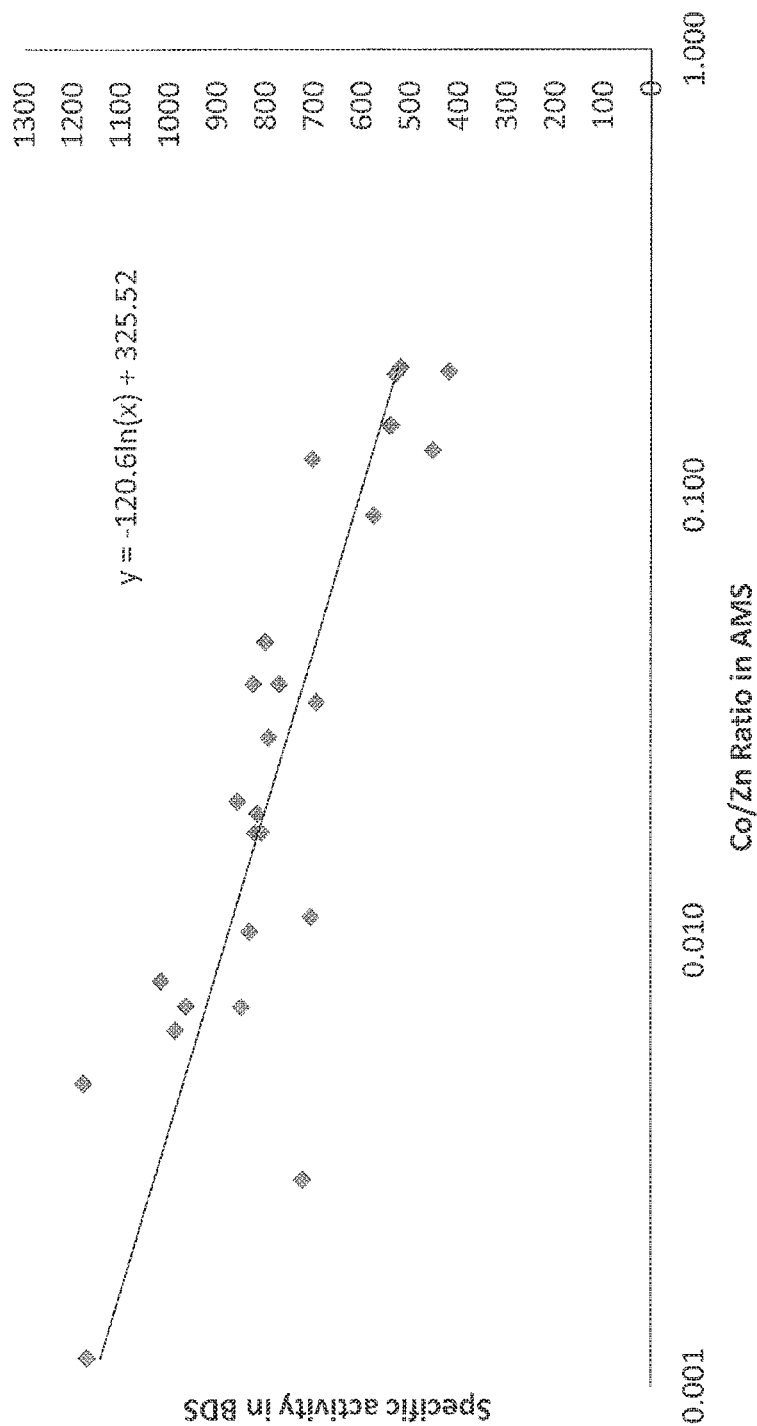
FIG. 9 is a graph showing the correlation between the Co/Zn molar ratio in the AMS used in the HIC step and the specific activity in the final BDS. The specific activity was calculated to be equal to 325.52−120.6×ln (Co/Zn molar ratio), while $R^2=0.74$.
Figure 10:
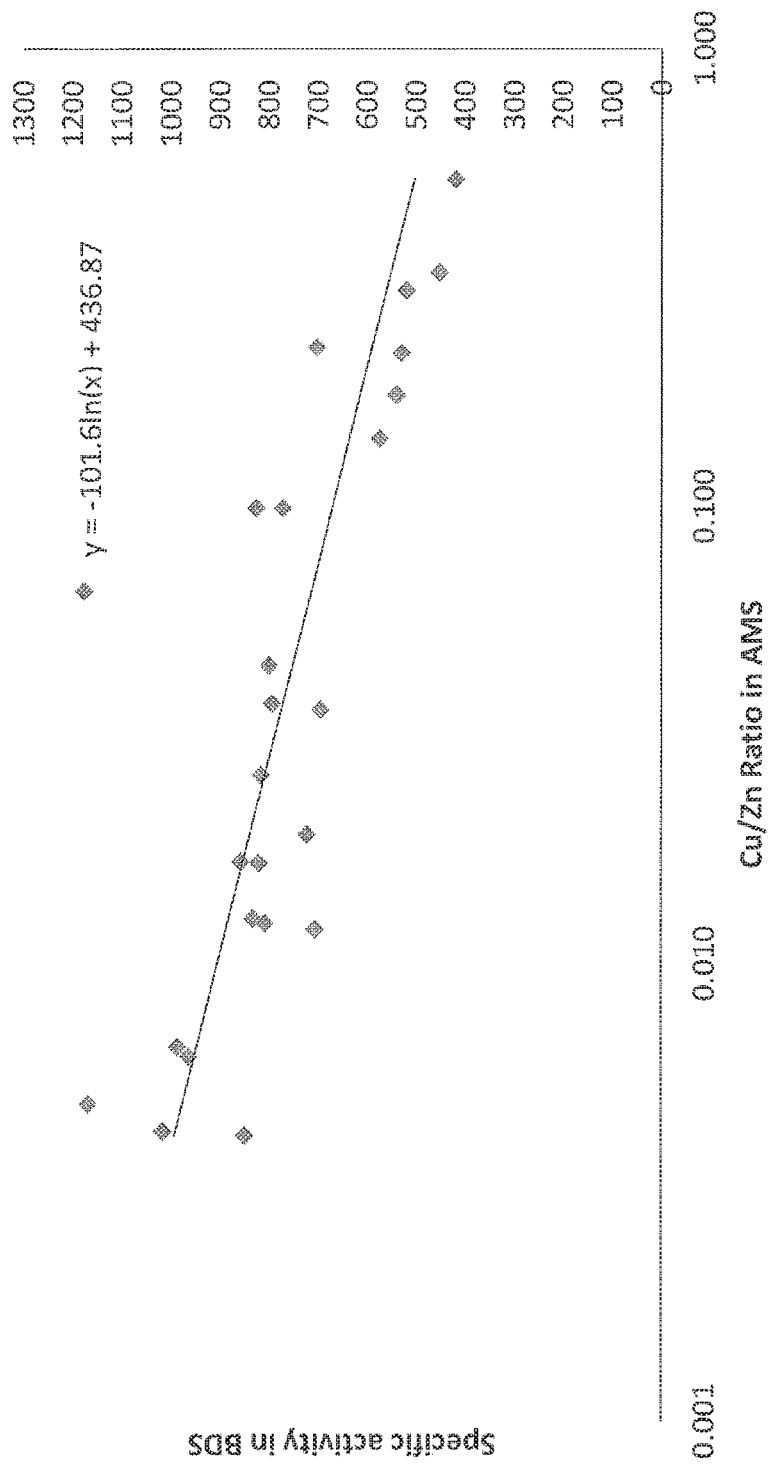
FIG. 10 is a graph showing the correlation between the Cu/Zn molar ratio in the AMS used in the HIC step and the specific activity in the final BDS. The specific activity was calculated to be equal to 436.87−101.6×ln (Cu/Zn molar ratio), while $R^2=0.58$.
Figure 11:
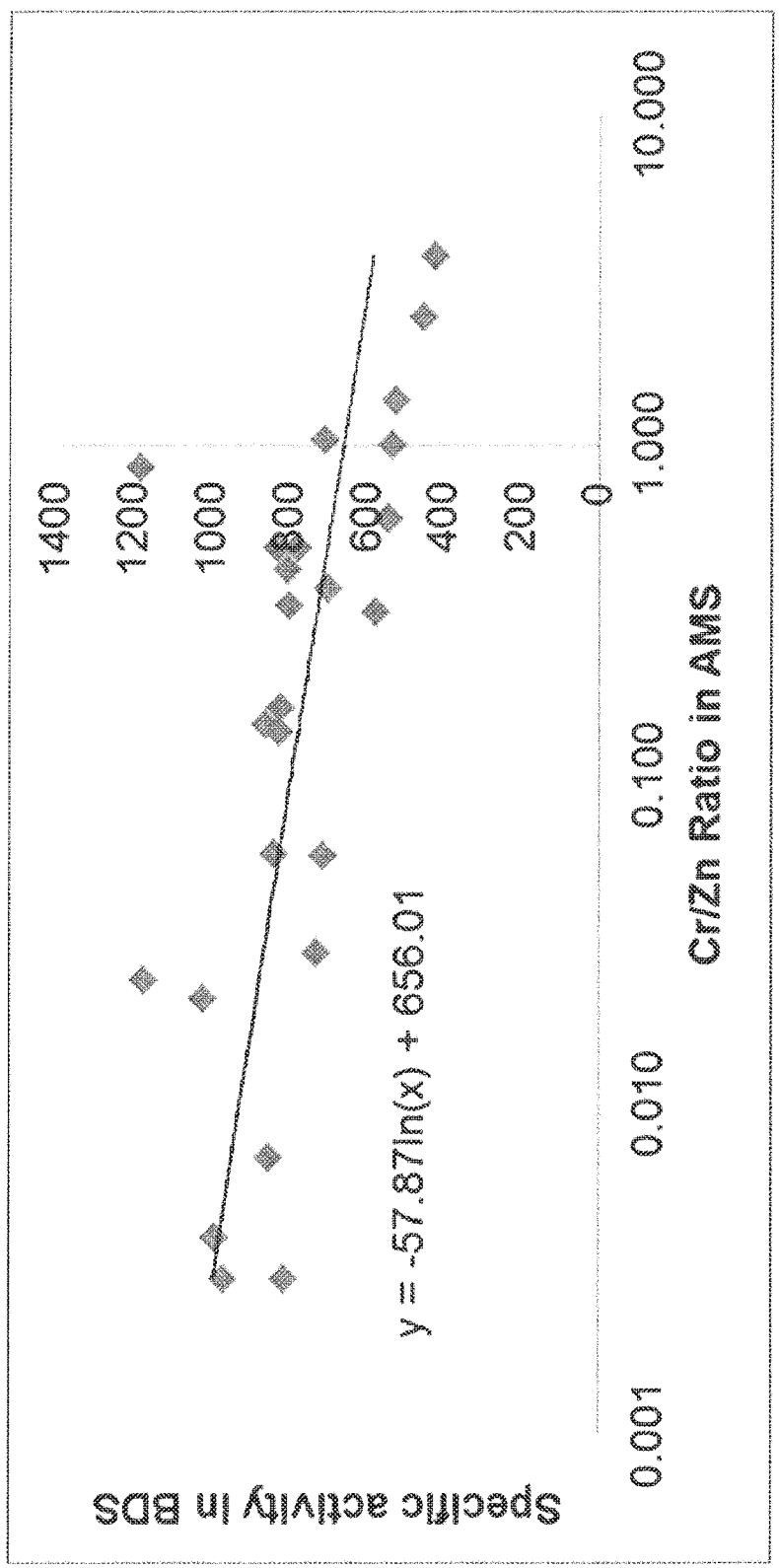
FIG. 11 is a graph showing the correlation between the Cr/Zn molar ratio in the AMS used in the HIC step and the specific activity in the final BDS. The specific activity was calculated to be equal to 656.01−57.87×ln (Cr/Zn molar ratio), while $R^2=0.36$.
Figure 12:
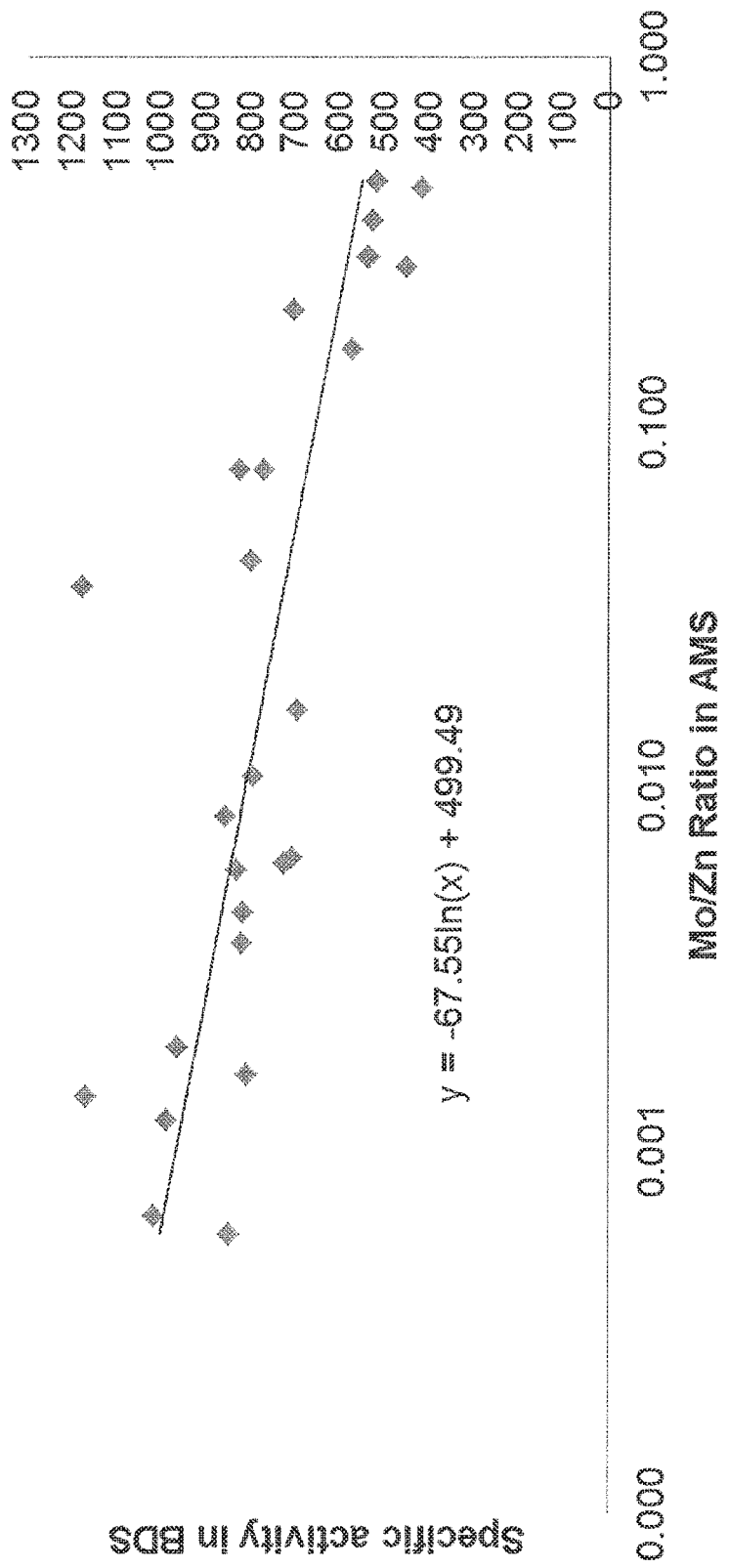
FIG. 12 is a graph showing the correlation between the Mo/Zn molar ratio in the AMS used in the HIC step and the specific activity in the final BDS. The specific activity was calculated to be equal to 499.49−67.55×ln (Mo/Zn molar ratio), while $R^2=0.56$.
Figure 13:
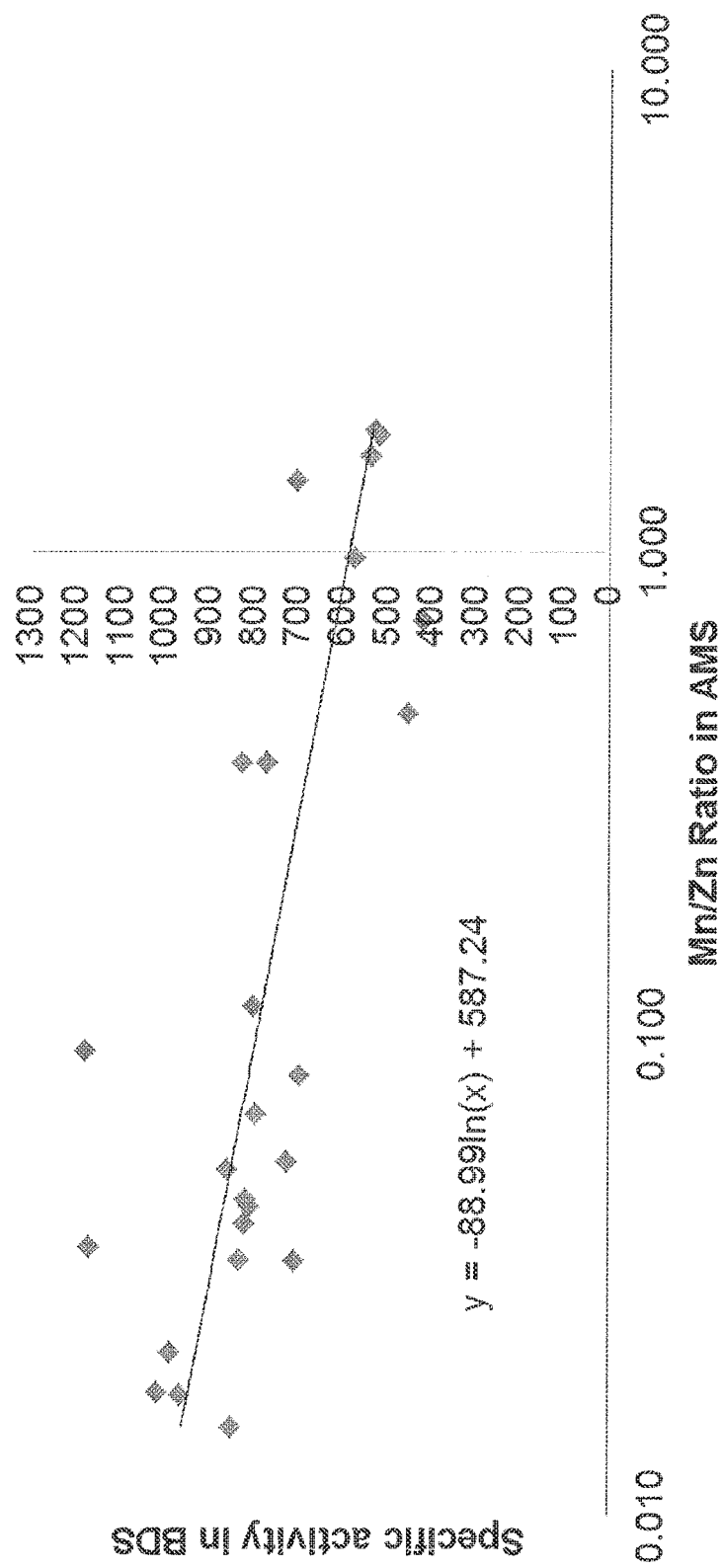
FIG. 13

Zinc is required to confer enzymatic activity for alkaline phosphatases (and thus asfotase alfa). Increased levels of other metals relative to zinc may impact specific activity. Thus, the metal/zinc ratios observed in the AMS were analyzed for the different metals which affected the BDS specific activity (as shown in Table 2 and FIGS. 8-15). In addition, $Ca^{2+}$ and $Mg^{2+}$ were also included in this analysis due to their role in enzyme activity for alkaline phosphatases (and thus asfotase alfa). The metal/zinc ratios were calculated from the metal levels observed in the load dilution buffer of the HIC step which was used in the production of each of the 26 BDS batches, as discussed above. The data demonstrated that calcium (Ca) and nickel (Ni) were two of the most abundant metals in the ammonium sulfate, while Cobalt (Co), copper (Cu) and molybdenum (Mo) were the least abundant metals. The analysis also showed that the molar ratios of Co/Zn (FIG. 8), Cu/Zn (FIG. 10), Mo/Zn (FIG. 12), Mn/Zn (FIG. 13), and Ni/Zn (FIG. 15) in the HIC load dilution buffer had a negative impact (i.e., an increase of the metal/zinc ratio in the AMS correlates with a decreased specific activity) on the specific activity of the BDS ($R^2 \geq 0.4$). The correlation was considered strong when $R^2 \geq 0.6$, weak when $0.6 > R^2 > 0.4$, and not clearly existing when $R^2 \leq 0.4$. An $R^2$ threshold value of >0.4 (model explains at least 40% of the variation observed) was selected as the cut-off for further consideration, so that metals with strong or weak correlation were both selected for testing in small scale studies. The correlations for Ca/Zn (FIG. 8) and Mg/Zn (FIG. 14) molar ratios were lower than the $R^2$ cut-off threshold in this analysis.

TABLE 2

Metal/zinc molar ratios measured in the HIC load dilution buffer

| Parameter | Mean | Std Dev | Min | Max | Range | CV | Median |
|---|---|---|---|---|---|---|---|
| Ca/Zn | 3.039 | 2.250 | 0.115 | 8.234 | 8.119 | 74.023 | 3.314 |
| Co/Zn | 0.058 | 0.066 | 0.001 | 0.194 | 0.193 | 113.543 | 0.025 |
| Cu/Zn | 0.100 | 0.128 | 0.004 | 0.519 | 0.515 | 128.583 | 0.037 |

TABLE 2-continued

Metal/zinc molar ratios measured in the HIC load dilution buffer

| Parameter | Mean | Std Dev | Min | Max | Range | CV | Median |
|---|---|---|---|---|---|---|---|
| Cr/Zn | 0.569 | 0.858 | 0.003 | 3.775 | 3.772 | 150.827 | 0.322 |
| Mo/Zn | 0.106 | 0.149 | 0.000 | 0.459 | 0.459 | 141.154 | 0.014 |
| Mn/Zn | 0.454 | 0.633 | 0.012 | 1.801 | 1.789 | 139.337 | 0.075 |
| Mg/Zn | 0.787 | 0.732 | 0.005 | 2.037 | 2.032 | 92.967 | 0.623 |
| Ni/Zn | 1.973 | 3.998 | 0.010 | 17.688 | 17.678 | 202.667 | 0.160 |

A summary of the impact of metal concentration (as effected by changes in the Metal/Zinc molar ratios in, for example, the load dilution buffer, the equilibration buffer, and the wash 1 buffer) on asfotase alfa specific activity in the HIC pool is shown in Table 3 and FIG. 17. Specifically, HIC solutions were spiked with the metal ratios shown in Table 3 and used to process material across the HIC in a 96-well plate format. The resulting HIC pools were then analyzed for specific asfotase alfa activity. In conclusion, Copper (Cu) and Nickel (Ni) have a significant impact on asfotase alfa specific activity at metal/zinc molar ratios above 1:1. Cobalt (Co) also has an impact on asfotase alfa specific activity at metal/zinc molar ratios above 5:1. Calcium (Ca) only has a weak impact on asfotase alfa specific activity at the metal/zinc molar ratio of about 25:1.

TABLE 3

Specific Activity (U/mg) in the HIC pool for runs at Different Metal/Zinc Ratios

| Molar Ratio | Chromium | Manganese | Iron | Nickel | Copper | Magnesium | Calcium | Cobalt | Molybdenum |
|---|---|---|---|---|---|---|---|---|---|
| 0 | 792 | 792 | 792 | 792 | 792 | 792 | 792 | 811 | 808 |
| 0.5:1 | 813 | 760 | 778 | 865 | 722 | 891 | 740 | 724 | 959 |
| 1:1 | 802 | 767 | 923 | 784 | 684 | 894 | 756 | 785 | 737 |
| 5:1 | 872 | 749 | 944 | 579 | 511 | 933 | 792 | 691 | 845 |
| 25:1 | 767 | 842 | 801 | 353 | 198 | 837 | 658 | 652 | 949 |

Based on these analyses, the ratio of impactful metals (Co, Cu, Mo, Mn and Ni) to Zn in the AMS at different BDS specific activity values can be calculated (e.g., using the equations in FIGS. 9, 10, 12, 13, and 15). These ratios were determined from a specific activity values of 620 U/mg (the lower limit of the set specification for BDS specific activity) and of 680 U/mg (to provide a safety factor for produced asfotase alfa BDS). These values are listed in Table 4. Each buffer and/or solution used in each of the downstream purification and concentration steps for the produced asfotase alfa should have the metal/Zinc ratios exemplified in Table 4, so that the specific activity of the final asfotase alfa BDS will reach to about 620 U/mg to about 680 U/mg.

TABLE 4

Minimum metal ratios required for BDS specific activity of 620 U/mg and 680 U/mg

| | Metal/Zinc Ratio (620 U/mg) | Metal/Zinc Ratio (680 U/mg) |
|---|---|---|
| Co/Zn | 0.09 | 0.05 |
| Cu/Zn | 0.16 | 0.09 |
| Mo/Zn | 0.16 | 0.07 |
| Mn/Zn | 0.68 | 0.35 |
| Ni/Zn | 1.90 | 0.85 |

Metal ions have to be also controlled to avoid any potential elemental impurities impacting patient safety. Thus maximum levels of these metals in the AMS may be determined based upon the correlation between the concentration of the metals in AMS and the resulting concentration of the metals in the BDS, also taking into account the parenteral permitted daily exposures (PDE), which are, e.g., 20 µg/day for nickel, 5 µg/day for cobalt and 300 µg/day for copper. The PDE calculations are based on an arbitrary adult human body mass for either sex of 50 kg in weight. The recommended dosage regimen of asfotase alfa is 2 mg/kg of body weight administered subcutaneously three times per week, or a dosage regimen of 1 mg/kg of body weight administered six times per week.

The PDE calculations are performed using a maximum daily dose of 100 mg/day. The maximum dose of 100 mg is based upon a 50 kg adult receiving the maximum allowable dose of 2 mg/kg. All patient dosings of asfotase alfa are dependent on their body mass. Calculation of a maximum daily dose based on 50 kg body mass allows for direct comparison to the PDE which is also based on a 50 kg body mass. Thus, the concentration of Nickel, Cobalt and Copper in AMS and BDS in various BDS lots were calculated. The relationship between the concentration of nickel, cobalt and copper in the AMS and the resulting metal content in BDS per 100 mg dose were also calculated and the data fit to a linear regression. For [Ni] in AMS load dilution buffer (µg/L in a 2 M solution, the X axis) vs. [Ni] in 100 mg dose (µg, the Y axis), the equation is $y=0.03x+0.09$, while $R^2=0.9$. For [Co] in AMS load dilution buffer (µg/L in a 2 M solution, the X axis) vs. [Co] in 100 mg dose (µg, the Y axis), the equation is $y=0.06x+0.15$, while $R^2=0.80$. For [Cu] in AMS load dilution buffer (µg/L in a 2 M solution, the X axis) vs. [Cu] in 100 mg dose (µg, the Y axis), the equation is $y=0.05x+0.22$, while $R^2=0.8$. Using these equations, a maximum limit of nickel, cobalt and copper contents in the AMS can be determined so as not to exceed the PDE values in the BDS (e.g., 20 µg/day for nickel, 5 µg/day for cobalt and 300 µg/day for copper). These limits are listed in Table 5, in both µg/L in a 2 M solution and in ppm, along with a ppm value taking into account a 20% safety factor and at 30% of the PDE. The ppm value is calculated by dividing the µg/L value by the grams of AMS required to make a 2 M solution (i.e., 264.3 g).

TABLE 5

Levels of nickel, cobalt and copper in AMS relative to PDE

| | Nickel | Cobalt | Copper |
|---|---|---|---|
| PDE (µg/day) | 20 | 5 | 300 |
| Maximum metal in AMS not to exceed PDE (µg/L in 2M solution of AMS) | 617 | 79 | 6559 |

TABLE 5-continued

Levels of nickel, cobalt and copper in AMS relative to PDE

| | Nickel | Cobalt | Copper |
|---|---|---|---|
| Maximum metal in AMS not to exceed PDE in ppm | 2.33 | 0.30 | 24.82 |
| Maximum metal in AMS not to exceed 30% of PDE in ppm | 0.7 | 0.09 | 7.45 |
| Maximum metal in AMS not to exceed PDE in ppm with 20% safety factor | 1.87 | 0.24 | 19.86 |

Based on the above analyses (e.g., Tables 4 and 5), the preferred limits for AMS, and for other buffers, may include, e.g., less than about 0.09 for the Co/Zn molar ratio (ppm/ppm), less than about 0.16 for Cu/Zn molar ratio (ppm/ppm), less than about 1.90 for Ni/Zn molar ratio (ppm/ppm), less than about 1.87 ppm for [Ni], less than about 0.24 ppm for [Co], and less than about 19.86 ppm for [Cu]. With similar analyses, less than about 9.13 ppm for [Mn] is also preferred for the AMS used in the HIC step. In practice, prior to reaching the above discussed limits, possible efforts may be needed to ensure sufficient specific activity of BDS. Such limits for action may include, e.g., more than about 0.05 for the Co/Zn molar ratio (ppm/ppm), more than about 0.09 for Cu/Zn molar ratio (ppm/ppm), more than about 0.85 for Ni/Zn molar ratio (ppm/ppm), more than about 0.7 ppm for [Ni], more than about 0.09 ppm for [Co], more than about 7.45 ppm for [Cu] and less than 0.21 ppm for [Zn]. Since alkaline phosphatases, and thus asfotase alfa, require Zn to be coordinated in the active site to maintain enzymatic activity, the zinc content in the AMS may be also important to ensure the specific activity of the final BDS. In addition, it was found in some tested batches of asfotase alfa HIC pool or BDS that some lots of AMS or other buffer components contained very low concentration of zinc ions. Thus, extra effort is required (which may be difficult and/or expensive) to remove or to lower the content of metal ions, which negatively impact the specific activity of asfotase alfa (such as disclosed herein), so that the metal/Zn molar ratio (e.g., below the recommended thresholds as discussed above) can be lowered to improve specific activity in the HIC pool or BDS. An alternative solution is to add extra zinc ions into the buffers during the downstream processes (such as the HIC process). A 96-well plate screening study was performed to evaluate the impact of spiking different levels of zinc in the AMS on the specific activity and zinc metal content of the HIC pools.

Table 6 shows the specific activity and the zinc molar ratio results for the diluted HIC pool and buffer-exchanged diluted HIC pools generated from 96-well plate studies spiked with different levels of zinc sulfate heptahydrate in the HIC load dilution buffer.

TABLE 6

Summary of product quality results from the 96-well plate Zinc sulfate Spiking Studies

| | | | | | | Buffer-Exchanged Samples | |
|---|---|---|---|---|---|---|---|
| | | Ratio (µg Zinc Sulfate | Net Samples | | | | Zinc Molar Ratio (Moles of |
| Run # | Pool | Heptahydrate/g AMS) | Activity (U/mg) | Average (U/mg) | Standard Deviation | Activity (U/mg) | Zn/Moles of asfotase alfa) |
| 1 | 1 | 0 | 747 | 699 | | 824 | 1.93 |
| | 2 | | 651 | | 68 | | |
| 2 | 1 | 5 | 629 | | | 881 | 1.85 |
| | 2 | | 741 | 685 | 79 | | |

TABLE 6-continued

Summary of product quality results from the 96-well plate Zinc sulfate Spiking Studies

| Run # | Pool | Ratio (μg Zinc Sulfate Heptahydrate/g AMS) | Net Samples Activity (U/mg) | Net Samples Average (U/mg) | Net Samples Standard Deviation | Buffer-Exchanged Samples Activity (U/mg) | Buffer-Exchanged Samples Zinc Molar Ratio (Moles of Zn/Moles of asfotase alfa) |
|---|---|---|---|---|---|---|---|
| 3 | 1 | 10 | 759 | | | 922 | 2.09 |
|  | 2 |  | 735 | 747 | 17 | | |
| 4 | 1 | 15 | 697 | | | 922 | 2.09 |
|  | 2 |  | 722 | 710 | 18 | | |
|  | 1 |  | 685 | | | 886 | 1.97 |
| 5 | 2 | 20 | 649 | 667 | 25 | | |
| 6 | 1 | 0 | 711 | | | 842 | 1.38 |
|  | 2 |  | 759 | 735 | 34 | | |
| 7 | 1 | 50 | 725 | | | 962 | 2.28 |
|  | 2 |  | 790 | 758 | 46 | | |
| 8 | 1 | 100 | 724 | | | 925 | 2.05 |
|  | 2 |  | 753 | 739 | 21 | | |
| 9 | 1 | 300 | 761 | | | 919 | 2.1 |
|  | 2 |  | 771 | 766 | 7 | | |
| 10 | 1 | 600 | 774 | | | 1029 | 2.22 |
|  | 2 |  | 753 | 764 | 15 | | |
| 11 | 1 | Positive Control | 748 | | | 870 | 1.93 |
|  | 2 |  | 685 | 717 | 45 | | |
| 12 | 1 | Negative Control | 466 | | | 533 | 1.02 |
|  | 2 |  | 459 | 463 | 5 | | |
| Load |  | Protein A pool | 467 | | | 491 | 1.26 |

Table 6 and FIG. 18 show the results of the specific activity of the HIC pools from the 96-well plate study (diluted HIC pool and buffer-exchanged diluted HIC pools). The data show that the specific activity in the HIC pool increased with increasing zinc sulfate heptahydrate concentration in the AMS of the HIC load dilution buffer and it was stable at zinc sulfate heptahydrate concentrations >100 ppm (i.e., 1 μg zinc sulfate heptahydrate per gram of AMS, as in FIG. 18).

Table 6 and FIG. 19 show the zinc molar ratio in the buffer-exchanged HIC pools versus the zinc sulfate heptahydrate in AMS. The data show that the zinc molar ratio increased with increasing zinc sulfate heptahydrate concentration in AMS used in the HIC load dilution buffer and it was stable at zinc sulfate heptahydrate concentrations >100 ppm.

Historically, levels from 0.2-5.9 ppm Zn (equivalent to 0.9-26 ppm of zinc sulfate heptahydrate or 0.9-26 μg of zinc sulfate heptahydrate per gram of AMS) were found in the load and dilution buffers containing ammonium sulfate. Additionally, the maximum level of copper in the AMS was set to be 19.86 ppm with a copper to zinc molar ratio of 0.16 (as discussed above). Therefore, the minimum amount of zinc sulfate heptahydrate which needed to be present in the AMS at the highest levels of copper (19.86 ppm) was 124.1 ppm. Based on this information, and on the data presented in Table 6 and FIGS. 18 and 19, the minimum level of zinc sulfate heptahydrate needed in the HIC load dilution, equilibration, wash 1, and wash 2 solutions was determined to be 550 ppm of Zinc Sulfate heptahydrate (μg of zinc sulfate heptahydrate/gram of AMS).

The correlation between zinc molar ratio and specific activity is shown in FIG. 20. Zinc molar ratio refers to mole of zinc/mole of asfotase alfa monomer as determined, e.g., by an ICP-MS method.

A further study using 1-cm diameter column was performed to assess the impact of supplementing zinc sulfate heptahydrate in HIC process solutions (e.g., HIC load dilution, HIC equilibration, wash 1, and wash 2 solutions) on the product quality of the HIC pool. Based on results from the above 96-well plate study, the minimum level of zinc sulfate heptahydrate to be supplemented in the HIC load dilution, equilibration/wash 1 and wash 2 buffers of the HIC process step was chosen to be 550 ppm of zinc sulfate heptahydrate (μg of zinc sulfate heptahydrate/gram of AMS). In the 1-cm diameter column study, the impact of three levels of zinc sulfate heptahydrate (550 ppm, 600 ppm and 680 ppm) in the HIC process buffers on the HIC pool product quality was assessed using three different ammonium sulfate (AMS) lots from Avantor Performance Materials (Center Valley, Pa.). A control run with no supplementation of zinc sulfate heptahydrate in the HIC process buffers for each AMS lot was also performed. Protein A pool was used as the load material for the 1-cm column runs. The diluted HIC pool and the buffer-exchanged diluted HIC pools were assessed for specific activity (pNPP). The diluted HIC pool product quality was also assessed by inorganic pyrophosphate (PPi) hydrolysis, anion exchange (AEX), total sialic acid content (TSAC), and size exclusion HPLC (SEC-HPLC) assays. The buffer-exchanged diluted HIC pool was also assessed by Inductively Coupled Plasma Mass Spectrometry (ICP-MS) assay to determine the zinc, magnesium and calcium molar ratio.

AMS lots with zinc concentrations lower than 0.1 μg/g and with resulting Co/Zn, Ni/Zn, and Cu/Zn molar ratios higher than the values in Table 6, produced asfotase alfa of low specific activity. However, with zinc sulfate supplementation at 550, 600, or 680 ppm, the same lot of AMS produced asfotase alfa BDS that passed specific activity specifications.

Table 7 and FIGS. 21-24 present the product quality results for the diluted HIC pools and buffer-exchanged diluted HIC pools generated from the 1-cm column runs supplemented with 550 ppm, 600 ppm and 680 ppm of zinc sulfate heptahydrate in the HIC process buffers (HIC load dilution, HIC equilibration/wash 1 and HIC wash 2 buffers) using three different AMS lots. The product quality results of the HIC pools from the control runs performed with no zinc sulfate heptahydrate supplementation are also shown in Table 7.

TABLE 7

Asfotase alfa product quality data

| AMS Lot # | Zinc Sulfate Concentration (ppm) | Diluted HIC Pool Specific Activity (U/mg) | Diluted HIC pool Specific Activity (U/mg) (Buffer Exchanged) | % Main Band (wAEX) | % Acidic species (wAEX) | % Basic species (wAEX) | $K_m$ (μM) | $K_{cat}$ (s$^{-1}$) | SEC (% Aggregate) | SEC (% Dimer) | Zinc Molar ratio (mole of Zinc/ mole of asfotase alfa monomer) | Magnesium Molar ratio (mole of Magnesium/ mole of asfotase alfa monomer) | Calcium Molar ratio (mole of Calcium/ mole of asfotase alfa monomer) |
|---|---|---|---|---|---|---|---|---|---|---|---|---|---|
| 1 | 0 | 701 | 719 | 99.0 | 0.8 | 0.2 | 23.8 | 95.8 | 0.0 | 100 | 1.64 | 0.21 | 1.09 |
|  | 550 | 809 | 856 | 98.9 | 0.9 | 0.2 | 32.5 | 121.2 | 0.5 | 99.5 | 2.54 | 0.14 | 1.42 |
|  | 600 | 850 | 883 | 98.8 | 0.8 | 0.4 | 38.7 | 154.9 | 0.0 | 100 | 2.55 | 0.13 | 1.15 |
|  | 680 | 841 | 835 | 98.9 | 0.6 | 0.5 | 26.0 | 109.9 | 0.5 | 99.5 | 3.15 | 0.14 | 1.27 |
| 2 | 0 | 737 | 704 | 98.9 | 0.7 | 0.4 | 15.7 | 99.4 | 0.4 | 99.6 | 1.99 | 0.20 | 1.21 |
|  | 550 | 859 | 847 | 99.1 | 0.7 | 0.4 | 26.7 | 88 | 0.5 | 99.5 | 2.85 | 0.13 | 1.11 |
|  | 600 | 843 | 863 | 99.0 | 0.7 | 0.3 | 48.7 | 104 | 0.4 | 99.6 | 2.84 | 0.12 | 1.05 |
|  | 680 | 852 | 852 | 99.1 | 0.7 | 0.3 | 41.9 | 99.4 | 0.4 | 99.6 | 2.74 | 0.12 | 1.06 |
| 3 | 0 | 684 | 690 | 99.0 | 0.7 | 0.3 | 22.1 | 94.7 | 0.0 | 100 | 1.76 | 0.27 | 1.14 |
|  | 550 | 833 | 861 | 99.0 | 0.8 | 0.2 | 27.3 | 121.3 | 0.0 | 100 | 2.74 | 0.14 | 1.06 |
|  | 600 | 1122 | 877 | 99.0 | 0.7 | 0.2 | 37.1 | 115.7 | 0.5 | 99.5 | 2.62 | 0.13 | 1.08 |
|  | 680 | 857 | 847 | 99.0 | 0.8 | 0.2 | 25 | 119.2 | 0.4 | 99.6 | 2.83 | 0.14 | 1.00 |
| Protein A pool | N/A | 449 | 400 | 91.5 | 8.4 | 0.2 | 31.5 | 129.2 | 0.0 | 100 | 1.23 | 0.25 | 0.99 |

FIG. 21 shows that the specific activity in the HIC pool increases with zinc sulfate heptahydrate supplementation in the HIC process buffers at 550 ppm, 600 ppm and 680 ppm in comparison to control runs without zinc sulfate heptahydrate supplementation. Two of the three AMS lots were tested without zinc sulfate heptahydrate supplementation (Lot 1 and 3) and failed to meet the specific activity acceptance criteria of 710-1250 U/mg. However, when screened previously, these two lots passed the acceptance criteria. This discrepancy demonstrates inherent variability in the HIC process without zinc supplementation, and provides further evidence that zinc supplementation provides a more robust HIC chromatography step. The specific activity of the runs with zinc sulfate heptahydrate supplementation were within the BDS release specifications (620-1250 U/mg).

Corresponding to the specific activity increase, an increase in the $K_{cat}$ and $K_m$ values in the PPi assay and the zinc molar ratio in the HIC pools were observed with zinc sulfate heptahydrate supplementation (FIGS. 22-24). The $K_m$ (FIG. 23) and $K_{cat}$ (FIG. 22) values of the zinc sulfate supplemented runs met the BDS release specifications ($K_m$: 13-69 μm and $K_{cat}$: 65-165 s$^{-1}$). With the zinc sulfate heptahydrate supplementation, the zinc molar ratios increased (FIG. 24), while the calcium/zinc molar ratios were found previously to remain unchanged and the magnesium/zinc molar ratios decreased slightly. These trends were as expected and the zinc and calcium molar ratio met the acceptance limits set for the BDS. Interestingly, zinc supplementation (550, 600, or 680 ppm) did not change the % monomer (by SEC-HPLC), % Main Peak, % Acidic Peak (both by AEX) or the product TSAC values in the diluted HIC pools. For example, the TSAC contents of the produced asfotase alfa in the diluted HIC pools with or without zinc supplementation (550, 600, or 680 ppm) for three AMS lots (Lot 1, Lot 2, and Lot 3 as in Table 7) were approximately 1.5. The % dimer and % aggregate by the SEC-HPLC assay met the BDS release specifications (≥97.6% dimer, ≤2.4% aggregates). The main, acidic and basic peaks by AEX assay also met the BDS specifications (≥93.7% main, ≤4.9% acidic, and ≤3.4% basic). The above data indicate that the product quality of the HIC pools generated with the zinc sulfate heptahydrate supplementation in the HIC process buffers (550 ppm-680 ppm) met the BDS release specifications and was comparable or better than the control runs without zinc supplementation.

The data indicate that the activity of the HIC pool by pNPP and PPi assays and zinc molar ratio increases with zinc sulfate heptahydrate supplementation in the HIC process buffers in comparison to control runs without zinc supplementation. A summary of exemplary zinc concentrations (set points, target range and acceptable range) in HIC process buffers is given in Table 8. Zinc from other sources may be supplemented similarly (e.g., in 550 ppm, 600 ppm, or 680 ppm) to HIC process buffers to reach these exemplary concentrations. In the exemplary zinc sulfate heptahydrate addition, the target concentration of 600 ppm of zinc sulfate heptahydrate in the HIC process buffers is equivalent to 550 μM of zinc sulfate heptahydrate in the HIC load dilution buffer, 300 μM in the equilibration buffer, and 260 μM in the post-load wash 2 buffer.

TABLE 8

Exemplary set-point, target and acceptable ranges for zinc sulfate heptahydrate in HIC process buffers

|  | Units | HIC Load/<br>Dilution Buffer | | HIC<br>Equilibration/<br>Post Load<br>Wash 1 Buffer | | HIC Post Load<br>Wash 2 Buffer | |
|---|---|---|---|---|---|---|---|
| Set Point | µg ZnSO$_4$·7H$_2$O/g of AMS | 600 | | 600 | | 600 | |
|  | mM zinc sulfate heptahydrate | 0.55 | | 0.30 | | 0.26 | |
|  | g ZnSO$_4$·7H$_2$O/L of buffer | 0.159 | | 0.087 | | 0.075 | |
| Target Range (Batch Record Range-SP ±0.5%) | µg ZnSO$_4$·7H$_2$O/g of AMS | 597 | 603 | 597 | 603 | 597 | 603 |
|  | g ZnSO$_4$·7H$_2$O/L of buffer | 0.1578 | 0.1594 | 0.0868 | 0.0876 | 0.0749 | 0.0757 |
| Acceptable Range | µg ZnSO$_4$·7H$_2$O/g of AMS | 550 | 650 | 550 | 650 | 550 | 650 |
|  | mM ZnSO$_4$ | 0.505 | 0.597 | 0.278 | 0.329 | 0.240 | 0.284 |
|  | g ZnSO$_4$·7H$_2$O/ L of buffer | 0.145 | 0.172 | 0.080 | 0.094 | 0.069 | 0.082 |

Further studies were carried out to analyze the effect of zinc and other metal ions disclosed herein on specific activity when buffers in the downstream processes contain sodium sulfate instead of ammonium sulfate (AMS). Surprisingly, zinc supplementation (in the form of zinc sulfate) did not significantly improve specific activity or the zinc molar ratio. In addition, zinc supplementation did not affect the molar ratios for Ni, Mg, Ca, Al, Fe, Cr, Cu, or Mn. Without being limited to this theory, it is hypothesized that AMS may facilitate the removal of zinc ion from the active site of alkaline phosphatase (such as asfotase alfa).

Example 3

Impact of Hydrophobic Interaction Chromatography (HIC) Buffer Conditions on the Metal Content and Specific Activity of Asfotase Alfa We performed experiments to determine whether ammonium sulfate (AMS) promotes the removal of zinc ion from the active site of alkaline phosphatase, such as asfotase alfa. Buffer conditions included AMS and sodium sulfate buffer, while resin conditions included Butyl SEPHAROSE® HP and CAPTO® Butyl agarose resin. AMS and sodium sulfate can be used to drive the hydrophobic interaction between an alkaline phosphatase and the HIC resin and sodium sulfate contains a less chaotropic cation than AMS. The CAPTO® Butyl agarose resin is an equivalent hydrophobic ligand to the Butyl SEPHAROSE® HP resin, but features a more highly crosslinked resin matrix.

As described in Examples 1 and 2, the HIC process was initially performed using either a Butyl SEPHAROSE® HP resin (Condition A) in combination with AMS buffer or a CAPTO® Butyl agarose resin in combination with sodium sulfate buffer (Condition D). The HIC process was separately tested using the Butyl SEPHAROSE® HP resin in combination with the sodium sulfate buffer (Condition B) and using the CAPTO® Butyl agarose resin in combination with the AMS buffer (Condition C).

The downstream purification of asfotase alfa was performed using Condition B and Condition D. In particular, asfotase alfa was purified using MabSelect SuRe Protein A affinity chromatography after the solvent/detergent viral inactivation step described in Example 1. The MAbSelect pool was then adjusted for conductivity with a load dilution buffer of either 40 mM 4-(2-hydroxyethyl)-1-piperazineethanesulfonic acid (HEPES), 2.0 M AMS, pH 7.5, or 40 mM Sodium Phosphate, 1.1 M Sodium Sulfate, pH 7.50. HIC was performed on the MabSelect pool adjusted with the sodium sulfate buffer using the Butyl SEPHAROSE® HP resin and on the MabSelect pool adjusted with the AMS buffer using the CAPTO® Butyl agarose resin. The HIC products prepared using these different conditions were then buffer-exchanged to remove the AMS or sodium sulfate buffer and tested for specific activity and metal content. The AMS and sodium sulfate buffers used for HIC purification of asfotase alfa are shown in Tables 9 and 10, respectively.

TABLE 9

Ammonium sulfate (AMS) buffers used for HIC

| Buffer Use | Buffer components |
|---|---|
| Load Dilution Buffer | 40 mM HEPES, 2.0M Ammonium Sulfate, pH 7.50 |
| Equilibration/Post Load Wash 1 Buffer | 20 mM HEPES, 1.1M Ammonium Sulfate, pH 7.50 |
| Post Load Wash 2 Buffer | 20 mM HEPES, 0.95M Ammonium Sulfate, pH 7.50 |
| Elution Buffer | 25 mM Sodium Phosphate, 0.5M Ammonium Sulfate, pH 7.40 |
| Elution Dilution Buffer | 50 mM Sodium Phosphate, 100 mM Sodium Chloride, pH 7.50 |

TABLE 10

Sodium sulfate buffers used for HIC

| Buffer Use | Buffer components |
|---|---|
| Load Dilution Buffer | 40 mM Sodium Phosphate, 1.1M Sodium Sulfate pH 7.50 |
| Equilibration/ Post Load Wash Buffer | 35 mM Sodium Phosphate, 880 mM Sodium Sulfate pH 7.50 Buffer |
| Elution Buffer/ Elution Dilution Buffer | 20 mM Sodium Phosphate, 445 mM Sodium Sulfate pH 7.50 |

Metal spiking experiments with exemplary metals (Ni, Co, and Cu) up to 2 mg/L were conducted using pre-filled 96-well filter plates (i.e., PREDICTOR® plates) for each buffer and resin combination to assess the role of HIC processing conditions in exchange of active-site metal ions of asfotase alfa. Our results show that with increased metal spiking there was decreased specific activity of asfotase alfa in the HIC purified pool (Ni shown, FIG. 25A) and decreased active-site metal (zinc) content of asfotase alfa (FIG. 25A) under Condition A and Condition C relative to Condition B and Condition D. Thus, under conditions of high metal content in buffers, loss of alkaline phosphatase activity and a decrease in active-site metal ions (zinc) resulted from the use of AMS in the HIC process to drive the hydrophic interaction between the HIC column and asfotase alfa.

Our results show that the AMS buffer promoted metal exchange during HIC purification of asfotase alfa in combination with either the Butyl SEPHAROSE® HP resin or the CAPTO® Butyl agarose resin. Notably, the sodium sulfate buffer promoted little to no metal exchange during HIC purification of asfotase alfa in combination with the Butyl SEPHAROSE® HP resin and the CAPTO® Butyl agarose resin. The resin (Butyl SEPHAROSE® HP or CAPTO® Butyl agarose resin) used for HIC did not affect the metal content of purified asfotase alfa. These studies confirm that the loss of enzyme activity in the metalloenzyme asfotase alfa resulted from substitution of active-site metal ions with competing metal ions originating in the AMS buffer and that HIC process conditions may promote active-site access and metal ion exchange.

Methods used in Examples include:

Specific Activity Testing

The diluted HIC pool was tested for specific activity using an exemplary pNPP-based alkaline phosphatase enzymatic assay. Specifically, this method is used for the determination of asfotase alfa enzymatic activity using pNPP as a substrate. Asfotase alfa is a recombinant protein that has one domain from the human tissue non-specific alkaline phosphatase enzyme. This domain is catalytically active and hydrolyzes phosphate esters. The assay is performed at enzyme saturation to reach and maintain $V_{max}$ for duration of the measurement. The pNPP is hydrolyzed into a yellow colored product (maximal absorbance at 405 nm). The rate of reaction is directly proportional to the enzyme activity. One unit (U) corresponds to 1 μmol of pNPP formed per minute under the employed method conditions. The Specific Activity by pNPP (enzymatic activity per mg protein) was calculated from the enzymatic activity and the Protein Concentration by $A_{280}$.

Zinc Content Testing

Approximately 5 mL of each of the HIC diluted pool generated from the 1-cm column runs (run 1 and run 2) was buffer-exchanged into about 5 diavolumes of 25 mM sodium phosphate, 150 mM sodium chloride, pH 7.4 buffer using 30 kDa cut-off centrifuge filters.

Calculations

Average Specific Activity:

Average specific activity (U/mg)=(Specific activity from Run 1+Specific activity from Run 2)/2

Average Zinc Molar Ratio in HIC Pool:

Average Zinc Molar Ratio in HIC Pool (mol/mol)= (Zinc molar ratio in Run 1+Zinc molar ration in Run 2)/2

Zinc Molar Ratio in the HIC Pool:

$$\text{Zinc Molar Ratio (mol/mol)} = \left(\frac{\text{Moles of } \frac{\text{Zinc}}{L}\left(\frac{\text{mol}}{1}\right)}{\text{moles of asfotase alfa}\frac{\text{monomer}}{L}(\text{mol}/L)}\right) = \left(\left(\text{grams of } \frac{\text{zinc}}{L}\right)\Big/ 65.39\right) \Big/ \left(\left(\text{grams of asfotase } \frac{\text{alfa}}{L}\right)\Big/ 80572\right)$$

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method of improving enzymatic activity of a recombinant alkaline phosphatase during production comprising:
   (i) culturing a recombinant cell culture that expresses an alkaline phosphatase;
   (ii) obtaining a preparation comprising recombinant alkaline phosphatase from the cell culture; and
   (iii) (a) decreasing in the preparation at least one of:
      (1) a concentration of Nickel (Ni) to less than about 2.33 ppm;
      (2) a concentration of Cobalt (Co) to less than about 0.30 ppm;
      (3) a concentration of Copper (Cu) to less than about 24.82 ppm;
      (4) a concentration of Manganese (Mn) to less than about 9.13 ppm;
      (5) a molar ratio of Nickel/Zinc to less than about 1.90;
      (6) a molar ratio of Cobalt/Zinc to less than about 0.09; and
      (7) a molar ratio of Copper/Zinc to less than about 0.16; and
   (b) increasing in the preparation a concentration of Zinc to at least about 550 ppm,
   wherein the method improves the enzymatic activity of the recombinant alkaline phosphatase.

2. The method of claim 1, further comprising:
   (iv) separating the recombinant alkaline phosphatase from the remainder of the preparation by Hydrophobic Interaction Chromatography (HIC).

3. The method of claim 2, wherein the separating comprises at least one of harvest clarification, ultrafiltration, diafiltration, viral inactivation, affinity capture, and combinations thereof.

4. The method of claim 2, further comprising measuring recombinant alkaline phosphatase activity, wherein the recombinant alkaline phosphatase activity increases after the separating step compared to the activity in the preparation prior to step (iii).

5. The method of claim 4, comprising measuring the activity by at least one method selected from the group consisting of: a pNPP-based alkaline phosphatase enzymatic assay and an inorganic pyrophosphate (PPi) hydrolysis assay.

6. The method of claim 5, wherein at least one of the recombinant alkaline phosphatase $K_{cat}$ and $K_m$ values increases in an inorganic pyrophosphate (PPi) hydrolysis assay.

7. The method of claim 2, further comprising:
   providing at least one solution selected from the group consisting of: load dilution solution, pre-equilibration solution, equilibration solution, wash solution, and elution solution to the eluate produced following Hydrophobic Interaction Chromatography (HIC) separation; and (a) decreasing in said at least one solution a concentration of at least one metal ion selected from the group consisting of: Nickel (Ni), Cobalt (Co), Copper (Cu), Manganese (Mn), Chromium (Cr), and Molybdenum (Mo);

(b) increasing in said at least one solution a concentration of at least one metal ion selected from the group consisting of: Zinc (Zn) and Silicon (Si); or (c) both (a) and (b).

8. The method of claim 1, comprising decreasing the concentration of Nickel (Ni) to less than about 1.87 ppm or less than about 0.7 ppm.

9. The method of claim 1 comprising increasing Zinc concentration to about 550 ppm to about 680 ppm.

10. The method of claim 1, wherein the recombinant alkaline phosphatase comprises the structure of W-sALP-X-Fc-Y-$D_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region;

$D_n$ is a poly-aspartate, poly-glutamate, or combination thereof, wherein n=10 or 16; and said sALP is a soluble alkaline phosphatase.

11. The method of claim 10, wherein:

a) said sALP comprises an active anchored form of alkaline phosphatase (ALP) without C-terminal glycolipid anchor (GPI);

b) said alkaline phosphatase (ALP) is tissue-non-specific alkaline phosphatase (TNALP);

c) said sALP is encoded by a polynucleotide encoding a polypeptide comprising the sequence as set forth in L1-S485 of SEQ ID NO:1;

d) said sALP comprises the sequence as set forth in L1-S485 of SEQ ID NO:1;

e) said sALP is capable of catalyzing the cleavage of inorganic pyrophosphate (PPi);

f) n=10;

g) W and Z are absent from said polypeptide;

h) said Fc comprises a CH2 domain, a CH3 domain and a hinge region; and/or i) said Fc is a constant domain of an immunoglobulin selected from the group consisting of IgG-1, IgG-2, IgG-3, IgG-3 and IgG-4.

12. The method of claim 11, wherein said Fc is a constant domain of an immunoglobulin IgG-1.

13. The method of claim 12, wherein said Fc comprises the sequence as set forth in D488-K714 of SEQ ID NO:1.

14. The method of claim 10, wherein the recombinant alkaline phosphatase is encoded by a polynucleotide encoding a polypeptide comprising the sequence as set forth in SEQ ID NO:1 and/or comprises the sequence set forth in SEQ ID NO: 1.

15. The method of claim 7, wherein the at least one solution comprises at least one of from about 0.2M to about 1.5M sodium sulfate, from about 0.2 to about 3M ammonium sulfate, and from about 0.5M to about 3M sodium chloride.

16. The method of claim 7, further comprising decreasing in said at least one solution a concentration of at least one metal ion selected from the group consisting of: Nickel (Ni), Cobalt (Co), Copper (Cu), Manganese (Mn), Chromium (Cr), and Molybdenum (Mo).

17. The method of claim 7, further comprising increasing in said at least one solution a concentration of at least one metal ion selected from the group consisting of: Zinc (Zn) and Silicon (Si).

* * * * *